(12) United States Patent
Berry et al.

(10) Patent No.: US 7,045,585 B2
(45) Date of Patent: May 16, 2006

(54) METHODS OF COATING A DEVICE USING ANTI-THROMBIN HEPARIN

(75) Inventors: Leslie Roy Berry, Ontario (CA); Maureen Andrew, deceased, late of Ontario (CA); by Hugh O'Brodovich, legal representative, Oakville (CA); Anthony Kam Chuen Chan, Ontario (CA)

(73) Assignee: Hamilton Civic Hospital Research Development Inc., Ontario (CA)

( * ) Notice: Subject to any disclaimer, the term of this patent is extended or adjusted under 35 U.S.C. 154(b) by 309 days.

(21) Appl. No.: 10/101,568

(22) Filed: Mar. 20, 2002

(65) Prior Publication Data

US 2003/0124705 A1 Jul. 3, 2003

Related U.S. Application Data

(63) Continuation-in-part of application No. 08/768,035, filed on Dec. 17, 1996, now Pat. No. 6,491,965, which is a continuation-in-part of application No. 08/564,976, filed on Nov. 30, 1995, now Pat. No. 6,562,781.

(60) Provisional application No. 60/277,619, filed on Mar. 22, 2001.

(51) Int. Cl.
*A61L 27/00* (2006.01)
*C07K 14/435* (2006.01)
*C07K 14/00* (2006.01)
*A61F 11/00* (2006.01)

(52) U.S. Cl. ............... 527/300; 530/350; 530/402; 623/920

(58) Field of Classification Search ............. 530/350, 530/402; 623/920; 527/300; 427/300
See application file for complete search history.

(56) References Cited

U.S. PATENT DOCUMENTS

| | | |
|---|---|---|
| 2,824,092 A | 2/1958 | Thompson |
| 3,616,935 A | 11/1971 | Love et al. |
| 3,676,612 A | 7/1972 | Merrill et al. |
| 3,842,061 A | 10/1974 | Andersson et al. |
| 4,055,635 A | 10/1977 | Green et al. |
| 4,213,962 A | 7/1980 | Miura et al. |
| 4,301,153 A | 11/1981 | Rosenberg |
| 4,340,589 A | 7/1982 | Uemura et al. |
| 4,356,170 A | 10/1982 | Jennings et al. |
| 4,446,126 A | 5/1984 | Jordan |
| 4,448,718 A | 5/1984 | Yannas et al. |
| 4,465,623 A | 8/1984 | Chanas et al. |
| 4,496,550 A | 1/1985 | Lindahl et al. |
| 4,510,084 A | 4/1985 | Eibl et al. |
| 4,526,714 A | 7/1985 | Feijen et al. |
| 4,585,754 A | 4/1986 | Meisner et al. |
| 4,613,665 A | 9/1986 | Larm |
| 4,623,718 A | 11/1986 | Collen |
| 4,634,762 A | 1/1987 | Feijen et al. |
| 4,656,161 A | 4/1987 | Herr |
| 4,678,671 A | 7/1987 | Feijen et al. |
| 4,689,323 A | 8/1987 | Mitra et al. |
| 4,731,073 A | 3/1988 | Robinson |
| 4,745,180 A | 5/1988 | Moreland et al. |
| 4,863,907 A | 9/1989 | Sakurai et al. |
| 4,920,194 A | 4/1990 | Feller et al. |
| 4,935,204 A | 6/1990 | Seidel et al. |
| 4,987,181 A | 1/1991 | Bichon et al. |
| 4,990,502 A | 2/1991 | Lormeau et al. |
| 5,002,582 A | 3/1991 | Guire et al. |
| 5,023,078 A | 6/1991 | Halluin |
| 5,061,750 A | 10/1991 | Feijen et al. |
| 5,071,973 A | 12/1991 | Keller et al. |
| 5,084,273 A | 1/1992 | Hirahara |
| 5,134,192 A | 7/1992 | Feijen et al. |
| 5,159,050 A | 10/1992 | Onwumere |
| 5,171,264 A | 12/1992 | Merrill |
| 5,182,259 A | 1/1993 | Kita |
| 5,182,317 A | 1/1993 | Winters et al. |
| 5,222,971 A | 6/1993 | Willard et al. |
| 5,262,451 A | 11/1993 | Winters et al. |
| 5,270,046 A | 12/1993 | Sakamoto et al. |
| 5,275,838 A | 1/1994 | Merrill |
| 5,280,016 A | 1/1994 | Conrad et al. |
| 5,308,617 A | 5/1994 | Halluin |
| 5,310,881 A | 5/1994 | Sakurai et al. |
| 5,319,072 A | 6/1994 | Uemura et al. |
| 5,330,907 A | 7/1994 | Philapitsch et al. |

(Continued)

FOREIGN PATENT DOCUMENTS

EP 0 081 853 6/1983

(Continued)

OTHER PUBLICATIONS

Radoff et al., "Radioreceptor Assay for Advanced Glycosylation End Products," Diabetes, vol. 40, pp. 1731-1738, Dec. 1991.

(Continued)

*Primary Examiner*—Janet Andres
*Assistant Examiner*—Gyan Chandra
(74) *Attorney, Agent, or Firm*—Millen, White, Zelano, Branigan, P.C.

(57) ABSTRACT

Novel conjugates of glycosaminoglycans, particularly heparin and dermatan sulfate, and amine containing species and therapeutic uses thereof are described. In particular, mild methods of conjugating heparins to proteins, such as anti-thrombin III and heparin cofactor II, which provide covalent conjugates which retain maximal biological activity are described. Uses of these conjugates to prevent thrombogenesis, in particular in lung airways, such as found in infant and adult respiratory distress syndrome, and on surfaces in contact with blood are also described.

5 Claims, 51 Drawing Sheets

U.S. PATENT DOCUMENTS

| | | | |
|---|---|---|---|
| 5,338,770 | A | 8/1994 | Winters et al. |
| 5,364,350 | A | 11/1994 | Dittmann |
| 5,436,291 | A | 7/1995 | Levy et al. |
| 5,455,040 | A | 10/1995 | Marchant |
| 5,510,418 | A | 4/1996 | Rhee et al. |
| 5,529,986 | A | 6/1996 | Larsson et al. |
| 5,556,708 | A | 9/1996 | Horl et al. |
| 5,589,516 | A | 12/1996 | Uriyu et al. |
| 5,652,014 | A | 7/1997 | Galin et al. |
| 5,741,852 | A | 4/1998 | Marchant et al. |
| 5,741,881 | A | 4/1998 | Patnaik |
| 5,762,944 | A | 6/1998 | Inoue et al. |
| 5,782,908 | A | 7/1998 | Cahalan et al. |
| 5,843,172 | A | 12/1998 | Yan |
| 5,851,229 | A | 12/1998 | Lentz et al. |
| 5,855,618 | A | 1/1999 | Patnaik et al. |
| 5,866,113 | A | 2/1999 | Hendriks et al. |
| 5,876,433 | A | 3/1999 | Lunn |
| 5,879,697 | A | 3/1999 | Ding et al. |
| 5,891,196 | A | 4/1999 | Lee et al. |
| 5,944,753 | A | 8/1999 | Galin et al. |
| 5,945,457 | A | 8/1999 | Plate et al. |
| 5,955,438 | A | 9/1999 | Pitaru et al. |
| 6,024,918 | A | 2/2000 | Hendriks et al. |
| 2001/0007063 | A1 | 7/2001 | Oyama et al. |
| 2001/0034336 | A1 | 10/2001 | Shah et al. |

FOREIGN PATENT DOCUMENTS

| | | |
|---|---|---|
| EP | 0 098 814 | 1/1984 |
| EP | 0 137 356 | 4/1985 |
| EP | 0 344 068 | 11/1989 |
| EP | 0 345 616 | 12/1989 |
| FR | 2 635 019 | 2/1990 |
| WO | 89/09624 | 10/1989 |
| WO | 90/01332 | 2/1990 |
| WO | WO 95/05400 | 2/1995 |

OTHER PUBLICATIONS

Rolf Axen et al., "Chemical Fixation of Enzymes to Cyanogen Halide Activated Polysaccharide Carriers," Eur J. Biochem., vol. 18, pp. 351-360 (1971).

Joachim Kohn et al., "A New Approach (Cyano-Transfer) for Cyanogen Bromide Activation of Sepharose at Neutral pH, which Yields Activated Resins, Free of Interfering Nitrogen Derivatives," Biochemical and Biophysical Research Communications, vol. 107, No. 3, pp. 878-884 (1982).

Chemical Abstracts, vol. 103: 171707k (1985).

Pharmacology, vol. 103, p. 45 (1985).

Takuya Fujuita et al., "Alteration of biopharmaceutical properties of drugs by their conjugation with water-soluble macromolecules: uricase-dextran conjugate," Journal of Controlled Release, vol. 11, pp. 149-156 (1990).

Te Piao King et al., "Immunochemical studies of dextran coupled ragweed pollen allergen, antigen E[1]," Archives of Biochemistry and Biophysics, pp. 464-473 (1975).

Fu-Tong Liu et al., "Immunological tolerance to allergenic protein determinants; A therapeutic approach for selective inhibition of IgE antibody production," Proc. Natl., Acad. Sci. USA, vol. 76, No. 3, pp. 1430-1434 (1979).

Hiroshi Maeda et al., "Conjugation of Poly(styrene-co-maleic acid) derivatives to the antitumor protein neocarzinostatin: pronounced improvements in pharmacological properties," J. Med. Chem., vol. 28, pp. 455-461 (1985).

M. Okada et al., "Suppression of IgE antibody response against ovalburnin by the chemical conjugate of ovalburnin with a polyaspartic acid derivative," Int. Archs Allergy appl. Immun., vol. 76, pp. 79-81 (1985).

Mitsuko USUI et al., "IgE-selective and antigen-specific unresponsiveness in mice," The Journal of Immunology, vol. 122, No. 4, pp. 1266-72 (1979).

Berry et al., (1998) J. Biochem. 124: 434-439.

M.M. Maimone et al., "Structure of A Dermatan Sulfate Hexasaccharide That Binds To Heparin Cofactor II With High Affinity," J. of Bio. Chem., vol. 265, No. 30, pp. 18263-18271 (1990).

Uno Takeji et al., "Evaluation for Antithrombogenicity on the Surface of Heparinized Biomedical Material Using Thrombin-Antithrombin III Complex," Chemical Abstracts, vol. 122, No. 25, Abstract No. 306176 (Jun. 19, 1995).

M.W.C. Hatton et al., "Inhibition of Thrombin By Antithrombin III in the Presence of Certain Glycosaminoglycans Found in the Mammalian Aorta," Thrombosis Research, 13:4, 655-670 (Apr. 24, 1978).

M. Verstraete, "Prevention of Thrombosis in Arteries: Novel Approaches," J. Cardiovasc. Pharmacol., 7 (Suppl. 3) S191-S205 (1985).

I Bjork et al., Permanent Activation of Antithrombin By Covalent Attachment of Heparin Oligosaccharides FEBS Letters, vol. 143, pp. 96-100 (1982).

R. Ceustermans et al., "Preparation, Characterization, and Turnover Properties of Heparin-Antithrombin III Complexes Stabilized by Covalent Bonds," The Journal of Biological Chemistry, vol. 257, 3401-3408 (1982).

M.W.C. Hatton et al., "Tritiation of Commercial Heparins by Reaction with $NaB^3H_4$: Chemical Analysis and Biological Properties of the Product," Analytical Biochemistry, vol. 106, 417-416 (1980).

M. Hoylaerts et al., "Covalent Complexes Between Low molecular Weight Heparin Fragments and Antithrombin III-Inhibition Kinetics and Turnover Parameters," Thromb Haemostas, vol. 49, pp. 109-115 (1983).

M. Hoylaerts et al., "Involvement of Heparin Chain Length in the Heparin-Catalyzed Inhibition of Thrombin By Antithrombin III," The Journal of Biological Chemistry, vol. 259, pp. 5670-5677 (1984).

C. Mattsson et al., Antithrombic Properties in Rabbits of Heparin and Heparin Fragments Covalently Coupled to Human Antithrombin III, J. Clin. Invest., vol. 75, pp. 1169-1173 (1985).

A.K.C. Chan et al., "Antithrombin-Heparin Covalent Complex A Novel Approach For Improving Thromboresistance of Cardiovascular Devices," Pop Health HSC, p. 99.

A.K.C. Chan et al., "Evaluation of Antithrombin-Heparin Covalent Complex Coated Endoluminal Grafts in Rabbits," Pop, Health HSC., p. 102.

Pharmacokinetic of ATH After Intravenous Injection - by ELISA of Plasma AT

Pharmacokinetic of ATH After Subcutaneous Injection - by ELISA of AT

Anti-Factor Xa Activities of BAL After Intratracheal Instillation of ATH

Cumulative Blood Loss After Treatment in Rabbit Bleeding Ear Model

Cumulative Blood Loss After Treatment (With Outlier Removed) in Rabbit Bleeding Ear Model

* bleeding less than 200 microlitre considered acceptable

Plasma Anti-Factor Xa Activity in Rabbit Bleeding Ear Model

Comparison of the Effect of Grafting ATH or Hirudin onto Polyurethane

In Vivo Rabbit Experiments

* $p = 0.03$ (ATH vs HIRUDIN, 1 tail $t$-test)

Comparison of the Effect of Grafting ATH or AT onto Polyurethane

In Vivo Rabbit Experiments

Luminal Surface of Tubing After Exposed to Blood for Three Hours in Rabbit

Characterization of ATH (antithrombin-heparin complex)
1. Structural analysis 1  2

1 2 3

A – Native Gel

ATH    ATH    AT    AT
          Fn      UFH   UFH
                    Fn

B – SDS Gel

ATH    ATH    AT    AT
          Fn      UFH   UFH
                   Fn

A – Native Gel

IIa    IIa    IIa    IIa
      ATH   ATH   Fn
              Fn

B- SDS Gel

IIa    IIa    IIa    IIa
      ATH   ATH   Fn
              Fn

A

B 1 2 3 4 5 6 7 8 9

METHODS OF COATING A DEVICE USING ANTI-THROMBIN HEPARIN

This application is a Continuation In Part of U.S. application Ser. No. 08/768,035, which is a Continuation In Part of U.S. application Ser. No. 08/564,976; and claims the benefit of provisional application 60/277,619 filed Mar. 22, 2001, which is incorporated by reference herein. The entire disclosures of U.S. application Ser. Nos. 08/564,976, filed Nov. 30, 1995, now U.S. Pat. No. 6,562,781, and Ser. No. 08/768,035, filed Dec. 17, 1996, now U.S. Pat. No. 6,491,965, are incorporated by reference herein.

FIELD OF THE INVENTION

This invention relates to new chemical compounds comprising covalent conjugates of glycosaminoglycans, particularly heparins, methods for their preparation, their pharmaceutical compositions and therapeutic uses thereof.

BACKGROUND OF THE INVENTION

Heparin is a sulfated polysaccharide which consists largely of an alternating sequence of hexuronic acid and 2-amino-2-deoxy-D-glucose. Heparin and a related compound, dermatan sulfate, are of great importance as anticoagulants for clinical use in the prevention of thrombosis and related diseases. They are members of the family of glycosaminoglycans, (GAGs), which are linear chains of sulfated repeating disaccharide units containing a hexosamine and a uronic acid. Anticoagulation using GAGs (such as heparin and dermatan sulfate) proceeds via their catalysis of inhibition of coagulant enzymes (the critical one being thrombin) by serine protease inhibitors (serpins) such as antithrombin III (ATIII) and heparin cofactor II (HCII). Binding of the serpins by the catalysts is critical for their action and occurs through specific sequences along the linear carbohydrate chain of the glycosaminoglycan (GAG). Heparin acts by binding to ATIII via a pentasaccharide sequence, thus potentiating inhibition of a variety of coagulant enzymes (in the case of thrombin, heparin must also bind to the enzyme). Heparin can also potentiate inhibition of thrombin by binding to the serpin HCII. Dermatan sulfate acts by specifically binding to HCII via a hexasaccharide sequence, thus potentiating only the inhibition of thrombin. Since glycosaminoglycans (particularly heparin) can bind to other molecules in vivo or be lost from the site of action due to a variety of mechanisms, it would be advantageous to keep the GAG permanently associated with the serpin by a covalent bond.

Covalent complexes between ATIII and heparin have been produced previously; see, e.g., Bjork et al., (1982) FEBS Letters 143(1):96–100, and by Collen et al., U.S. Pat. No. 4,623,718. These conjugates required covalent modification of the heparin prior to its conjugation. The product by Bjork et al. (produced by reduction of the Schiff base between the aldehyde of a 2,5-D-anhydromannose terminus of heparin, produced by partial depolymerization of heparin to heparin fragments with nitrous acid, and a lysyl amino of ATIII) had undetectable antithrombin activity. The product by Collen et al. (produced by conjugation of carboxyl groups within the chain of the heparin molecule and lysyl amino groups of ATIII through amino-hexyl tolyl spacer arms) had a random attachment to the carboxyls of the uronic acids of the heparin moiety that might affect the ATIII binding sequence and in fact the specific anti-Xa (a coagulation protease which activates prothrombin to thrombin) activity was approximately 65% of the starting non-covalently linked unmodified heparin (J. Biol. Chem. 257:3401–3408 (1982)). The specific anti-thrombin activity would also be, therefore, 65% or less since both Xa and thrombin require heparin binding to ATIII. The bimolecular rate constant of the product by Collen et al. for inhibition of thrombin was claimed to be comparable to that of non-covalent mixtures of heparin saturated with ATIII (J. Biol. Chem. 259:5670–5677 (1984)). However, large molar excesses of heparin or covalent complex over thrombin (>10:1) were used to simplify the kinetics, which would mask the effect of any subpopulation of molecules with low activity. Specific antithrombin activities were not given.

In addition, heparin has also been covalently conjugated to other proteins (such as tissue plasminogen activator and erythropoietin) by Halluin (U.S. Pat. No. 5,308,617), using a similar method to that of Bjork et al. These conjugates suffered from the same problems associated with loss of heparin activity as with the Bjork conjugates. Coupling of heparin to affinity supports via a hydrazine linkage is reported in WO 95/05400. However, the hydrazine group is not commonly found in proteins and other macromolecules, and its incorporation often results in a decrease in biological activity. U.S. Pat. No. 4,213,962 describes heparin and antithrombin III coimmobilized on cyanogen bromide activated agarose. U.S. Pat. Nos. 5,280,016 and 4,990,502 describe the oxidation of heparin with periodate and reduction of the aldehydes so generated.

Therefore, it would be desirable to provide covalent conjugates of heparin and related glycosaminoglycans which retain maximal biological activity (e.g., anticoagulant activity) and improved pharmacokinetic properties and simple methods for their preparation. This invention fulfills these and other needs.

SUMMARY OF THE INVENTION

This invention provides a covalent conjugate comprising a glycosaminoglycan linked to another species by a covalent linkage wherein the species comprises at least one primary amino group, wherein the species is directly covalently linked via its amino group to a terminal aldose residue of the glycosaminoglycan. Preferably, the covalent linkage is an imine (>C=N—) formed between the amino group of the first species and the C1 of the terminal aldose, or the amine reduction product thereof (>CH—NH—). The glycosaminoglycan is preferably heparin or dermatan sulfate. The amine containing species may be a small molecule, such as a drug or a label, a macromolecule such as antithrombin III or heparin cofactor II, or a solid or porous or semiporous support such as is typically used in affinity chromatography.

In an aspect of the invention, a covalent conjugate is provided comprising heparin and antithrombin III linked by a covalent species characterized by one or more of the following properties:
  (a) stable at 4° C. for at least 60 days, or at least 90 days;
  (b) longer half-life than heparin;
  (c) more effective at inhibiting thrombin than free antithrombin III and heparin;
  (d) heparin component stoichiometrically activates antithrombin III in the covalent conjugate
  (e) specific non-catalytic anti-factor Xa activity of 20–100 U/mg, preferably 30 to 60 U/mg, more preferably 40 to 50 U/mg heparin;
  (f) heparin chains having two pentasaccharides, preferably more than 10%, 20%, 35%, or 50% of the heparin chains having two pentasaccharides;

(g) neutralized preferably with protamine or human platelet factor 4;
(h) inactivates thrombin bound to fibrin;
(i) exosite 2 of thrombin is not required for the covalent conjugate to bind to thrombin;
(j) molar ratio of heparin to antithrombin is about 1–2, preferably 1.1;
(k) possesses catalytic activity by activating antithrombin III to which the covalent conjugate is not conjugated to act catalytically; and
(l) possesses >60%, typically >90, more typically >95%, and most typically >98% of intact unconjugated heparin antithrombin activity.

In accordance with an aspect of the invention a selected covalent conjugate of the invention has the characteristics (d), (h), and (k); (c), (d), (h), and (k); (c), (d), (f), (h), and (k); (c), (d), (h), (l), and (k); (c), (f), (h), and (l); (c), (f), (h), and (k); (c), (l), (h), (k), and (l); (f), (h), and (k); (a) through (k); or (a) through (l).

Selected covalent conjugates may have one or more of the following properties (a) heparin chains with greater than 80 saccharide units; (b) 1 to 2, preferably 1 to 1.5, more preferably 1.3–1.5 catalytic sites per heparin chain; (c) a catalytic activity about 1–3, preferably 1.5 to 2 fold greater than heparin alone; and (d) an average molecular weight for conjugated heparin chains of 10,000 to 20,000, preferably 12,000 to 17, 000, more preferably about 15,000 to 16,000, most preferably about 15,000.

The invention relates to a conjugate composition comprising glycosaminoglycans to a substantial degree covalently bonded or linked to an amino-group containing species by —CO—$CH_2$—NH— said —CO—$CH_2$— portion being derived from said glycosaminoglycans and said —NH— portion being derived from an amino group of said species. The invention also relates to a conjugate composition comprising glycosaminoglycans covalently bonded or linked to a protein to a substantial degree by —CO—$CH_2$—NH—. Also provided is a conjugate composition to a substantial degree of the formula: glycosaminoglycan—CO—$CH_2$—NH-protein. The glycosaminoglycans and species may be covalently linked by an α-carbonyl amine (—CO—$CH_2$—NH—) formed by a predominant or essentially complete subsequent Amadori rearrangement.

In an embodiment of the invention, the conjugate composition is heparin or a fragment thereof linked to antithrombin III.

The terms "substantial degree" and "substantial amount" refer to more than 60%, 70%, or 80% of a selected occurrence e.g. Amadori rearrangement or covalent linkage. "Predominant degree" and "predominant amount" refer to more than 85%, 90% or 95% of a selected occurrence e.g. Amadori rearrangement or covalent linkage "Essentially complete degree" and "essentially complete amount" refer to more than 98 or 99%, or about 100% of a selected occurrence e.g. Amadori rearrangement or covalent linkage.

A covalent conjugate composition is also provided comprising glycosaminoglycans linked by covalent linkages to a species comprising at least one primary amino group, wherein the species is directly linked via the amino group to a terminal aldose residue of the glycosaminoglycans, the covalent linkages comprising an α-carbonyl amine formed by a substantial amount of subsequent Amadori rearrangement of imines resulting from reaction between the amino group and the terminal aldose residue of the glycosaminoglycans, or a pharmaceutically acceptable salt thereof. In an embodiment, the linkages comprise an α-carbonyl amine formed by a predominant or essentially complete subsequent Amadori rearrangement.

The invention also relates to isolated covalent conjugates of the invention, and compositions comprising covalent conjugates of the invention.

The invention also provides novel and mild methods of preparing the above covalent conjugates that result in conjugates with improved pharmacokinetic properties and biological activity. The methods comprise incubating the glycosaminoglycans with the amine-containing species under conditions that allow imine formation between the terminal aldose residue of the glycosaminoglycan and the amine. The imine may be reduced to the corresponding amine or alternatively may be allowed to rearrange under mild conditions (Amadori rearrangement) to a α-carbonyl amine.

The invention therefore contemplates a process for preparing a covalent conjugate or conjugate composition of molecules comprising at least one primary amino group linked to glycosaminoglycans by covalent bonds or linkages, the process comprising:

(a) incubating the glycosaminoglycans with the molecules at a pH and for a time sufficient for formation of an imine between the amino group and a terminal aldose residue of the glycosaminoglycans, and at a time and temperature sufficient for the imines to undergo a substantial amount of subsequent Amadori rearrangement to an α-carbonyl amine forming the covalent linkages; and (b) isolating the covalent conjugate or conjugate composition.

The invention also provides a conjugate or conjugate composition comprising glycosaminoglycans and molecules comprising at least one amino group, wherein the amino group is directly linked to the glycosaminoglycans by covalent linkages, prepared by a process comprising:

(a) incubating the glycosaminoglycans with the molecules at a pH and for a time sufficient for formation of an imine between the amino group and a terminal aldose residue of the glycosaminoglycans, and at a time and temperature sufficient for the imines to undergo a substantial amount of subsequent Amadori rearrangement to an α-carbonyl amine forming the covalent linkages; and (b) isolating the covalent conjugate or conjugate composition; or a pharmaceutically acceptable salt thereof.

In an embodiment, the imine undergoes a predominant amount of, or essentially complete subsequent Amadori rearrangement.

In an aspect of the invention a process is provided for preparing a conjugate composition comprising heparin and antithrombin III comprising:

(a) incubating intact heparin with antithrombin at a pH and for a time sufficient for formation of an imine between an amino group of the antithrombin III and a terminal aldose residue of heparin, and at a time and temperature sufficient for the imines to undergo a substantial amount of subsequent Amadori rearrangement to an α-carbonyl amine forming the covalent linkages; and (b) isolating the conjugate composition.

In another aspect of the invention a process is provided for preparing a conjugate composition comprising a substantial amount of heparin directly covalently linked to antithrombin III wherein more than 10%, 20%, 35%, or 50% of the heparin chains have two pentasaccharides comprising:

(a) incubating intact heparin with antithrombin at a pH and for a time sufficient for formation of an imine between an amino group of the antithrombin III and a terminal aldose residue of heparin, and at a time and temperature sufficient for the imines to undergo a substantial amount of subsequent Amadori rearrangement to an α-carbonyl amine forming the covalent linkages; and (b) isolating the conjugate composition.

In step (a) of the process, the incubation is preferably carried out from about 3 days to two weeks, and in selected processes 5 days, 10 days, or 2 weeks. Step (a) is also preferably carried out at a temperature of 35° C. to 45° C., more preferably 40° C.

The above process for preparing a conjugate composition comprising heparin and antithrombin III provides a conjugate composition with a substantial amount of heparin directly covalently linked to antithrombin III.

The invention further provides pharmaceutical compositions comprising covalent conjugates or conjugate compositions of the invention and a pharmaceutically acceptable carrier. A pharmaceutical composition of the invention may be suitable for administration to a mammal. In an embodiment, a pharmaceutical composition of the invention is in the form of an aqueous solution for injection, in the form of an ointment, or in the form of an aerosol.

In an embodiment, a pharmaceutical composition of substantially pure covalent conjugates is provided comprising heparin directly covalently linked without an intermediate spacer or linker by a terminal aldose residue to an amino group of antithrombin III. The heparin and antithrombin III may be linked by a —CO—CH$_2$—NH— group formed by Amadori rearrangement of a —HCOH—HC═N— group resulting from reaction between the amino group and a C1 carbonyl group of the terminal aldose residue. The glycosaminoglycan may be covalently bonded or linked to the amino-group of the species by —CO—CH$_2$—NH, said —CO—CH$_2$— portion being derived from the glycosaminoglycan and the —NH— portion being derived from an amino group of the species. The glycosaminoglycan may be covalently bonded to the species by —CO—CH$_2$—NH—. The molar ratio of amino-containing species to glycosaminoglycan in a covalent conjugate or composition of the invention may be less than one.

The invention also relates to a pharmaceutical composition of substantially pure covalent conjugates comprising heparin directly covalently linked to antithrombin III which provides a longer anticoagulant effect compared to heparin.

In an embodiment, a pharmaceutical composition is provided consisting essentially of covalent conjugates comprising heparin directly covalently linked without an intermediate spacer or linker by a terminal aldose residue to an amino group of antithrombin Ill.

In still another embodiment, a pharmaceutical composition is provided consisting of covalent conjugates comprising heparin directly covalently linked without an intermediate spacer or linker by a terminal aldose residue to an amino group of antithrombin III.

The invention also contemplates a substantially pure composition comprising covalent conjugates comprising glycosaminoaglycans and a molecule comprising at least one amino group, wherein the glycosaminoglycan is heparin, the molecule is antithrombin III and the covalent conjugate is antithrombin-heparin (ATH), and wherein the amino group is directly linked without an intermediate spacer or linker to the glycosaminoglycan by a covalent linkage, wherein the covalent conjugates are made by a process comprising:

(a) incubating the glycosaminoglycans with the molecules at a pH and for a time sufficient for formation of imines between the amino group and a terminal aldose residue of the glycosaminoglycans, and at a time and temperature sufficient for the imines to undergo a substantial amount of subsequent Amadori rearrangement to an α-carbonyl amine forming the covalent linkages; and (b) isolating the covalent conjugates.

A pharmaceutical composition of the invention may activate antithrombin III to which the covalent conjugate is not conjugated. In an aspect, a pharmaceutical composition possesses >90% of intact unconjugated heparin antithrombin activity. In another aspect the heparin of the covalent conjugate stoichiometrically activates antithrombin III in the covalent conjugate and catalytically activates antithrombin III circulating in a patient. A pharmaceutical composition may inactivate thrombin and Factor Xa.

In an aspect of the invention a pharmaceutical composition is provided comprising dermatan sulfate linked to heparin cofactor II by a covalent linkage.

The invention still further provides therapeutic uses of the covalent conjugates, conjugate compositions, and pharmaceutical compositions of the invention.

The invention also relates to the prevention and treatment, in humans or other mammals, of conditions where inhibition of thrombin is required. The covalent conjugates and conjugate compositions of the invention are expected to be useful in mammals, including man, in treatment of prophylaxis of thrombosis and hypercoagulability in blood and tissues.

In an embodiment, the invention relates to a method of achieving an anticoagulant effect in a patient comprising administering a covalent conjugate, conjugate composition, or pharmaceutical composition of the invention.

The invention additionally provides uses of the covalent conjugates and compositions of the invention in the preparation of medicaments for the prevention and/or treatment of conditions where inhibition of thrombin is required.

The invention also provides methods for reducing the thrombogenicity of a material, such as a synthetic polymer, by coating the material with a covalent conjugate, conjugate composition, or pharmaceutical composition of the invention, especially the heparin-antithrombin III conjugate. Materials treated by this method are useful as medical or prosthetic devices.

The invention provides a material for use in a medical or prosthetic device comprising a polymer coated with a covalent conjugate or conjugate composition of the invention. The covalent conjugates may be covalently attached to an intermediate monomer linker, for example, allyl glycidyl ether.

In an aspect the invention provides a material for use in a medical or prosthetic device comprising a polymer coated with or in contact with a covalent conjugate or conjugate composition of the invention. The covalent conjugate or composition may comprise a glycosaminoglycan covalently bonded to a species (e.g. protein) to a substantial degree by —CO—CH$_2$—NH—. The —CO—CH2- portion may be derived from the glycosaminoglycans and the —NH— portion may be derived from an amino group of the species. The material may comprise a covalent conjugate or composition to a substantial degree of the formula: glycosaminoglycan-CO—CH$_2$—NH-protein. The covalent conjugate or composition in contact with the material may have a molar ratio of species (e.g. protein) to glycosaminoglycan less than one. In a preferred embodiment of the invention, the covalent conjugate or composition is between heparin and antithrombin III. In a more preferred embodiment, heparin is directly covalently linked without an intermediate spacer or linker by a terminal aldose residue to an amino group of antithrombin.

The term "coat", "coating" or "in contact with" refers to a condition of proximity between a material and a covalent conjugate of the invention. The association may be non-covalent i.e. where the juxtaposition is energetically favoured by for example, hydrogen-bonding, van der Waals, or electrostatic or hydrophobic interactions, or it may be covalent.

The invention also relates to a material for use in a medical or prosthetic device comprising a polymer coated with a conjugate composition, the conjugate composition comprising glycosaminoglycans linked to a species by covalent linkages, wherein the species comprises at least one primary amino group, and wherein the species is directly covalently linked via the amino group to a terminal aldose residue of the glycosaminoglycans, said covalent linkages comprising an α-carbonyl amine formed by a substantial amount of subsequent Amadori rearrangement of an imine resulting from reaction between the amino group and the terminal aldose residue of the glycosaminoglycans.

The invention relates to a material for use in a medical or prosthetic device comprising a polymer coated with a covalent conjugate composition, the covalent conjugate composition comprising glycosaminoglycans linked to a species by covalent linkages, wherein the glycosaminoglycans are heparins, the species is antithrombin III, and the covalent conjugate composition comprises antithrombin III-heparin (ATH), the ATH being covalently attached to the polymer, and wherein the species is directly covalently linked via the amino group to a terminal aldose residue of the glycosaminoglycans to a substantial degree by an α-carbonyl linkage. In an aspect, the ATH is covalently attached to the polymer.

The material of the invention may be pharmaceutically suitable for insertion into a mammal, preferably a human.

The invention also relates to a coating for a medical or prosthetic device comprising covalent conjugates or compositions of the invention.

In an aspect, the invention provides a medical or prosthetic device having a blood-contacting surface with a covalent conjugate or composition of the invention thereon.

In another aspect, an implantable medical or prosthetic device with a modified surface is provided comprising a medical device with at least one surface for contacting blood, wherein the contacting surface is modified by treatment with a covalent conjugate or covalent composition of the invention.

The invention relates to an implantable medical or prosthetic device with at least one contacting surface for contacting blood comprising a layer on the contacting surface comprising the product of incubating heparin with antithrombin III under conditions which allow imine formation between the terminal aldose residue of the heparin and an amine of the antithrombin III and allowing Amadori rearrangement to an α-carbonyl amine.

The invention relates to an implantable medical or prosthetic device with at least one contacting surface for contacting blood wherein the contacting surface comprises a coating of the invention. The association between the surface of a medical or prosthetic device and coating may be covalent or non-covalent.

The invention also provides a method of coating a medical device or prosthetic device comprising applying covalent conjugates or compositions of the invention to the device to form a coating on the device.

In an aspect the invention provides a method of forming a coating on a surface of a medical or prosthetic device comprising applying a product on the surface that is prepared by:
(a) incubating heparin with antithrombin III under conditions which allow imine formation between the terminal aldose residue of the heparin and an amine of the antithrombin III; and
(b) allowing Amadori rearrangement to an α-carbonyl amine The invention also relates to a method of imparting antithrombotic properties to a surface comprising modifying the surface by treatment with covalent conjugates or compositions of the invention.

Other features, objects and advantages of the invention and its preferred embodiments will become apparent from the detailed description that follows.

BRIEF DESCRIPTION OF THE DRAWINGS

FIG. 13 shows the pharmacokinetic of ATH after intravenous injection as measured by ELISA of Plasma AT.

DESCRIPTION OF THE PREFERRED EMBODIMENT

Figure 1:
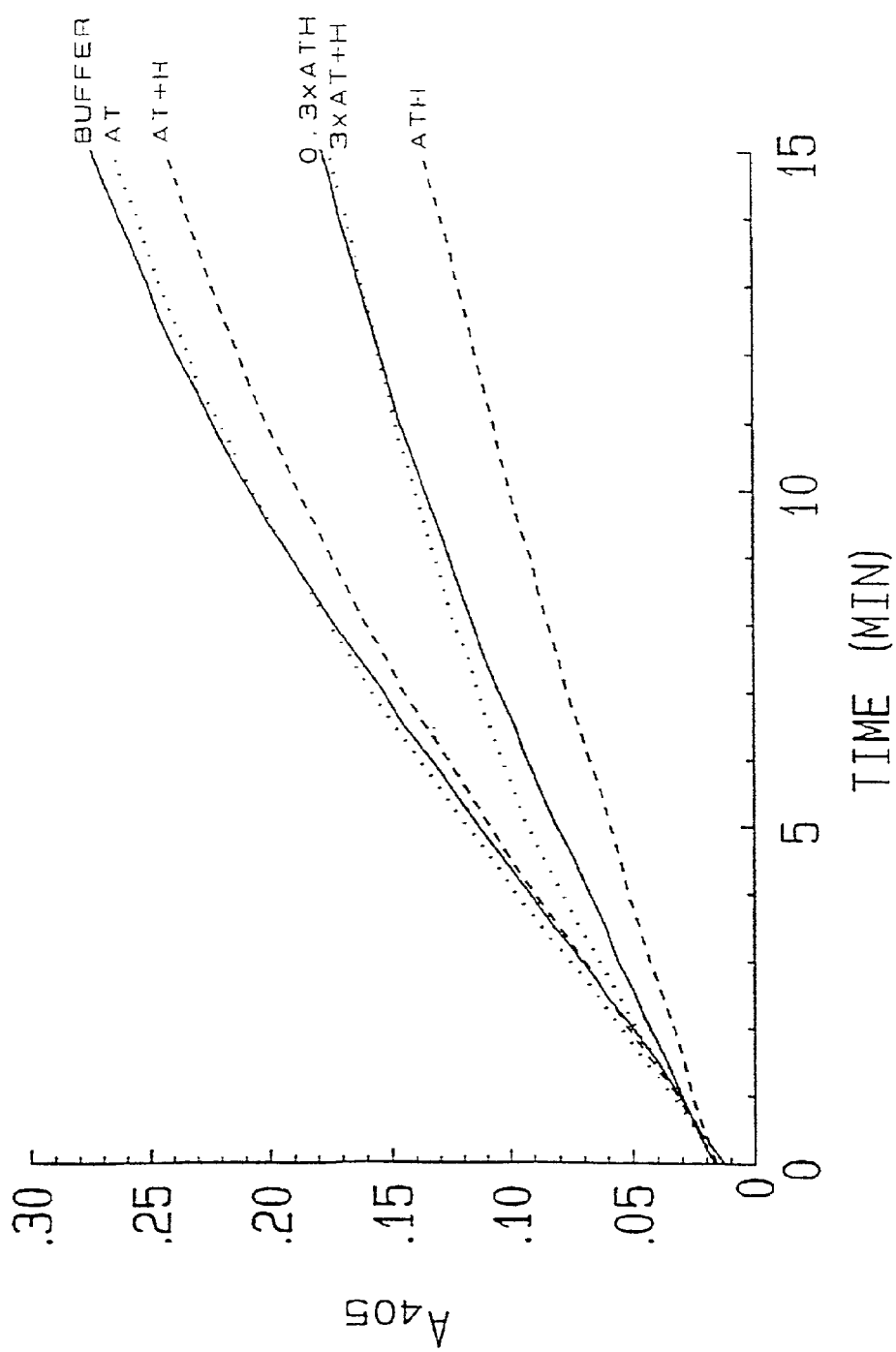
FIG. 1 compares the inhibition of thrombin activity by antithrombin III, noncovalent antithrombin III-heparin complexes and various concentrations of the covalent antithrombin III-heparin (ATH) conjugates of the present invention.

This invention provides novel covalent conjugates of glycosaminoglycans labelled at their terminal aldose residue with primary amine containing molecules. In particular, this invention provides novel covalent conjugates of heparin (Merck Index, 1980), dermatan sulfate (Tollefsen et al. (1990) J. Biol. Chem. 265:18263–18271) and fragments thereof with therapeutically significant serine protease inhibitors such as, for example, antithrombin III and heparin cofactor II, therapeutic uses thereof and methods for their preparation. The novel heparin conjugates of this invention are prepared under mild conditions, retain maximal anticoagulant activity compared to intact heparin, and have improved pharmacokinetic properties.

Glossary

Before describing the invention in greater detail the following definitions are set forth to illustrate and define the meaning and scope of the terms used to describe the invention herein.

The term "hexose" refers to a carbohydrate ($C_6H_{12}O_6$) with six carbon atoms. Hexoses may be aldohexoses such as, for example, glucose, mannose, galactose, idose, gulose, talose, allose and altrose, whose open chain form contains an aldehyde group. Alternatively, hexoses may be ketoses such as fructose, sorbose, allulose and tagatose, whose open chain form contains a ketone group.

The term "uronic acid" refers to the carboxylic acid formed by oxidation of the primary hydroxyl group of a carbohydrate and are typically named after the carbohydrate from which they are derived. Therefore, oxidation of the C6 hydroxyl of glucose gives glucuronic acid, oxidation of the C6 hydroxyl of galactose gives galacturonic acid and oxidation of the C6 hydroxyl of idose gives iduronic acid.

The term "hexosamine" refers to a hexose derivative in which at least one hydroxy group, typically the C2 hydroxy group, has been replaced by an amine. The amine may be optionally alkylated, acylated (such as with muramic acid), typically by an acetyl group, sulfonated, (O or N-sulfated), sulfonylated, phosphorylated, phosphonylated and the like. Representative examples of hexosamines include glucosamine, galactosamine, tagatosamine, fructosamine, their modified analogs and the like.

The term "glycosaminoglycan" refers to linear chains of largely repeating disaccharide units containing a hexosamine and a uronic acid. The precise identity of the hexosamine and uronic acid may vary widely and representative examples of each are provided in the definitions above. The disaccharide may be optionally modified by alkylation, acylation, sulfonation (O- or N-sulfated), sulfonylation, phosphorylation, phosphonylation and the like. The degree of such modification can vary and may be on a hydroxy group or an amino group. Most usually the C6 hydroxyl and the C2 amine are sulfated. The length of the chain may vary and the glycosaminoglycan may have a molecular weight of greater than 200,000 daltons, typically up to 100,000 daltons, and more typically less than 50,000 daltons. Glycosaminoglycans are typically found as mucopolysaccharides. Representative examples include, heparin, dermatan sulfate, heparan sulfate, chondroitin-6-sulfate, chondroitin-4-sulfate, keratan sulfate, chondroitin, hyaluronic acid, polymers containing N-acetyl monosaccharides (such as N-acetyl neuraminic acid, N-acetyl glucosamine, N-acetyl galactosamine, and N-acetyl muramic acid) and the like and gums such as gum arabic, gum Tragacanth and the like. See Heinegard, D. and Sommarin Y. (1987) Methods in Enzymology 144:319–373.

The term "directly covalently linked" refers to a covalent linkage between two species accomplished without the use of intermediate spacer or linkage units. Thus, when a first molecule is referred to as being directly covalently linked to a terminal aldose residue of a glycosaminoglycan via an amino group on the first molecule, this means that the nitrogen atom of the first molecule is bonded directly to an atom of the terminal aldose residue. This bond will be a covalent bond and may be a single, double or triple bond. Therefore, one of skill in the art will understand that heparin conjugates linked to another molecule via initial attachment of spacer groups such as polymethylene diamino linkers to the heparin molecule are not contemplated by this invention.

The term "protein" includes, but is not limited to, albumins, globulins (e.g., immunoglobulins), histones, lectins, protamines, prolamines, glutelins, phospholipases, antibiotic proteins and scleroproteins, as well as conjugated proteins such as phosphoproteins, chromoproteins, lipoproteins, glycoproteins, nucleoproteins.

The term "serpin" refers to a serine protease inhibitor and is exemplified by species such as antithrombin III and heparin cofactor II.

The term "amine" refers to both primary amines, $RNH_2$, and secondary amines RNH(R').

The term "amino" refers to the group >NH or —$NH_2$.

The term "imine" refers to the group >C=N— and salts thereof.

As used herein, the terms "treatment" or "treating" of a condition and/or a disease in a mammal, means:

(i) preventing the condition or disease, that is, avoiding any clinical symptoms of the disease;

(ii) inhibiting the condition or disease, that is, arresting the development or progression of clinical symptoms; and/or (iii) relieving the condition or disease, that is, causing the regression of clinical symptoms.

As used herein, the term "substantially pure" means, an object species is the predominant species present (i.e., on a molar basis it is more abundant than any other individual species in the composition), and preferably a substantially purified fraction is a composition wherein the object species comprises at least about 50 percent (on a molar basis) of all macromolecular species 15 present. Generally, a substantially pure composition will comprise more than about 80 to 90 percent of all macromolecular species present in the composition. Most preferably, the object species is purified to essential homogeneity (contaminant species cannot be detected in the composition by conventional detection methods) wherein the composition consists essentially of a single macromolecular species.

The conditions and diseases treated in the present invention include myocardial infarction and a large array of thrombotic states. These include fibrin deposition found in neonatal respiratory distress syndrome, adult respiratory distress syndrome, primary carcinoma of the lung, non-Hodgkins lymphoma, fibrosing alveolitis, and lung transplants. Also, the present invention can treat either acquired ATIII deficient states such as neonatal respiratory distress syndrome, L-asparaginase induced deficiency, cardiopulmonary bypass induced deficiency and sepsis or congenital ATIII deficient states. In the case of congenital ATIII deficiency, although it is unclear from the literature if any homozygous deficient infant has ever survived to the point of birth, life threatening thrombotic complications with ATIII levels of less than 0.25 Units/ml in heterozygotes requiring ATIII plus heparin may occur in up to 1 or 2 infants per year in the U.S.A.

The conditions and diseases treated in the present invention include those characterized by excess thrombin generation or activity. Such conditions often occur where a subject has been exposed to trauma, for example in surgical patients. Trauma caused by wounds or surgery results in vascular damage and secondary activation of blood coagulation. These undesirable effects may occur after general or orthopedic surgery, gynecologic surgery, heart or vascular surgery, or other surgical procedures. Excess thrombin may also complicate progression of natural diseases such as artherosclerosis which can cause heart attacks, strokes or gangrene of the limbs. Therefore, the methods and compositions of the present invention can be used to treat, prevent, or inhibit a number of important cardiovascular complications, including unstable angina, acute myocardial infarction (heart attack), cerebral vascular accidents (stroke), pulmonary embolism, deep vein thrombosis, arterial thrombosis, etc. The compositions and methods of the invention may be used to reduce or prevent clotting during dialysis and reduce or prevent intravascular coagulation during open heart surgical procedures.

In one aspect of the invention, methods and compositions are provided for preventing or inhibiting thrombin generation or activity in patients at increased risk of developing a thrombus due to medical conditions that disrupt hemostasis (e.g., coronary artery disease, atherosclerosis, etc.). In another aspect, methods and compositions are provided for patients at increased risk of developing a thrombus after a medical procedure, such as cardiac surgery, vascular surgery, or percutaneous coronary interventions. In an embodiment, the methods and compositions of this invention are used in cardiopulmonary bypass surgery. The compositions in a method of the invention, can be administered before, during or after the medical procedure.

Other uses of the invention include coating (e.g covalent coating) of GAGs on amine containing surfaces such as central venous lines, cardiac catheterization, cardiopulmonary bypass circuits, dialysis circuits, or other external blood contacting instruments, as well as mechanical valves, stents or any in vivo prosthesis.

Method of Preparation

The novel compounds of this invention are prepared by a simple one step process, which provides for direct covalent attachment of the amine of an amine containing moiety (such as, but not limited to, amine containing oligo(poly)saccharides, amine containing lipids, proteins, nucleic acids and any amine containing xenobiotics) to a terminal aldose residue of a glycosaminoglycan. Preferably, the amine containing moiety is a protein possessing a desirable biological activity. The mild non-destructive methods provided herein allow for maximal retention of biological activity of the protein and allow direct linkage of the protein without the need for intermediate spacer groups.

The glycosaminoglycan to be conjugated is incubated with the amine-containing species at a pH suitable for imine formation between the amine and the terminal aldose or ketose residue of the glycosaminoglycan. Terminal aldose and ketose residues generally exist as an equilibrium between the ring closed cyclic hemiacetal or hemiketal form and the corresponding ring opened aldehyde or ketone equivalents. Generally, amines are capable of reacting with the ring opened form to produce an imine (Schiff base). Typically, the aldoses are more reactive because the corresponding aldehydes of the ring open form are more reactive towards amines. Therefore, covalent conjugate formation between amines and terminal aldose residues of glycosaminoglycans provides a preferred method of attaching a species containing an amine to a glycosaminoglycan.

The reaction is typically carried out at a pH of about 4.5 to about 9, preferably at about 5 to about 8 and more preferably about 7 to about 8. The reaction is generally done in aqueous media. However, organic media, especially polar hydrophilic organic solvents such as alcohols, ethers and formamides and the like may be employed in proportions of up to about 40% to increase solubility of the reactants, if necessary. Non-nucleophilic buffers such as phosphate, acetate, bicarbonate and the like may also be employed.

Optionally and preferably, the imines formed by condensation of the amines of the first species with the terminal aldose residues of the glycosaminoglycans are reduced to the corresponding amines. This reduction may be accomplished concurrently with imine formation or subsequently. A wide array of reducing agents may be used, with hydride reducing agents, such as for example, sodium borohydride or sodium cyanoborohydride being preferred. Generally, any reducing agent that does not reduce disulfide bonds can be used.

Alternatively, if reduction of the intermediate imine is not desired, the imine may be incubated for a sufficient period of time, typically about 1 day to 1 month, more typically about 3 days to 2 weeks, to allow Amadori rearrangement of the intermediate imine. The terminal aldose residues of the glycosaminoglycans conjugated by the methods provided by this invention frequently possess C2 hydroxy groups on the terminal aldose residue, i.e., a 2-hydroxy carbonyl moiety which is converted to a 2-hydroxy imine by condensation with the amine of the species being conjugated to the glycosaminoglycan. In the Amadori rearrangement, which is particularly common in carbohydrates, the α-hydroxy imine (imine at C1, hydroxy at C2) formed by the initial condensation may rearrange to form an (α-keto amine by enolization and re-protonation (keto at C2, amine at C1). The resulting α-carbonyl amine is thermodynamically favored over the precursor α-hydroxy imine, thus providing a stable adduct with minimal disruption of the glycosaminoglycan chain. Thus in this embodiment, the invention provides a glycosaminoglycan covalently conjugated at the C1 of the terminal aldose residue of the glycosaminoglycan to an amine containing species via an amine linkage. If desired, the resulting conjugate may be reduced or labelled by reduction of the C2 carbonyl group with a labelling reagent, such a radiolabel (e.g., NaB$^3$H$_4$), [see, M. W. C. Hatton, L. R. Berry et al. (1980) Analytical Biochemistry 106:417–426], or conjugated to a second amine containing species, such as a fluorescent label.

A variety of different amine containing species may be conjugated to the glycosaminoglycans by the methods disclosed herein. Therefore, this invention provides covalent conjugates of glycosaminoglycans and a variety of other species. The primary amine may be on a small molecule, such as, for example, a drug or fluorescent or chromophoric label or a macromolecule such as, for example, a protein (antibodies, enzymes, receptors, growth factors and the like), a polynucleotide (DNA, RNA and mixed polymers thereof) or a polysaccharide. Generally, when proteins are being conjugated to glycosaminoglycans, linkage will occur through the å-amino groups of lysine residues. Alternatively, linkage may also be accomplished via the N-terminal amine by using a pH at which the å-amino groups are protonated. In addition, many methods are known to one of skill in the art to introduce an amine functionality into a macromolecule, see, e.g., "Chemistry of Protein Conjugation and Crosslinking", by S. Wong (CRC Press, 1991) and "The Organic Chemistry of Biological Compounds", by Robert Barker (Prentice-Hall, 1971).

In particular, the present invention can be applied to a variety of other therapeutically useful proteins where longer half-life and blood coagulation considerations are important. These include blood enzymes, antibodies, hormones and the like as well as related plasminogen activators such as streptokinase and derivatives thereof. In particular, this invention provides conjugates of heparin or dermatan sulfate with antithrombin, heparin cofactor II or analogs of heparin cofactor II, described in U.S. Pat. No. 5,118,793, incorporated by reference.

Alternatively, the amine containing species may be on a solid surface, such as polyethylene, polypropylene, cellulose, nitrocellulose, nylon, glass, glass fibers, plastic, diatomaceous earth, ceramics, metals, polycarbonate, polyurethane, polyester and the like. The surface may be a porous or semiporous matrix, a gel or a viscous liquid such as, for example, commonly found in chromatographic support media such as agarose, sepharose gels, beads and the like. Such supports with glycosaminoglycans, particularly heparin and its analogs, conjugated thereto are useful in a variety of applications such as affinity chromatography, bioseparations and solid phase binding assays. In particular, the use of heparin functional supports to purify antithrombin III is known and reported in U.S. Pat. No. 3,842,061, incorporated by reference. Numerous such amine containing solid supports and methods of derivatizing such supports to incorporate reactive amino groups therein are known to one of skill in the art. Thus, direct covalent conjugates of the terminal aldose residue of a glycosaminoglycan and any species, either known to exist presently or that may be available in the future, containing a reactive amino group are within the scope of this invention.

The methods of the present invention provide glycosaminoglycan conjugates with maximal retention of biological activity. In particular, conjugates of heparin or dermatan sulfate with either ATIII or HCII are provided which possess >60%, typically >90, more typically >95%, and most typically >98% of intact unconjugated heparin antithrombin activity. These conjugates have a bimolecular rate constant for thrombin inhibition of 5 to 100 fold higher, generally 8 to 20 fold higher, and typically almost 10 fold higher than the covalent conjugates reported by Collen.

The method of the present invention provides intact heparin molecules conjugated to antithrombin III or heparin cofactor II. Thus, loss of biological activity associated with fragmentation or other modification of heparin prior to conjugation is avoided. It will be apparent to one of skill in the art that the heparin conjugates of this invention retain their anticoagulant activity because of their preparation from intact heparin. Therefore, it is readily apparent that one may use the methods disclosed herein to prepare active heparin conjugates by first attaching linking groups and spacers to the species sought to be conjugated to heparin (or whatever the glycosaminoglycan being used) and subsequently attaching it to heparin. Numerous methods of incorporating reactive amino groups into other molecules and solid supports are described in the InmunoTechnology Catalog and Handbook, Pierce Chemical Company (1990), incorporated by reference. Thereby, any species possessing reactive amino groups or capable of being modified to contain such amino groups, by any method presently known or that becomes known in the future, may be covalently conjugated to glycosaminoglycans, such as heparin, by the methods disclosed herein and all such conjugates are contemplated by this invention.

As described above, the present invention takes advantage of the fact that native (isolated from intestinal mucosa) heparin, as well as dermatan sulfate, already contains molecules with aldose termini which would exist as an equilibrium between hemiacetal and aldehyde forms, a fact apparently unrecognized and unexploited in the art. Thus, we have conjugated heparin or dermatan sulfate to antithrombin serpins by reduction of the single, Schiff base formed spontaneously between the aldose terminus aldehyde on heparin or dermatan sulfate and a lysyl amino on the serpin. The heparin or dermatan sulfate is unmodified (unreduced in activities) prior to conjugation and is linked at one specific site at one end of the molecule without any unblocked activation groups or crosslinking of the serpin. Heparin has been covalently linked to ATIII or HCII and dermatan sulfate has been covalently linked to HCII. Conjugation of other GAGs (such as heparan sulfate) to serpins or other proteins (such as albumin) is possible by this method. For example, dermatan sulfate has been conjugated to albumin using the methods disclosed herein.

In another aspect of this invention we have also produced covalent complexes by simply mixing heparin and ATIII in buffer and allowing a keto-amine to spontaneously form by an Amadori rearrangement between the heparin aldose terminus and an ATIII lysyl amino group. Thus, this invention provides methods of using the Amadori rearrangement to prepare conjugates of glycosaminoglycans to amine containing species, particularly proteins. This is a particularly mild and simple method of conjugation, hitherto unrecognized in the art for conjugating such molecules, which minimizes the modification of the glycosaminoglycan, thus maximizing the retention of its biological activity.

Another aspect of this invention provides covalent conjugates of glycosaminoglycans, particularly of heparin, end-labelled with an amine containing species at the terminal aldose residue of the glycosaminoglycan. For example, heparin and ATIII are linked directly together so that the active pentasaccharide sequence for ATIII on the heparin is in close proximity for binding. This is one of the fundamental reasons for making a covalent heparin-ATIII complex, as heparin accelerates inhibition through ATIII only if ATIII can bind the active sequence. It is notable that ATH has the unique property that the H in the conjugate stoichiometrically activates the endogenous AT while catalytically activating exogenous AT. Typically, one amine containing species will be attached to each glycosaminoglycan. However, it will be apparent that the ratio of amine containing species to glycosaminoglycan may be reduced below one by adjusting the molar ratios of the reactants or the time of the reaction.

Glycosaminoglycans are available in a variety of forms and molecular weights. For example, heparin is a mucopolysaccharide, isolated from pig intestine or bovine lung and is heterogenous with respect to molecular size and chemical structure. It consists primarily of (1–4) linked 2-amino-2-dexoxy-α-D-gluopyranosyl, and α-L-idopyranosyluronic acid residues with a relatively small amount of β-D-glucopyranosyluronic acid residues. It contains material with a molecular weight ranging from about 6,000 to about 30,000. The hydroxyl and amine groups are derivatized to varying degrees by sulfation and acetylation.

Heparin molecules can also be classified on the basis of their pentasaccharide content. About one third of heparin contains chains with one copy of the unique pentasaccharide (see, Choay, Seminars in Thrombosis and Hemostasis 11:81–85 (1985) which is incorporated herein by reference) with high affinity for AT, whereas a much smaller proportion (estimated at about 1% of total heparin) consists of chains which contain more than one copy of the high affinity pentasaccharide (see, Rosenberg et al., Biochem. Biophys. Res. Comm. 86:1319–1324 (1979) which is incorporated herein by reference). The remainder (approx. 66%) of the heparin does not contain the pentasaccharide. Thus, so called "standard heparin" constitutes a mixture of the three species, "high affinity" heparin is enriched for species containing at least one copy of the pentasaccharide, and "very high affinity" heparin refers to the approximately 1% of molecules that contain more than one copy of the pentasaccharide. These three species can be separated from each other using routine chromatographic methods, such as chromatography over an antithrombin affinity column (e.g., Sepharose-AT; see, e.g., Lam et al., Biochem. Biophys. Res. Comm. 69:570–577 (1976) and Horner Biochem. J. 262: 953–958 (1989) which are incorporated herein by reference).

One advantage of forming a conjugate between heparin and a species containing at least one primary amino group (e.g., ATIII) using the slow glycation process disclosed herein, is the apparent selection for heparin chains having two pentasaccharides. Thus, for example, ATH prepared by the method of the invention appears to be enriched for heparin species containing two pentasaccharides. When standard heparin (containing approximately 1% of two-pentasaccharide heparin) is used as a starting material, usually more than 10% of the resulting ATH comprises two-pentasaccharide heparin, more often more than about 20%, frequently more than 35%, and often more than about 50% of the ATH comprises two-pentasaccharide heparin.

Without intending to be bound by any particular mechanism, one explanation for the apparent selection of very high affinity heparin is because the incubation mixture contains a 200-fold molar excess of heparin. During the incubation process, only heparin chains containing high affinity pentasaccharides close to a terminal aldose bind to the AT for a sufficiently long period of time to allow covalent attachment to occur. Therefore there is a selective interaction between AT and the very high affinity heparin chains.

This enrichment may account for several useful properties of ATH. The ATH of the invention activates the AT to which it is conjugated, in a stoichiometric fashion, but activates exogenous AT in a catalytic fashion. Thus, the heparin within the ATH complex acts catalytically both when ATH is administered as systemic anticoagulant and when ATH is used to coat surfaces to render them non-thrombogenic. The method of the invention produces an ATH complex with very high specific anti-factor IIa activity. In addition, the second pentasaccharide chain in the ATH complex can react with exogenous AT molecules, thereby allowing the conjugated heparin to have catalytic activity. Moreover, the heparin in the ATH complex can be orientated in such a way that the pentasaccharide is available to bind and activate circulating AT molecules when the ATH complex is bound to the prosthetic surface.

It will be appreciated that a heparin conjugate of interest (e.g., ATH) can also be produced by incubating a species containing at least one primary amino group (e.g., ATIII) with purified very high affinity heparin (i.e., containing two pentasaccharide groups) or a fraction enriched for very high affinity heparin.

Though this invention has been illustrated primarily with respect to heparin, it is apparent that all glycosaminoglycans, irrespective of their molecular weight and derivatization, may be conjugated by the methods disclosed herein, provided they possess a terminal aldose residue. Conjugates of all such glycosaminoglycans and their preparation by the methods disclosed herein are within the scope of this invention. For example, conjugates of heparin derivatized with phosphates, sulfonates and the like as well as glycosaminoglycans with molecular weights less than 6,000 or greater than 30,000 are within the scope of this invention.

Applications

In clinical practice, the novel heparin conjugates of the present invention may be used generally in the same manner and in the same form of pharmaceutical preparation as commercially available heparin for clinical use. Thus, the novel heparin conjugates provided by the present invention may be incorporated into aqueous solutions for injection (intravenous, subcutaneous and the like) or intravenous infusion or into ointment preparations for administration via the skin and mucous membranes. One skilled in the art will recognize that all forms of therapy, both prophylactic and curative, either currently known or available in the future, for which heparin therapy is indicated may be practiced with the novel heparin conjugates provided by this invention.

The heparin conjugates of this invention find particular utility in the treatment of neonatal and adult respiratory distress syndrome (RDS). In contrast to the use of noncovalent heparin-ATIII complexes, the use of the covalent heparin conjugates of the present invention prevents loss of heparin in the lung space by dissociation from ATIII. In this case, a solution of covalent complex in a physiologic buffer could be delivered as an atomized spray down the airway into the lung via a catheter or puffer. Due to its large size, ATH will remain in the alveoli for a longer period of time. ATH is also useful for treatment of idiopathic pulmonary fibrosis (more than two days).

Long term use in the circulation could be carried out by either intravenous or subcutaneous, preferably intravenous, injection of the complex in a physiologic buffer. The covalent conjugates of this invention may also be used in the treatment of acquired ATIII deficient states characterized by thrombotic complications such as cardiopulmonary bypass, extracorporeal molecular oxygenation, etc. because a longer ½ life of the covalent complex would mean fewer treatments and less monitoring. Additionally, this invention provides for prophylactic treatment of adult patients at risk for deep vein thrombosis.

The ATH conjugate of this invention has numerous advantages over uncomplexed AT and SH. Since AT is covalently linked to SH, non-specific binding of ATH to plasma proteins will be less than SH, resulting in less inter-individual variation in dose response to ATH than there is to SH. The longer half-life of ATH after intravenous injection in humans means that a sustained anticoagulant effect may be obtained by administering ATH less frequently than is required for uncomplexed AT and SH. ATH is a much more effective inactivator of thrombin and factor Xa than AT, and is expected to be effective when used in much lower concentrations than AT in patients with AT deficiency. In addition, ATH can access and inhibit thrombin bound to fibrin. Finally, when linked (e.g., covalently linked) to prosthetic surfaces (e.g., endovascular grafts), ATH has shown much greater antithrombotic activity in vivo than covalently linked AT or covalently linked hirudin.

Premature infants have a high incidence of respiratory distress syndrome (RDS), a severe lung disease requiring treatment with assisted ventilation. Long term assisted ventilation leads to the onset of bronchopulmonary dysplasia (BPD) as a result of lung injury which allows plasma coagulation proteins to move into the alveolar spaces of the lung. This results in the generation of thrombin and subsequently fibrin. The widespread presence of fibrin within the lung tissue and airspaces is consistently observed in infants dying of RDS. This fibrin gel within the airspace impairs fluid transport out of the lung airspaces resulting in persistent and worsening pulmonary edema. This invention provides novel therapies for the treatment of such fibrin-mediated diseases in lung tissue by preventing intra-alveolar fibrin formation by maintaining an "anti-thrombotic environment" and/or enhancing fibrinolysis within lung tissue, thereby decreasing the fibrin load to the air spaces of the lung.

The heparin conjugates will be delivered directly to the airspaces of the lung via the airway prophylactically (before the baby takes its first breath). This ensures that the antithrombotic agent is available directly at the site of potential fibrin deposition and that the bleeding risk associated with systemic antithrombotic therapies is avoided. In addition, the antithrombotic agent will already be present in the lung prior to the start of the ventilatory support which is associated with the initial injury, i.e., unlike systemic antithrombin administration where crossing of the administered drug to the lung airspace does not occur until after lung injury. Since heparin is covalently attached to ATIII it will remain in the lung airspaces. It can also be an adjunctive therapy to the surfactants currently administered to prevent RDS and BPD. By "lung surfactant" is meant the soap-like substance normally present in the lung's airspaces whose main role is to prevent collapse of the airspace. The conjugates can also be delivered repeatedly via the endotracheal tube or as an inhaled aerosol. Adjunctive therapy can also be practiced with asthma medications by inhaler (e.g., anti-inflammatory steroids such as beclomethasone dipropionate), other anti-asthmatics such as cromolyn sodium (disodium salt of 1,3-bis(2-carboxychromon-5-yloxy)-2-hydroxypropane, ("INTAL") and bronchodilators such as albuterol sulfate.

A variety of other diseases associated with elevated thrombin activity and/or fibrin deposition can be treated by administration of the conjugates of this invention. The inflammatory processes involved in adult respiratory distress syndrome are fundamentally similar to neonatal RDS and can be treated by the antithrombotic therapy described. Spontaneous lung fibrosis has also been shown to have activation of the coagulation/fibrinolytic cascades in the lung airspaces. Fibrotic disease of the lung is often a side effect associated with cancer chemotherapy and the RDS antithrombotic administration of the covalent heparin conjugates of this invention can be administered prophylactically prior to cancer chemotherapy to prevent lung fibrosis. Administration is repeated after chemotherapy in order to ensure no fibrin formation. A decrease in antithrombin III activity and an increase in thrombin activity in sepsis is also well documented. Sepsis is the most common risk factor for developing adult RDS. Thus, the heparin conjugates of this invention can be used to reduce the mortality associated with septic shock.

The conjugates of this invention are administered at a therapeutically effective dosage, i.e., that amount which, when administered to a mammal in need thereof, is sufficient to effect treatment, as described above (for example, to reduce or otherwise treat thrombosis in the mammal, or to inactivate clot-bound thrombin, or to inhibit thrombus accretion). Administration of the active compounds and salts described herein can be via any of the accepted modes of administration for agents that serve similar utilities.

The level of the drug in a formulation can vary within the full range employed by those skilled in the art, e.g., from about 0.01 percent weight (% w) to about 99.99% w of the drug based on the total formulation and about 0.01% w to 99.99% w excipient. Preferably the drug is present at a level of about 10% w to about 70% w.

Generally, an acceptable daily dose is of about 0.001 to 50 mg per kilogram body weight of the recipient per day, preferably about 0.05 to 25 mg per kilogram body weight per day, and most preferably about 0.01 to 10 mg per kilogram body weight per day. Thus, for administration to a 70 kg person, the dosage range would be about 0.07 mg to 3.5 g per day, preferably about 3.5 mg to 1.75 g per day, and most preferably about 0.7 mg to 0.7 g per day depending upon the individuals and disease state being treated. Such use optimization is well within the ambit of those of ordinary skill in the art. In the case of ATH, the long half-life allows the compound to be administered less frequently than SH (e.g., once or twice weekly).

Administration can be via any accepted systemic or local route, for example, via parenteral, intravenous, nasal, bronchial inhalation (i.e., aerosol formulation), transdermal or topical routes, in the form of solid, semi-solid or liquid dosage forms, such as for example, tablets, suppositories, pills, capsules, powders, solutions, suspensions, aerosols, emulsions or the like, preferably in unit dosage forms suitable for simple administration of precise dosages. Administration by intravenous or subcutaneous infusion is usually preferred. Most usually, aqueous formulations will be used. The conjugate is formulated in a non-toxic, inert, pharmaceutically acceptable carrier medium, preferably at a pH of about 3–8, more preferably at a pH of about 6–8. Generally, the aqueous formulation will be compatible with the culture or perfusion medium. The compositions will include a conventional pharmaceutical carrier or excipient and a conjugate of the glycosaminoglycan, and in addition, may include other medicinal agents, pharmaceutical agents, carriers, adjuvants, etc. Carriers can be selected from the various oils, including those of petroleum, animal, vegetable or synthetic origin, for example, peanut oil, soybean oil, mineral oil, sesame oil, and the like. Water, saline, aqueous dextrose or mannitol, and glycols are preferred liquid carriers, particularly for injectable solutions. Suitable pharmaceutical carriers include starch, cellulose, talc, glucose, lactose, sucrose, gelatin, malt, rice, flour, chalk, silica gel, magnesium stearate, sodium stearate, glycerol monostearate, sodium chloride, dried skim milk, glycerol, propylene glycol, water, ethanol, and the like. Other suitable pharmaceutical carriers and their formulations are described in Remington's Pharmaceutical Sciences by E. W. Martin (1985).

If desired, the pharmaceutical composition to be administered may also contain minor amounts of non-toxic auxiliary substances such as wetting or emulsifying agents, pH buffering agents and the like, such as for example, sodium acetate, sorbitan monolaurate, triethanolamine oleate, etc.

The compounds of this invention are generally administered as a pharmaceutical composition which comprises a pharmaceutical excipient in combination with a conjugate of the glycosaminoglycan. The level of the conjugate in a formulation can vary within the full range employed by those skilled in the art, e.g., from about 0.01 percent weight (% w) to about 99.99% w of the drug based on the total formulation and about 0.01% w to 99.99% w excipient. Preferably, the formulation will be about 3.5 to 60% by weight of the pharmaceutically active compound, with the rest being suitable pharmaceutical excipients.

The compounds of the invention, particularly ATH, can be used to reduce the thrombogenicity of internal and extracorporal devices that contact blood, and find special use for coating thrombogenic prosthetic surfaces and medical devices. As used herein, "prosthetic devices" and "medical devices" refers to any natural or synthetic material that is implanted into a patient or otherwise comes into contact with blood and for which it would be desirable to reduce blood coagulation. Thus, these terms encompass endovascular tubing, arterial and central venous lines, cardiac catheters, dialysis catheters, cardiopulmonary bypass circuits, dialysis circuits, or other external blood contacting instruments, as well as pacemaker leads, arterial and venous catheters for cannulation of large vessels thrombectomy catheters, sutures, blood filters, intravenous lines, mechanical valves, stents, artificial kidneys, lungs, hearts, and livers or any in vivo prosthesis, especially those made from a natural or synthetic polymer or polymers.

Materials used in prosthetic devices include Ioplex materials and other hydrogels such as those based on 2-hydroxyethyl methacrylate or acrylamide, and poly ether polyurethane ureas (PEUU) including Biomer (Ethicon Corp.) and Avcothane (Avco-Everrett Laboratories). The materials used most frequently for tubular applications are polyethylene, polypropylene, polytetrafluoroethylene (Gore-Tex), poly(vinylchloride), polydimethylsiloxane, an ethylene-acrylic acid copolymer, knitted or woven Dacron, polyester-polyurethane, polyurethane, polycarbonate-polyurethane (Corethane), polyamide (Nylon) and polystyrene. Additional compounds used in prosthetics and biomedical devices which come into blood contact are described in Kirk-Othmer Encyclopedia of Chemical Technology, 3rd Edition 1982 (Vol. 19, pp. 275–313, and Vol. 18, pp. 219–2220) and van der Giessen et al., Circulation 94:1690–1997 (1996) both of which are incorporated herein by reference.

In general, the composition of the invention, e.g., ATH, will be covalently attached to the polymer of the device. Methods for covalent attachment are well known and will vary depending on the nature of the polymeric material. In general, see Hermanson, Mallia and Smith, Immobilized Affinity Ligand Techniques, Academic Press (1992). It will be appreciated that other polymers and materials, possibly including some not yet discovered, will be suitable for linkage to ATH or other conjugates of the invention.

In a preferred embodiment, a polyurethane-polycarbonate material is coated with ATH. This coating is carried out in three steps. First, the polymer is activated. Activation can be accomplished by treatment with an oxidant (e.g., sodium hypochlorite, NaOCl) or a reductant (e.g., Lithium Aluminum Hydride). Second, a monomer (allyl glycidyl ether) is grafted onto the surface by reacting the activated tubing with an initiator ($Na_2S_2O_4$) and a monomer (e.g., allyl glycidyl ether, acrolein, or another monomer with a functional group joined to an alkene) that can further react with the compounds of the invention, e.g., ATH. Third, the compound to be linked, (e.g., ATH or other anticoagulants that have groups, such as, an amino group, that can react with the functional group of the monomer) is linked to the monomer. One advantage of this method is that it does not involve any manipulation of ATH and does not alter its anticoagulant activity.

The conjugates of the invention are also useful as molecular weight standards for analysis of unknown samples.

Another aspect of the invention is the discovery that an Amadori rearrangement can occur spontaneously in vivo. For example, when heparin is injected into a patient, it can combine with endogenous AT to form ATH. The formation of ATH and/or HCD in vivo following heparin injection may explain, in part, some of the clinical observations of persistence of anticoagulant activity following cessation of therapy with heparin (De Swart et al., 1982, Blood 60:1251–58). Activated partial thromboplastin times (APTTs) in patients receiving heparin remain increased at higher values than expected, given heparin's plasma half life and the amount of drug injected. Anti-Factor Xa activity assays for heparin in humans given low molecular weight heparin intravenously still show significant plasma activity 8 h after administration of the drug has been discontinued (Dawes et al., 1986, Haemostasis 16:116–22).

The in vivo non-enzymatic glycation of proteins with polysaccharides most likely occurs where the two species are sequestered together, as the reaction is a time dependent and high local concentration requiring event. Potentially, any polysaccharide terminating in an aldose could undergo a spontaneous conjugation with accessible proteins. Thus, this discovery suggests that various naturally-occurring polysaccharides may become linked to protein by this mechanism. Liver glycogen is one example. Glycogen exists in both protein bound (e.g., glycogenin) and non protein bound forms (Butler et al., 1977, Carb. Res. 55:73–82). Protein-glycogen complexes can form by initial synthesis of a glucoside, from nucleoside sugar, using a transferase (glycogen initiator synthase). However, the present discovery suggests that alternative mechanisms involving Amadori rearrangement of aldose terminating glycogen molecules, or synthesis of glycogen from protein spontaneously glycated with maltose (or higher oligoglucosides), may also occur.

The spontaneous modification of a polysaccharide, by covalent linkage to a polypetide, would significantly change its properties. Even small amounts of these altered molecules may have important biological functions. Thus, it will useful to assay the levels of naturally occurring polysaccharide aldoses or levels of such polysaccharide-polypetide complexes, especially following administration to a patient of a compound comprising a polysaccharide terminating in an aldose, with an unsubstituted hydroxyl at $C_2$. For example, the level of ATH following heparin injection can be measured. Methods for assaying levels of a compound (e.g., ATH or other conjugates) are well known and include immunological methods such as radioimmune assays, ELISAs, and others. See, for example, Harlow and Lane, Antibodies: A Laboratory Manual, Cold Spring Harbor, N.Y. (1988) which is incorporated herein by reference.

The following examples are given to enable those of skill in the art to more clearly understand and practice the invention. They should not be considered as limiting the scope of the invention, but merely illustrative and representative thereof.

EXAMPLES

Materials

In the following methodology, unless otherwise noted, "Standard heparin" refers to heparin from commercial sources. High affinity heparin is a heparin fraction in which all of the molecules bind to ATIII.

Heparin was from porcine intestinal mucosa (Sigma Chem Co U.S.A.). Dermatan sulfate was from porcine intestinal mucosa (Mediolanum farmaceutici S.p.A., Italy). ATIII was from human plasma (Bayer Inc.) HCII was from human plasma (Affinity Biologicals).

Example I

Preparation of Covalent Conjugates Between GAGs and Serpins

Reactions to form covalent complexes between the glycosaminoglycan (GAG) and serpin, for example ATIII or HCII, involved incubation of GAG (5 mg–70 mg) with the serpin (0.5 mg–3 mg) in 1 mL of sterile filtered buffer (0.3M phosphate 1M NaCl, pH 8.0 or 0.02M phosphate 0.15M NaCl, pH 7.3) containing 0.5M sodium cyanoborohydride at 35° C. to 45° C., preferably 40° C., in a sealed plastic tube (polycarbonate, polypropylene, etc). Omitting the sodium cyanoborohydride allowed formation of covalent complexes via Amadori rearrangement which could be radiolabeled by later addition of tritium labelled sodium borohydride. Incubation times ranged from 3 days to 2 weeks. Purification of the covalent product was achieved by a variety of methods. Purification procedures are described in U.S. Pat. No. 5,308,617, U.S. Pat. No. 4,623,718 and FEBS Letters 143(1): 96–100, 1982, all incorporated by reference. Gel filtration on Sephadex G-200 using 2M NaCl produced a high molar mass fraction containing covalent complex that was essentially void of free serpin. This fraction was further purified by electrophoresis on a 7.5% polyacrylamide gel at pH 8.8 using nondenaturing conditions (no sodium dodecyl sulfate), cutting out the section of gel containing only complex and elution of the product from the cut up section of gel by incubation in buffer (3.0 g/L tris (hydroxymethyl) aminomethane 14.4 g/L glycine pH8.8) at 23 degrees C.

Alternatively, the antithrombin-heparin conjugate (ATH) was also purified in one step from the reaction mixture by hydrophobic chromatography on butyl-agarose (Sigma Chemical Company, Milwaukee, Wis.). In 2.5M ammonium sulfate, ATH and ATIII bound to butyl-agarose beads while heparin did not. Adjusting the ammonium sulfate concentration from 2.5M to 1.8M allowed pure ATH to be eluted from the beads while ATIII remained bound.

Also, ATH and ATIII bound to butyl-agarose could be eluted together by adjusting the ammonium sulfate concentration to less than 1.5M followed by separation of the ATH from ATIII on DEAE Sepharose Fast Flow beads (Pharmacia Biotech, Uppsala Sweden). ATH and ATIII eluted from butyl-agarose were dialyzed versus 0.01M Tris-HCl pH 8.0 buffer prior to binding to the DEAE beads and the bound ATIII eluted with 0.2M NaCl in buffer while ATH was eluted by NaCl concentrations of 0.4M to 2.0M. In this way, ATH of different molecular weights and charges could be isolated, depending on the NaCl concentration used. Concentration of the purified ATH was done at 4° C. by dialysis in tubing, with a 12000–14000 molar mass cut off, under nitrogen pressure (1 atmosphere).

ATH produced in 0.02M phosphate, 0.15M NaCl, 0.05M sodium cyanoborohydride pH 7.3 and purified using elution of the complex from a cut out section of gel following nondenaturing electrophoresis, yielded material in which the molar ratio of ATIII:H in the complex was 1:1.1 and >99% was active.

Example II

Characterization of GAG-Serpin Conjugates

Biological Activity. Anti-Xa activity measured by Collen et al. and Bjork et al. for their respective preparations was carried out by (pre)incubation of the preparations with Xa followed by determination of residual activity of Xa with S-2222 (N-benzoyl-isoleucyl-glutamyl-glycyl-arginyl-paranitroanilide (from Chromogenix, Sweden)). The percent of conjugate molecules with activity (as determined by amount of Xa inhibited) is reported in Table 1. Anti-IIa activity was measured for the antithrombin-heparin conjugate of the invention (i.e. ATH) by titration with different amounts of IIa (thrombin). The amount of IIa inhibited by a given mass concentration of ATH (mass determined by analysis using unmodified starting heparin) was determined by measuring residual activity against S-2238 (D-phenylalanyl-pipecolyl-arginyl-paranitroanilide (from Chromogenix, Sweden)).

Inhibition of Thrombin Activity. The inhibition of the reaction of bovine thrombin with the chromogenic substrate S-2238 was studied. All operations were carried out at 23° C. Thrombin was added, with mixing, to a solution containing the material to be tested and S-2238 dissolved in 0.036M sodium acetate 0.036M sodium barbital, 0.145M NaCl pH 7.4 buffer in an eppendorf tube (the final thrombin concentration was 0.045 I.U./ml and the final S-2238 concentration was 28.3 µg/ml). The resultant solution was transferred to a quartz cuvette and absorbance readings at 405 nm taken over time (zero time being 30 sec after addition of the thrombin). The reaction concentration of the ATIII in either the ATH, ATIII or ATIII+H (heparin) reactions was 8.8 nM. The [ATIII] in the 0.3×ATH and 3×AT+H reactions was 2.7 nM and 27 nM, respectively. In reactions where heparin was used, it was present in equimolar concentrations to the ATIII in that experiment. The results are shown in FIG. 1 and show that the ATH conjugates of the present invention are more effective than free ATIII and heparin.

Thrombin was from Parke-Davis. S-2238 was from Chromogenix (Sweden). Standard Heparin (Leo Laboratories) was used.

Figure 2:
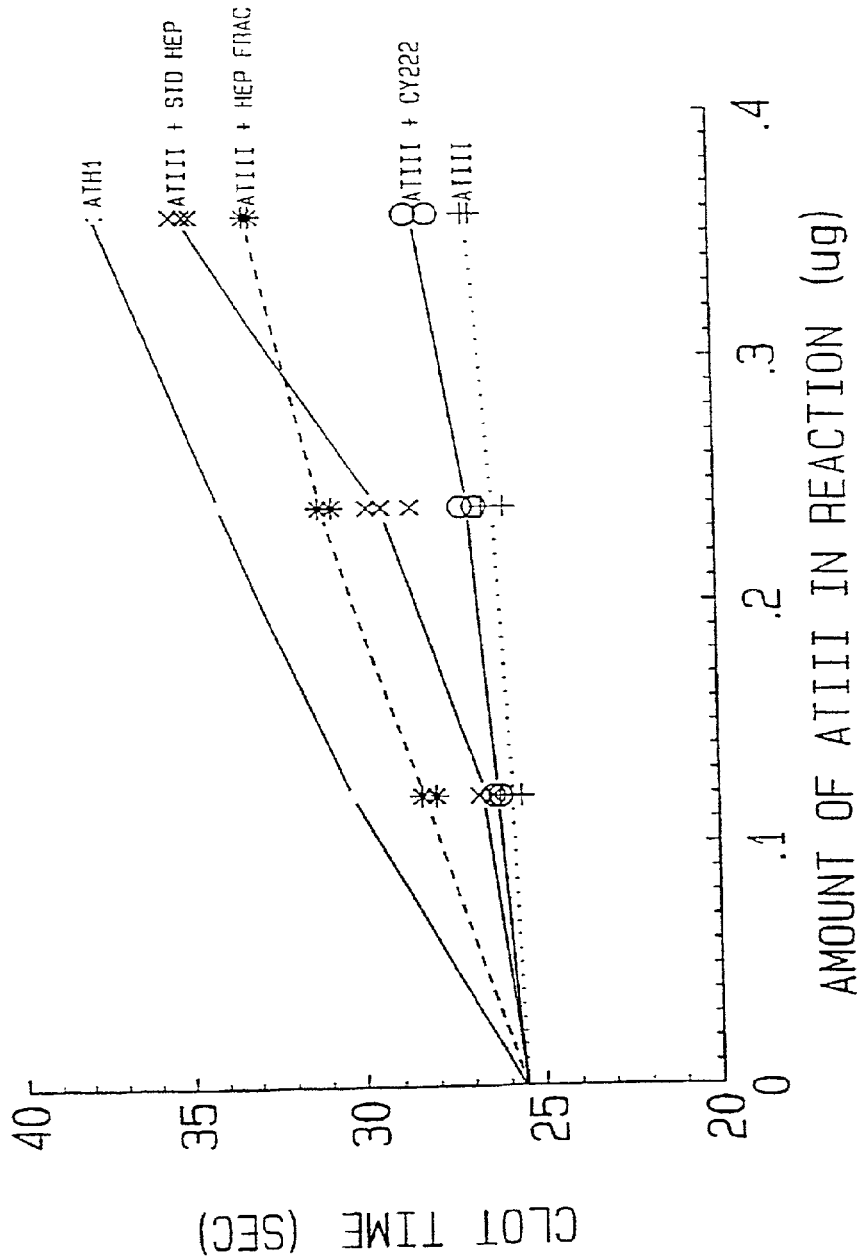
FIG. 2 shows the inhibition of the ability of thrombin to clot human fibrinogen by the covalent antithrombin III-heparin conjugates (ATH1) of the present invention.

Reaction with Fibrinogen and Thrombin. The ability of bovine thrombin to clot human fibrinogen was inhibited by various ATIII containing mixtures as follows. An ATIII containing sample was mixed with fibrinogen in 0.15M NaCl in a plastic tube at 37°C. After 1 min, thrombin was added (the final fibrinogen concentration was 0.2 mg/ml and the final thrombin concentration was 1 I.U./ml) and a clock was started. The time was recorded for the first appearance of a clot on the end of a nichrome wire loop used for agitation. The results are shown in FIG. 2 and show that the ATH conjugates are more effective at preventing clotting. The following abbreviations are used.

| | |
|---|---|
| ATH1 = | preparation #1 of ATIII-Heparin conjugate(as described in Example 1) |
| STD Hep = | standard heparin (LEO laboratories) |
| HEP FRAC = | low molecular weight fraction (≅7000 MW, produced by gel filtration) of standard heparin |
| CY222 = | low molecular weight heparin fragment produced by nitrous acid (average ≅ 2500 MW, produced by Choay Laboratories) |

Thrombin was from Parke-Davis; Fibrinogen was from Connaught Laboratories. ATIII was purified from human plasma. In ATIII+heparin mixtures, the protein and GAG content were equivalent on a mass basis (only 1 in 3 standard heparin molecules bind ATIII).

Effect of added Heparin on Rate of Inhibition of Thrombin Activity by Covalent ATIII-Heparin Conjugates (ATH)

Figure 3:
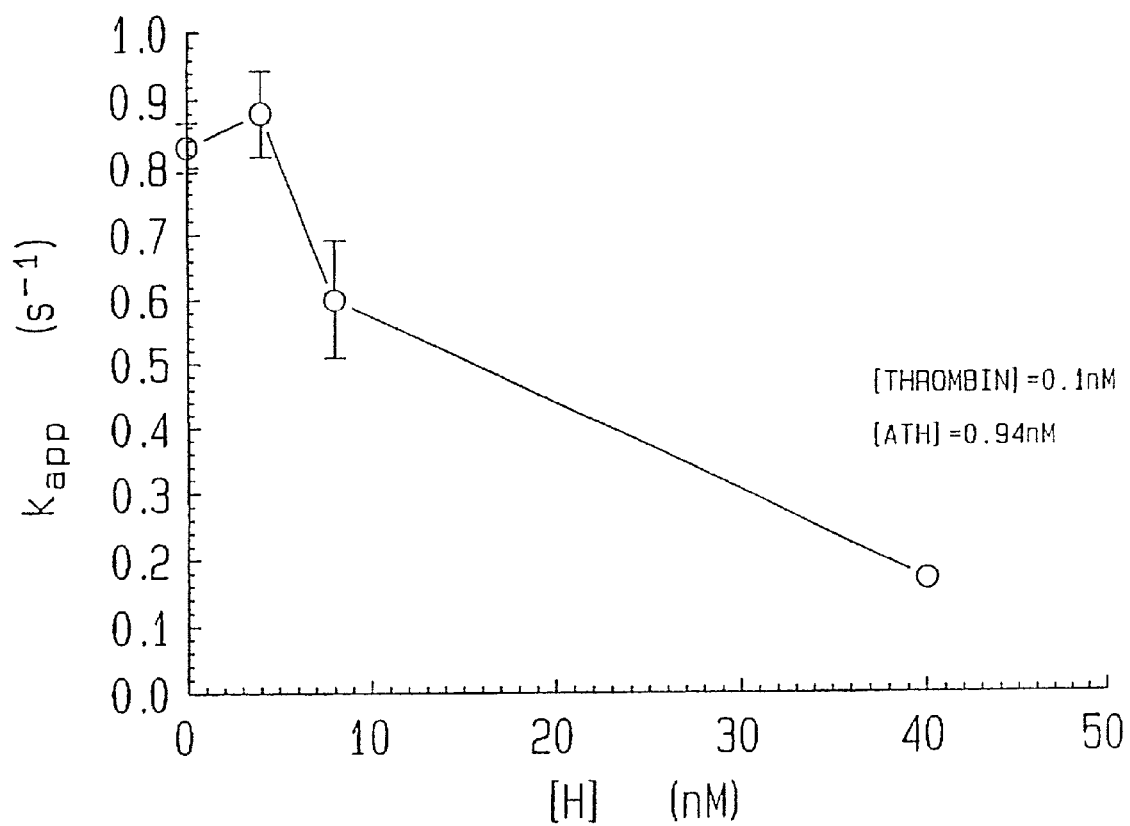
FIG. 3 shows the effect of added heparin on the rate of inhibition of thrombin by the antithrombin III-heparin conjugates of the present invention.

The ability of standard heparin to affect the inhibition of the human thrombin by ATH was tested. The buffer used was 0.1M Tris-HCl, 0.15M NaCl, 1.5 iM bovine albumin pH 7.6. ATH and varying amounts of heparin in buffer were placed in a 8 mm diameter, flat bottomed, polycarbonate, plastic tube equipped with a stirring bar rotating at 500–1000 rpm, all in a 37EC water bath. Human thrombin was added immediately as a clock was started. After a time ranging from 0.5 to 5 sec, thrombin inhibition was stopped by addition of a solution of excess polybrene and S-2238. Residual thrombin activity for S-2238 ($A_{405}$/min) was measured in a quartz cuvette at 37EC. The results are shown in FIG. 3. A semi-log plot of residual thrombin activity (Log ($A_{405} \times 10^4$/min)) versus time (sec) was constructed for each heparin concentration used. The apparent rate constant ($k_{app}$ ($S^{-1}$)) was calculated as ln 2 divided by the time at which ½ of the starting thrombin activity was inhibited. The $k_{app}$ for each heparin concentration is plotted.

Bovine albumin was from Sigma Chemical Company, Human thrombin was from Enzyme Research Laboratories (U.S.A.), S-2238 was from Chromogenix (Sweden) and heparin was from Leo Laboratories, Canada. All concentrations quoted on FIG. 3 are reaction concentrations just prior to polybrene-S-2388 addition.

Determination of Rates of Thrombin Inhibition by ATH

Figure 4:
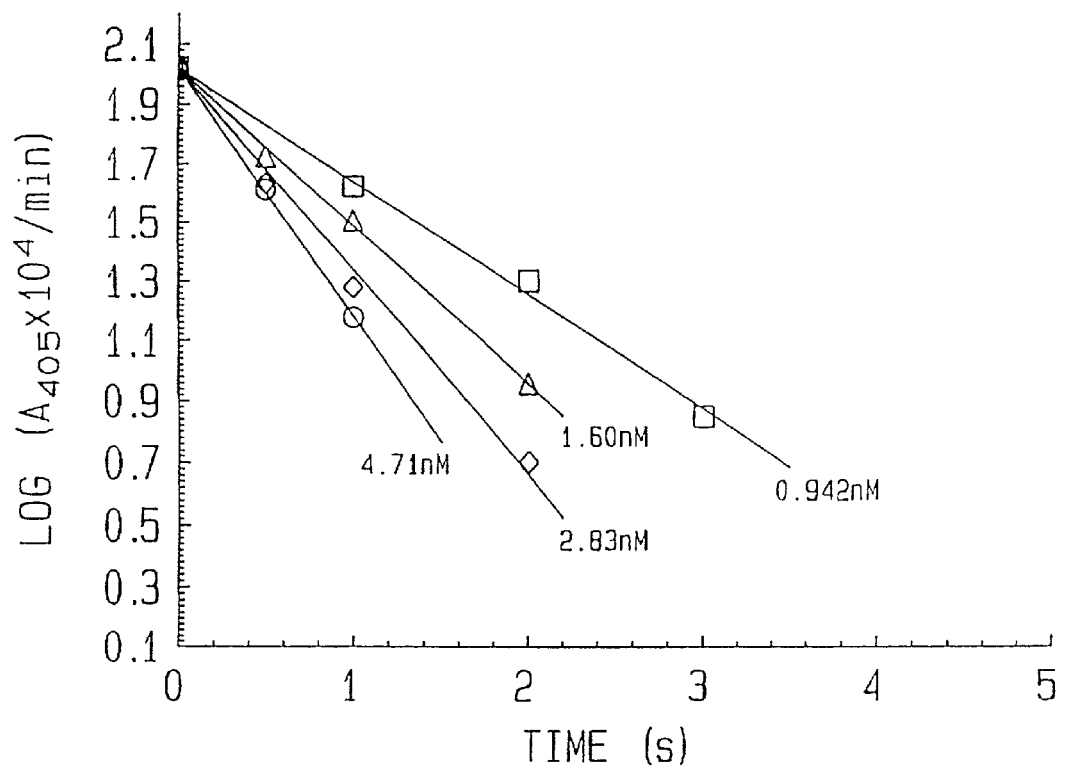
FIG. 4 shows the rate of inhibition of thrombin activity towards the chromogenic substrate S-2238 by the antithrombin III-heparin conjugates of the present invention.

The experimental procedure and calculation of the semi-log plot was the same as the experiments described above for FIG. 3 except that no exogenous heparin was added and the concentration of ATH was varied as shown. The results are shown in FIG. 4.

Inhibition of Thrombin+ATH reaction by FPR-Thrombin

Figure 5:
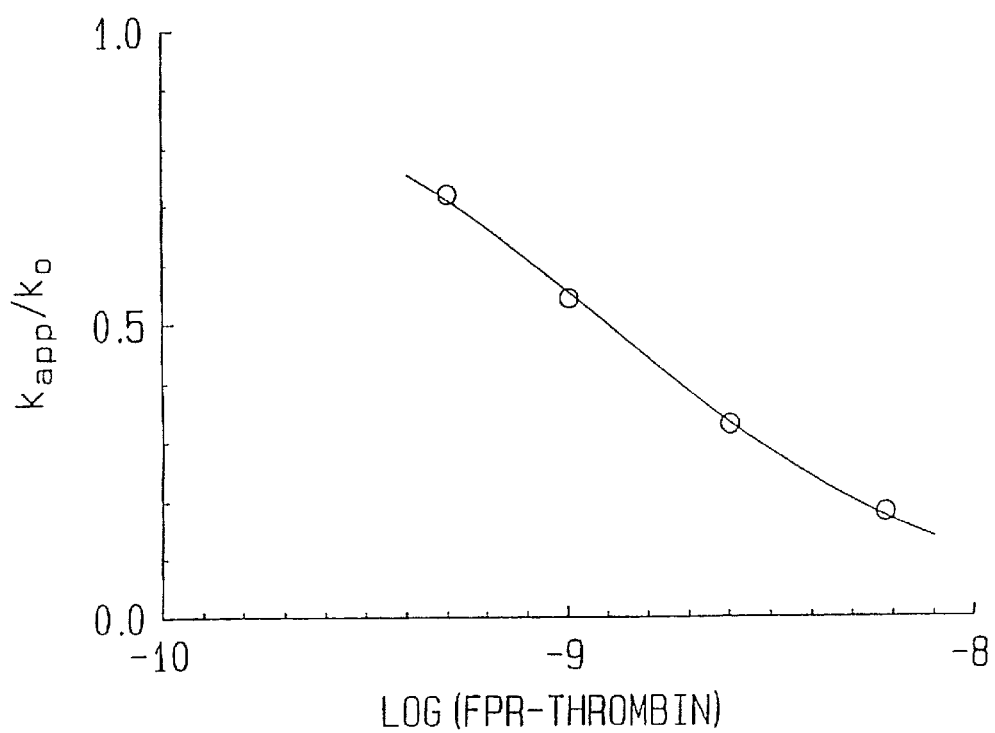
FIG. 5 shows the inhibition of the antithrombin effect of the covalent ATH conjugates of the present invention by FPR-thrombin.

FPR-thrombin is thrombin inhibited by phenylalanyl-prolyl-arginyl peptide covalently bonded to its active serine. FPR-thrombin can competitively inhibit the reaction of thrombin with ATH by binding to the heparin chain although it cannot react with the ATIII portion. The experimental procedure and calculation of kapp was the same as for the experiments for FIG. 3 except that varying amounts of FPR-thrombin were tested instead of heparin (no exogenous heparin added). The constant $k_o$ was the $k_{app}$ value with no FPR-Thrombin added. Results are shown in FIG. 5.

Bimolecular and 2nd Order Rate Constants and Effect of Added Heparin on Rate of Inhibition of Thrombin by ATH The procedure for the results for added heparin are given as determined from the results used for FIG. 3. To determine the rate constants, the method of Hoylaerts et al. in J. Biol. Chem. 259(9):5670–5677 (1984) was used. To calculate the bimolecular rate constant, $k_2$ and $K_i$ were determined as follows. The $k_{app}$ values for each curve for each ATH concentration used were determined for 3 separate experiments, of which FIG. 4 is a typical example. For each experiment, a plot of $1/k_{app}$ versus $1/$ [ATH] was constructed. The intercept of the $1/k_{app}$ axis was equal to $1/k_2$ and the intercept of the $1/$ [ATH] axis was equal to $1/K_i$. In each case, the bimolecular rate constant was calculated as $k_2/K_i$ and the average of 3 experiments is reported. For the second order rate constant ($k_1$), $k_1$(off rate), or $IC_{50}$ for FPR-thrombin competition ([FPR-Thrombin] at which $k_{app}/k_o$=0.5) was determined for each curve for each of 3 experiments, of which FIG. 5 is a typical example. The averages, for the three $k_2$ and $K_i$ values measured were used to calculate the second order rate constant for each $k_1$ value, given the following formula. Second order rate constant=$k_1$=$(k_1+k_2)/K_i$. The average is reported. Results are shown in Table 2. Error values are expressed as ±2 times the standard error of the mean.

Pharmacokinetics of Covalent ATIII-Heparin Conjugates

1. Plasma Clearance of ATH and Heparin After Intravenous Injection in Rabbits

Figure 6:
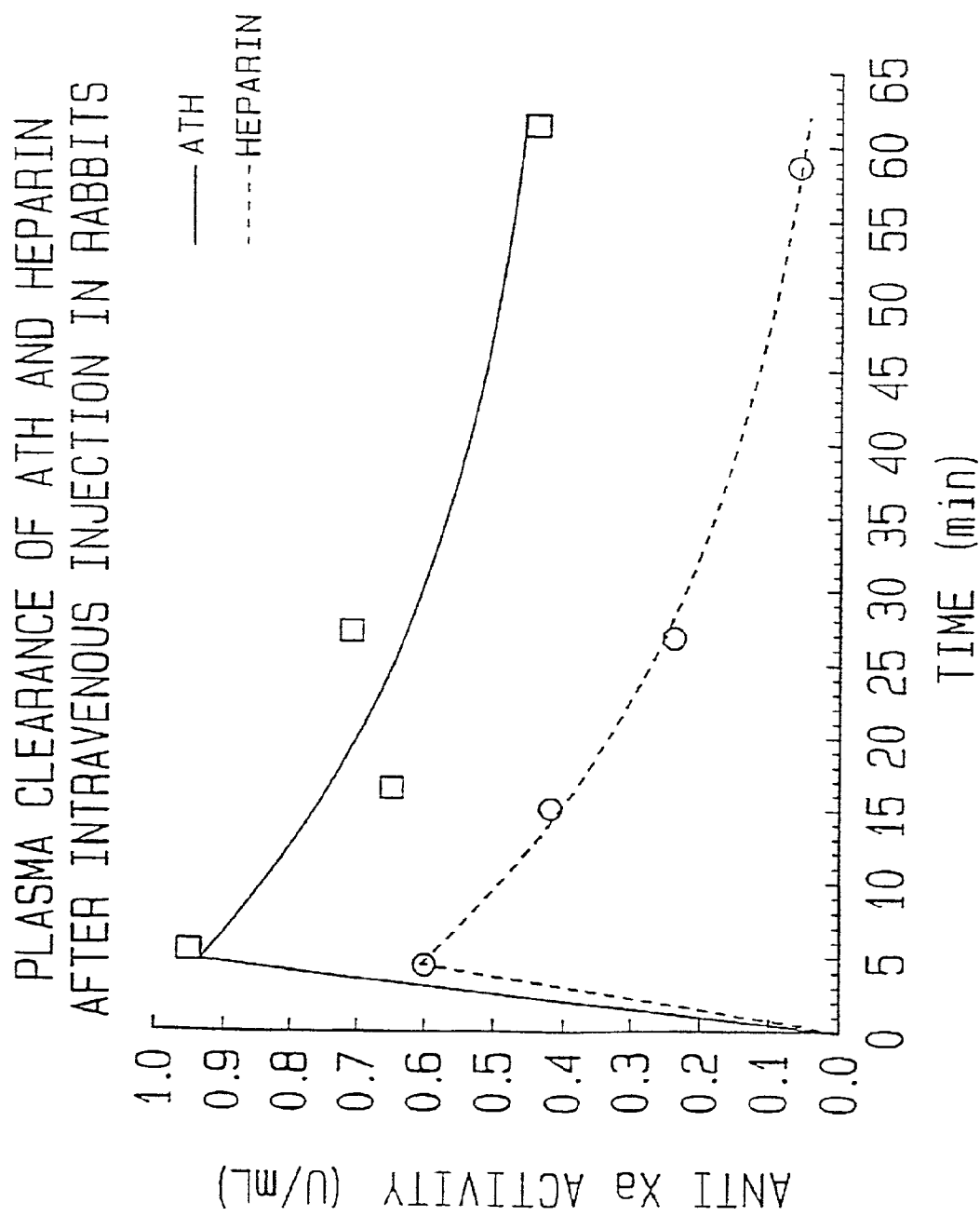
FIG. 6 shows the plasma clearance of the covalent ATH conjugates of the present invention and heparin in rabbits after intravenous injection.

Purified ATH and standard heparin (Sigma) were injected into the ear vein of separate rabbits. Equivalent amounts (by mass of heparin) were injected. At various times, blood samples were withdrawn from the ear artery of each rabbit into sodium citrate (9 parts blood to 1 part 3.8% (m/v) trisodium citrate). Each sample was centrifuged at 3000 g and the resultant plasma supernatants analyzed for anti-Xa activity using an ACL300 machine (Coulter U.S.A.) for automation. The procedure employed a Stachrom Heparin kit (Diagnostica Stago, France). Briefly, each sample of plasma to be tested was mixed with buffer containing bovine ATIII and incubated with bovine factor $X_a$ at 37° C. for 30 sec followed by a 30 sec incubation with the chromogenic substrate CBS 31.39 (N-(methylsulfone)-D-leucyl-glycyl-arginyl-paranitroanilide (from Diagnostica Stago, France)), after which the reaction was stopped by addition of acetic acid. The absorbance at 405 nm was then measured. A standard curve, generated using standard heparin, was used to determine the anti-$X_a$ activity in the plasma samples in terms of I.U./ml of heparin. Results are shown in FIG. 6. The ATH half life was observed to be 53 minutes and the free heparin half life was observed to be 17 minutes.

2. Pharmacokinetics in Plasma After Subcutaneous Injection in Rabbits.

Figure 7:
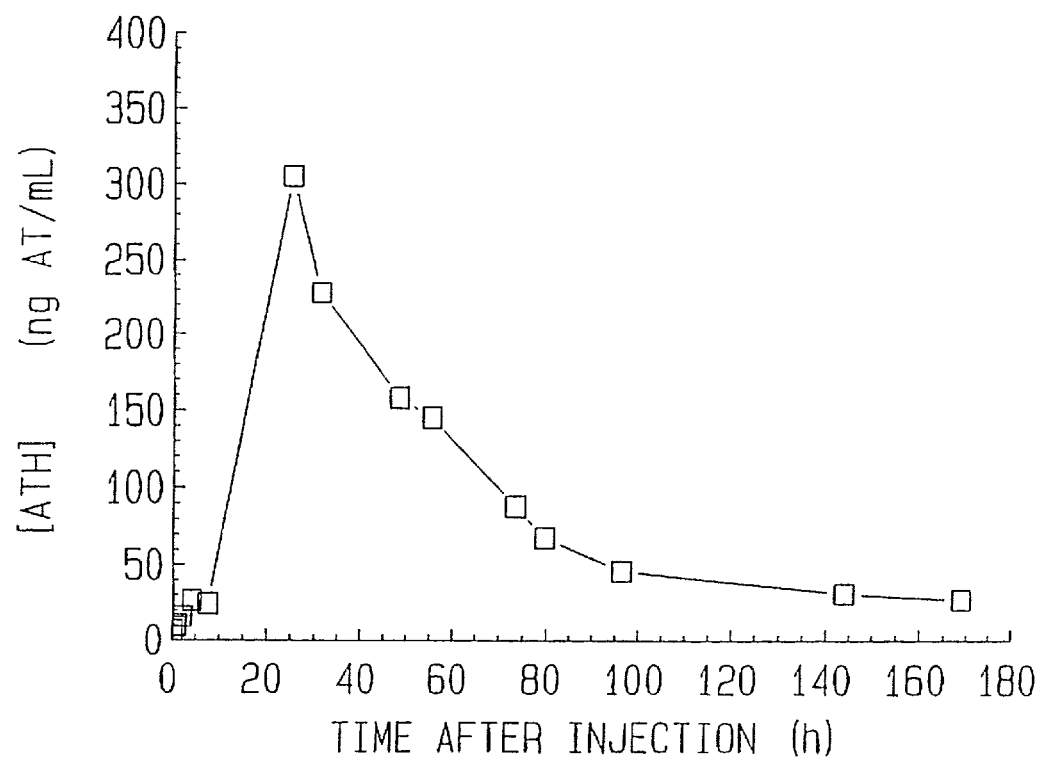
FIG. 7 shows the plasma concentrations of the covalent ATH conjugates of the present invention in rabbits after subcutaneous injection.
Figure 8:
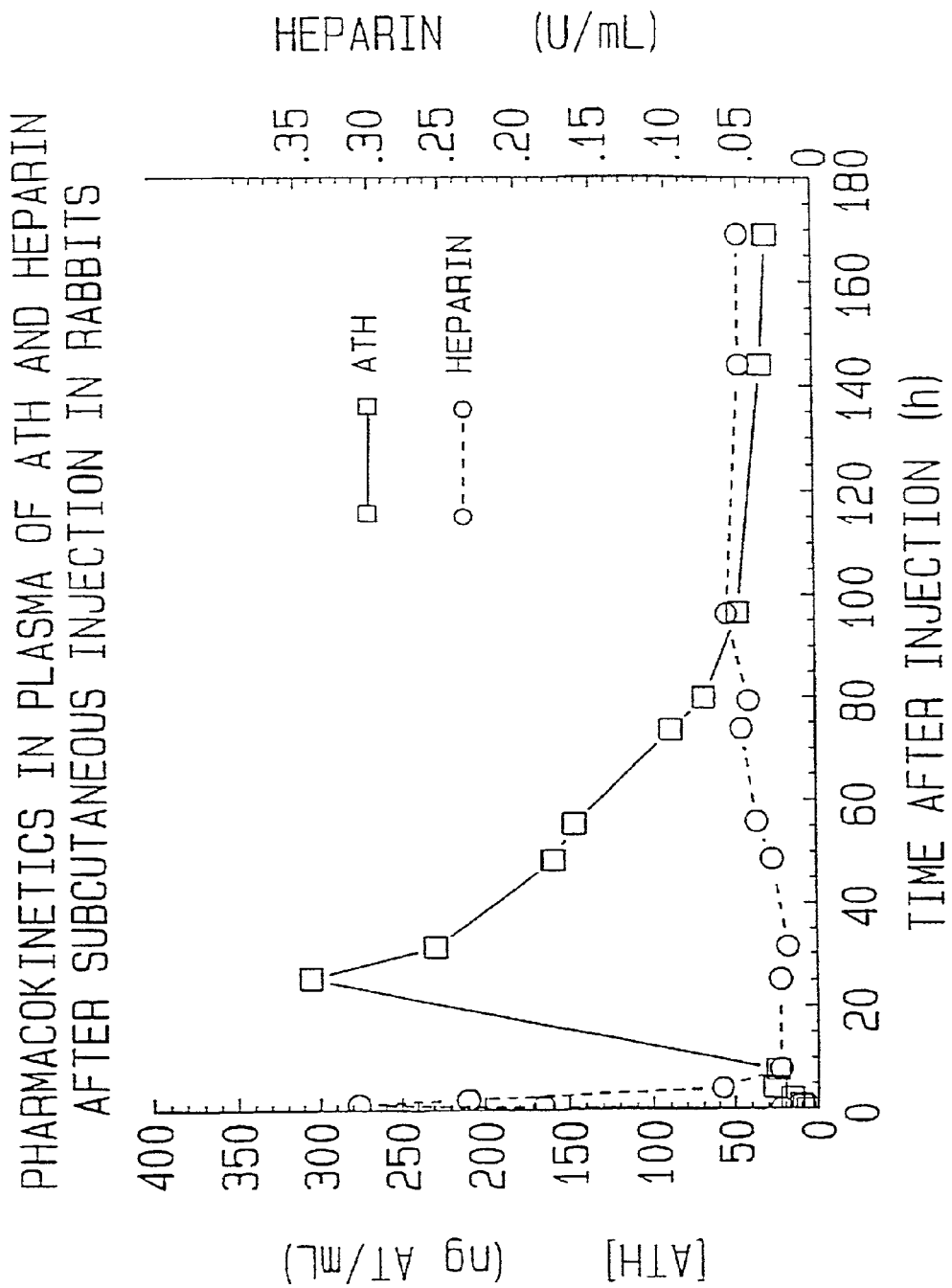
FIG. 8 shows the plasma concentrations of the covalent ATH conjugates of the present invention and heparin in rabbits after subcutaneous injection.

Rabbits were injected under the skin behind the neck and blood sampling for plasma analysis being done at various times as described above for FIG. 7. ATH was detected using an ELISA kit for ATIII from Affinity Biologicals (Hamilton, Canada). Briefly, ATH from sample plasmas was captured on plastic wells coated with sheep anti-human ATIII polyclonal antibodies. Peroxidase conjugated affinity purified anti-human ATIII antibodies (polyclonal) were applied to the wells and, after rinsing, color developed with $H_2O_2$/O-phenylenediamine substrate for 10 min. After terminating substrate reaction with $H_2SO_4$, the absorbance at 490 nm was measured. Standard curves of ATH or human ATIII in pooled normal rabbit plasma were used to determine the ng of human ATIII/ml. The rabbit's own ATIII did not interfere significantly, as the antibody used was selective for human ATIII. Results are shown in FIG. 8. In a separate experiment, when ATIII and heparin (noncovalent conjugate) was injected subcutaneously, ATIII (detected by ELISA) appeared in plasma with the same profile as ATH, but no heparin activity was observed.

2. Structural Characterization

A. General Structural Characteristics

The procedure to determine the molar ratio of Hep:AT in the heparin-antithrombin conjugates (ATH) was by densitometry of SDS gels (standard procedures) stained for either heparin (alcian blue/silver) or ATIII (Coomassie blue) compared with the corresponding standards. The activating groups per GAG molecule is by definition 1 (one aldose terminus per GAG chain).

The molecular weight range was determined from comparison of stained ATH, HCH, HCD with prestained standards on SDS polyacrylamide gels.

Characteristics of antithrombin-heparin conjugates(ATH) and heparin cofactor II-heparin (HCH) and heparin cofactor II-dermatan sulfate (HCD) conjugates are shown in Table 1.

B. Intrinsic Protein fluorescence of ATH

Figure 24:
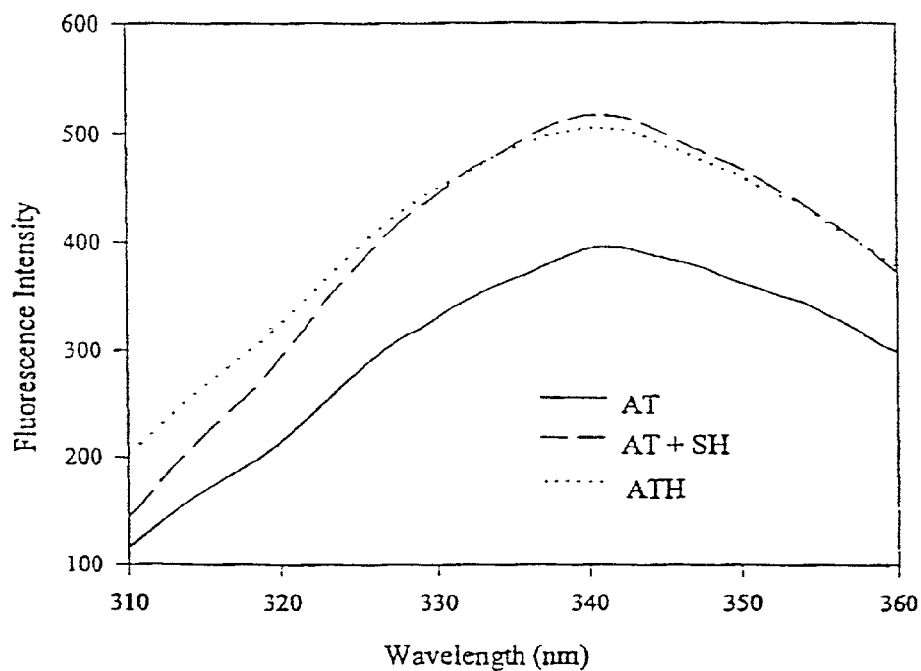
FIG. 24 shows protein fluorscence scans of AT, AT+SH, and ATH.

Since heparin is known to induce a ~33% enhancement in intrinsic protein fluorescence of AT (Huntington et al (1996) Biochemistry 35,8495–8503), the intrinsic fluorescence of ATH was compared to that of AT and AT+standard heparin (SH). The protein fluorescence emission spectra of 100 nM AT, 100 nM AT plus 1277 nM SH, or 100 nM ATH were recorded ($\lambda_{ex}$ 280 nm, $\lambda_{em}$ 310–360nm). The fluorescence of AT+H was 32% higher than that of AT alone at $\lambda_{max}$ (341 nm) with less than a 1 nm peak shift (FIG. 24). The spectrum of ATH was virtually identical to that of AT+SH. These data suggest that the conformation of ATH resembles that of the noncovalent AT–SH complex.

C. Heparin Titration of AT and ATH

Figure 25:
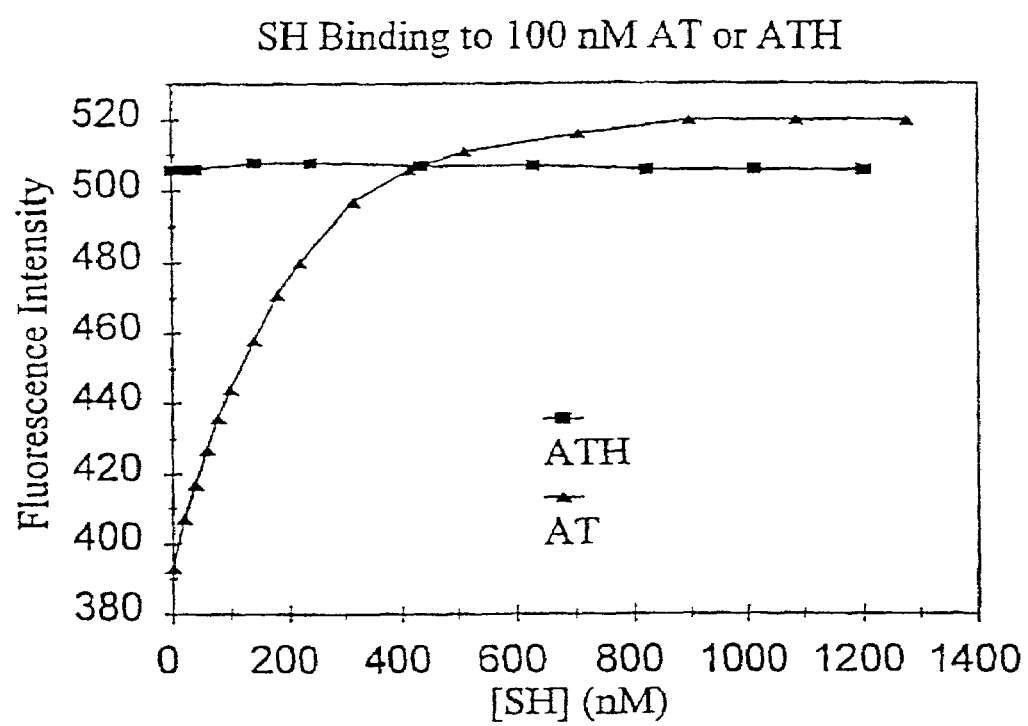
FIG. 25 shows SH binding to 100 nM AT or ATH.

A titration with SH was performed to determine whether ATH could undergo further conformational change (FIG. 25). Protein fluorescence values (at 341 nm) were determined during a SH titration of 100 nM AT and ATH. AT underwent a dose-dependent and saturable increase in fluorescent intensity that yielded a $K_d$ of 100 nM and a 32% maximal $\Delta$FI. In contrast, there was no increase in FI with SH titration of ATH indicating no further alteration in protein conformation. Therefore, ATH is in a fully activated conformation that is independent of exogenous SH.

D. AT Titration of ATH

Figure 26:
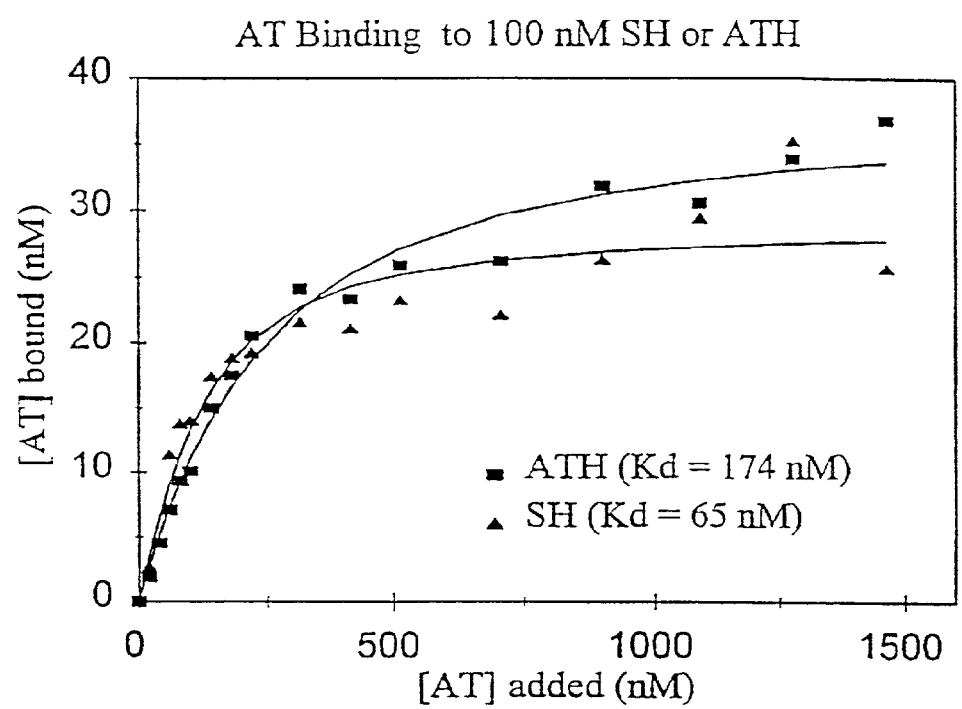
FIG. 26 shows AT binding to 100 nM SH or ATH.

In order to determine whether the heparin component of ATH was capable of binding additional AT, an AT titration of ATH was performed (FIG. 26). This was compared to an AT tritration of free SH. Protein fluorescence values (341 nm) of 100 nM ATH were determined in the presence of increasing amounts of AT. The values were corrected for inner filter effect such that a control AT titration was linear. The difference in fluorescent intensity values were converted to AT concentration using an extinction coefficient for AT+SH determined in these studies. Binding of AT to SH and to ATH was saturable with $K_d$ values of 65 and 175 nM, respectively. The results indicate that there is 28 nM SH bound to AT in 100 nM SH, suggesting ~28% pentasaccharide content in this SH preparation. ATH is able to bind ~37 nM AT, revealing a higher pentasaccharide content. These results reveal that the heparin component of ATH is capable of binding additional AT and, therefore, is able to act catalytically.

E. Protein Conformation of ATH Compared to AT+H

In a heparin titration, the protein conformation of ATH in the absence of SH, as measured by tryptophan fluorescence, is very similar to that of AT with saturating levels of SH (FIG. 25). Therefore, within experimental error, it appears that ATH resembles SH-activated AT. Furthermore, ATH does not undergo further conformational change when SH is added suggesting that no further activation occurs. Therefore, as expected, ATH represents a fully activated form of AT that does not require exogenous SH.

F. Binding by the H in ATH of Additional AT

When AT is added to ATH there is a further increase in protein fluorescence that is due to the intrinsic H within the ATH complex. The $K_d$ of binding reveals that the affinity of H (within ATH) for AT is slightly lower than that of free SH (FIG. 26). This probably reflects competition between the covalently attached and free AT molecules. The results suggest that about 30 nM AT can bind to 100 nM SH, suggesting a pentasaccharide content of ~30%. Although the ATH-mediated binding to AT revealed higher binding, the apparent pentasaccharide content was only about ⅓ higher (~40 nM binding to AT from 100 nM ATH). This is unexpected but may be due to the competition of the AT in ATH with the exogenous AT, or that ⅓ of ATH molecules have a second pentasaccharide on the H in ATH binding to the exogenous AT, or that of ATH molecules have a second pentasaccharide. These results suggest that the H within ATH is catalytic.

G. Selection for Heparin Molecules with Two Pentasaccharides in Formation of ATH When a fixed amount of heparin is titrated with AT and the fluorescence intensity is monitored, there is a saturable increase in fluorescence intensity that reflects heparin-induced conformational changes in the reactive center of AT. A similar increase in fluorescence intensity is observed when ATH is titrated with AT (FIG. 9).

Figure 9:
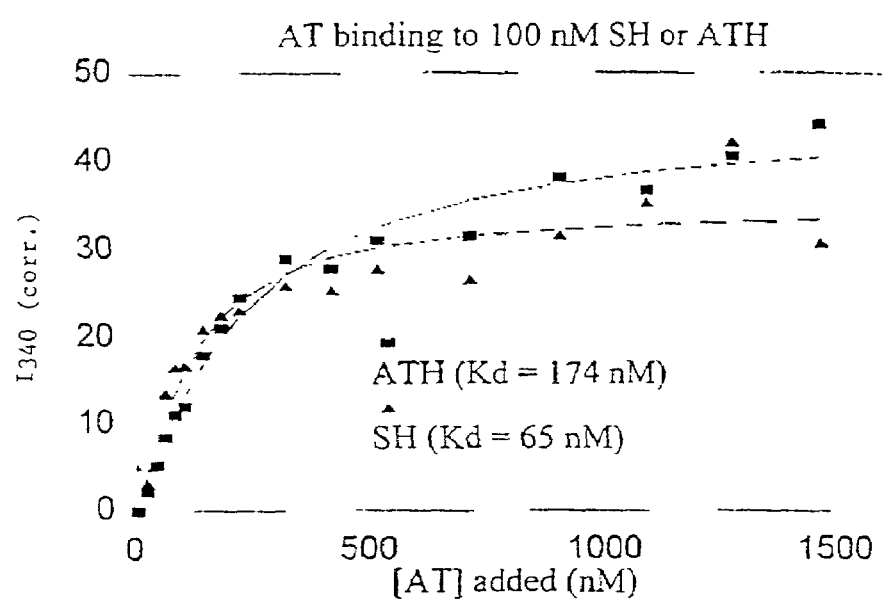
FIG. 9 shows AT binding to 100 nM SH or ATH.

The results summarized in FIG. 9, reflecting a change in fluorescence intensity that occurs when ATH is titrated with AT which is almost identical to that which occurs when heparin is titrated with AT, suggest the presence of a second pentasaccharide on the AT-conjugated heparin. This can be demonstrated by considering the result that would be expected if heparin having only one pentasaccharide were conjugated to the AT moiety of ATH. In that case, as the pentasaccharide disengaged itself from the AT to which the heparin is covalently bound, the AT would return to its native conformation, resulting in a decrease in fluorescence intensity. Once disengaged, the pentasaccharide could then bind an exogenous AT causing it to undergo a conformational change. This would be associated with a reciprocal increase in fluorescence intensity back to the starting value. The net effect of this process would be no change in fluorescence intensity, contrary to what is observed in this experiment.

Example III

Production and Purification of ATH

Human AT (Bayer Inc.) and SH (Sigma Chem. Co. U.S.A.) were initially dialysed to ensure purity of the reagents. Human AT and SH were incubated together in a 40° C. water bath for 10–14 days. This incubation allowed the conjugation of heparin to AT by Schiff base formation between the aldose terminus aldehyde on heparin and a lysyl amino on the AT, followed by an Amadori rearrangement or reduction by sodium cyanoborohydride (final concentration 0.05M) for 5 h after the initial reaction. The sodium cyanoborohydride was added to the mixture after the incubation period. This production process is simple and does not require any structural changes to either compound.

ATH was purified using two chromatographic steps.

The first step involves adding the reaction mixture to a hydrophobic-containing matrix, butyl-agarose, in 2.5 M ammonium sulphate. Under these conditions, free AT and ATH bind to butyl-agarose beads while heparin does not. AT and ATH are than eluted off the beads by adjusting the ammonium sulphate concentration to less than 1.5 M. The ATH and AT that are eluted off the butyl-agarose matrix are then dialysed against 0.01 M Tris-HCl pH 8.0 buffer.

The second step involves applying the eluted ATH and AT onto DEAE Sepharose Fast Flow Beads in 0.2 M NaCl. Under these conditions, free AT does not bind to the DEAE Sepharose Beads. ATH is then eluted off the DEAE beads by adjusting the NaCl concentration to 2 M. The purified ATH is then concentrated by pressure dialysis at 4° C. under 1 atmosphere of nitrogen pressure in tubing with a 12000–14000 molar mass cut-off.

Example IV

Stability of ATH

ATH was stored at 4° C. and anti-factor Xa activity assays were performed on the compound on a regular basis over 3 months. Two anti-factor Xa activity assays were used. The first had no exogenous AT added while, in the second, exogenous AT was added. Table 3 shows that the ATH lost activity after about three months.

ATH has also been stored at −70° C., with no loss of activity after six months. ATH has also been lyophylized and reconstituted with water. Prior to freeze drying, ATH was dialysed against 0.1 M Alanine and 0.15 M NaCl pH 7.0. Reconstituted ATH was active, as assayed by anti-factor Xa activity, for at least 6months.

Example V

Biological Activities and Mechanisms of Action of ATH

1. Direct Non-Catalytic Activity

ATH has direct non-catalytic antithrombin activity as well as anti-factor Xa activity. Using a standard anti-factor Xa assay (Thrombosis Res. 10:399–410 (1977)) without exogenous AT added, ATH has a specific activity of 48 U/mg heparin.

Figure 10:
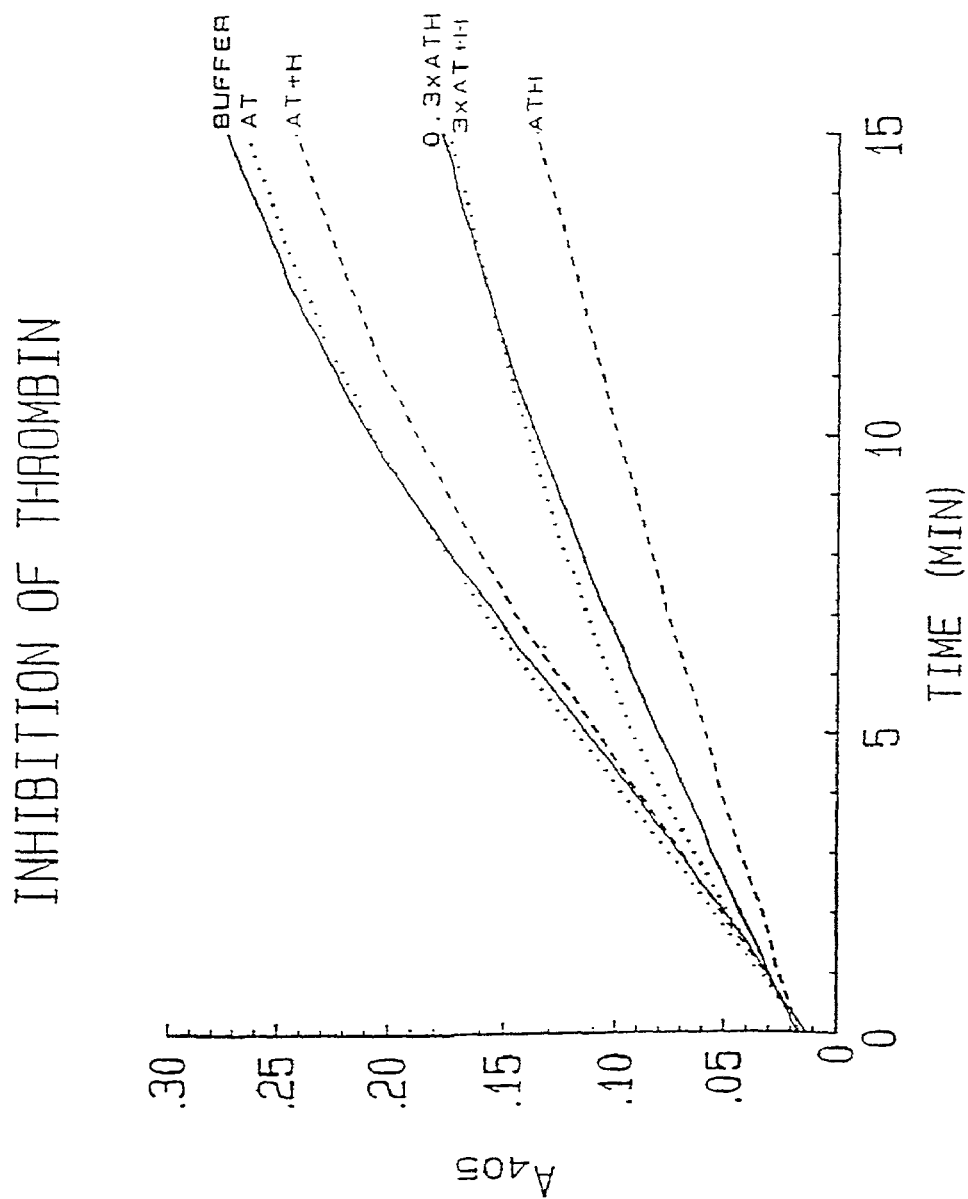
FIG. 10 shows the activity of ATH and AT+SH in inhibiting thrombin.

Inhibition of thrombin was studied by measuring the residual activity of thrombin using the chromogenic substrate S2238 (Thrombosis Res. 13:285–288 (1978)) after the enzyme had been reacted with ATH. The activity of ATH was compared to AT or AT+SH. The amounts of AT and or heparin used were equivalent by weight to the amounts of each used in the ATH. FIG. 10 shows that when the AT and heparin components are present in an equal mass, ATH is much more active than AT+SH in inhibiting thrombin.

2. Catalytic Activity

Figure 11:
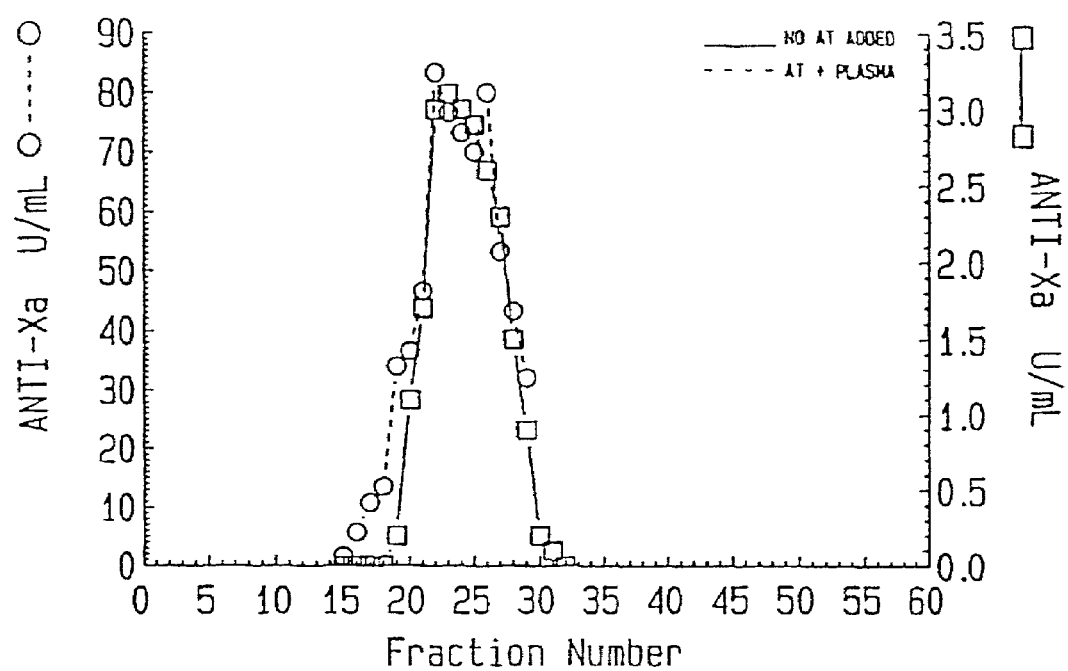
FIG. 11 shows noncatalytic [□---- □] and catalytic [○---- ○] activities in ATH after chromotography on Sephadex G200.

The anti-factor Xa activity of ATH without exogenous AT added to the assay system was 48 u/mg. For an equivalent amount of AT, there was no measurable activity. The anti-factor Xa activity of ATH with exogenous AT added to the assay system was 731 u/mg heparin, indicating that there was catalytic activity in the ATH. Since AT is covalently linked to H in the complex, the observation that the H in ATH could catalyze AT mediated inactivation of Xa is unexpected. To rule out the possibility that the observed catalytic effect of the ATH is due to contamination of ATH with free H, ATH was subjected to gel filtration over a G-200 column. The eluted fractions were then analyzed on a 4% stacking and 7.5% separating polyacrylamide gel which clearly separates ATH from heparin. The heparin in the ATH and in the free heparin fraction was detected by alcian blue staining followed by silver nitrate and the amount of heparin in the ATH and free heparin bands was quantified using densitometry and comparing the weights of paper cut out from the area under the curves. The data are summarized in Table 4 and FIG. 11.

A fraction was selected (fraction 22) which contained 0.100818 mg H/ml as ATH and 0.498200 µg H /ml as free heparin and was assayed for anti-factor Xa activity. The specific anti-factor Xa activity of this fraction was 83.25 U/ml. If this was accounted for only by the amount of ATH present in the fraction it would be equivalent to a specific activity of 825 U/mg. If the anti-factor Xa activity in the fraction was accounted for only by the free heparin in the fraction it would require the heparin to have a specific activity of 167101 U/mg. Since the specific anti-factor Xa activity of SH is about 160 U/mg, and the amount of free heparin in the fraction is less than 0.5 µg/ml, the results of this experiment indicate that almost all of the observed anti-factor Xa activity is accounted for by ATH. The specific anti-factor Xa in this fraction (fraction 22) was assayed in the presence and absence of exogenous AT. The activity was increased 25 to 30 fold in the presence of exogenous AT. Based on the very low concentration of free heparin (described above), this fold increase could only be explained by a catalytic effect of heparin in the ATH complex. To verify this point, anti-factor Xa assays were performed in the presence of exogenous AT using heparin (high affinity) in concentration of 0.5 (the amount of free heparin in the fraction) and 5 µg/ml. In both cases, there was no measurable anti-factor Xa activity. These findings indicate that the catalytic activity observed in the ATH could not be due to contaminating free heparin, and confirm that complexed heparin in ATH has catalytic activity. The ratio of catalytic to non catalytic activity was significantly greater in high molecular weight fractions compared to low molecular weight fractions. This suggests that a higher number of pentasaccharides (i.e., two or more pentasaccharides per molecule) are present in larger ATH molecules.

Without intending to be bound by any particular mechanism, there are two likely explanations for the observed catalytic effect of ATH.

The less likely is that when the AT component of ATH complex binds to thrombin, a conformational change occurs at the heparin binding site of AT, which results in a markedly reduced affinity for the heparin pentasaccharide. The pentasaccharide then dissociates from the AT (although the heparin molecule remains covalently linked to the AT) and is available to bind to exogenous AT.

More likely is the possibility that the process of covalent linkage of AT to heparin selects heparin molecules that contain two pentasaccharide units. Therefore, ATH can bind to AT and acts as a catalyst through the second pentasaccharide site.

In order to clarify the mechanisms responsible for the observed catalytic activity, the following experiments can be performed:

i) To differentiate between the two mechanisms, ATH will be passed over an AT column. If ATH binds to immobilized AT, it would imply that the second mechanism is responsible. In addition the anti-factor Xa activity of ATH would be expected to be decreased by heparinase treatment if a second pentasaccharide is responsible for the increased activity.

ii) If ATH does not bind to immobilized AT it would support the first suggested mechanism as the cause of the observed catalytic effect of heparin covalently bound to AT. To evaluate this mechanism, ATH will be titrated with thrombin before passing it over an AT column. Active site-inhibited thrombin (FPR-thrombin) will be used as a control, since it does not bind to the reactive center of AT and would therefore not be expected to reduce the affinity of AT to the pentasaccharide.

3. Inactivation of ATH by Protamine

The ability of protamine sulphate and of human platelet factor 4 (PF4) to inactivate the anticoagulant activity of ATH was determined. About 80% of the anti-factor Xa activity is inactivated by either protamine sulphate or PF4. Thus, ATH activity can be neutralized during use, if necessary.

4. Rate of Inhibition of Thrombin

The second order rate constants of ATH, AT alone and AT+SH, were compared, using the method of Hoylaerts et al. (J. Biol. Chem. 259(9):5670–5677). As shown in Table 5, ATH is about 30 times faster than AT+SH at inhibiting thrombin.

5. Effect of Fibrin on Thrombin Inactivation by ATH

Thrombin bound to fibrin remains catalytically active, dissociates very slowly from fibrin, and is protected from inactivation by AT and by AT and SH. The effect of ATH on fibrin bound thrombin was evaluated and the apparent k1 of the rate of thrombin inhibition by ATH in the presence of different concentrations of fibrin monomer determined by measurement of residual thrombin at various times during the reaction. Inhibition of thrombin is stopped at various times by addition of polybrene and the thrombin activity remaining is determined using the chromogenic substrate S-2238. The results are presented in Table 6. The rate of thrombin inhibition by ATH was unaffected by fibrin monomer. In contrast, fibrin monomer decreased the ability of high affinity heparin to inhibit thrombin by about 60 fold. These results indicate that ATH can inactivate thrombin bound to fibrin.

Fibrin-bound thrombin is resistant to inactivation by SH because the heparin binding site (exosite 2) on thrombin is masked when the enzyme is bound to fibrin. Since ATH can inactivate fibrin bound thrombin, experiments were preformed to determine whether exosite 2 is critical for inactivation of thrombin by ATH. These experiments were carried out using R93-thrombin, a recombinant thrombin with an inactive mutant exosite 2 (J. Biol. Chem. 269: 17965–17970 (1994)). As shown in Table 7, ATH inactivates R93-thrombin at the same apparent rate as alpha thrombin. In contrast to ATH, the kl of high affinity heparin is about 400 times higher for alpha thrombin than for R93-thrombin. These findings suggest that exosite 2 is not required for ATH to bind to thrombin.

Example VI

Pharmacokinetic Studies of ATH in Rabbits

The pharmacokinetics of ATH was studied in rabbits using anti-factor Xa assays and ELISAs for human AT. Pharmacokinetics of human AT+SH, SH alone and human AT alone in rabbits were studied for comparison with ATH.

1. Pharmacokinetics After Intravenous Administration in Rabbits

The amounts of each compound administered intravenously to rabbits were as described below. Anti-factor Xa activity was assayed by the method described in Thrombosis Res. 10:399–410 (1977). (See Table 8)

Figure 12:
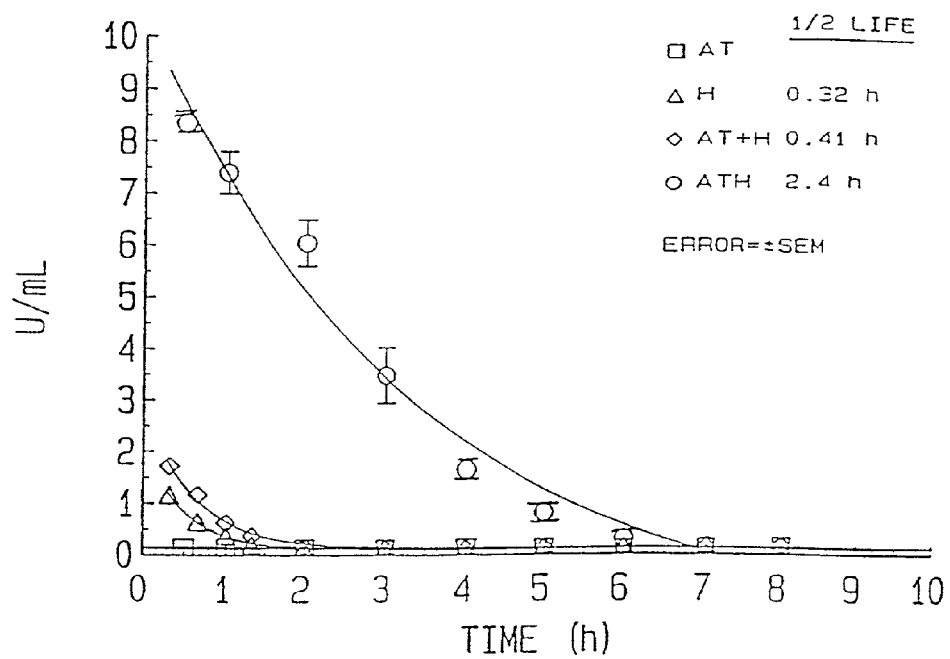
FIG. 12 shows the pharmacokinetic of ATH after intravenous injection, as measured by anti-factor Xa activity.
Figure 13:
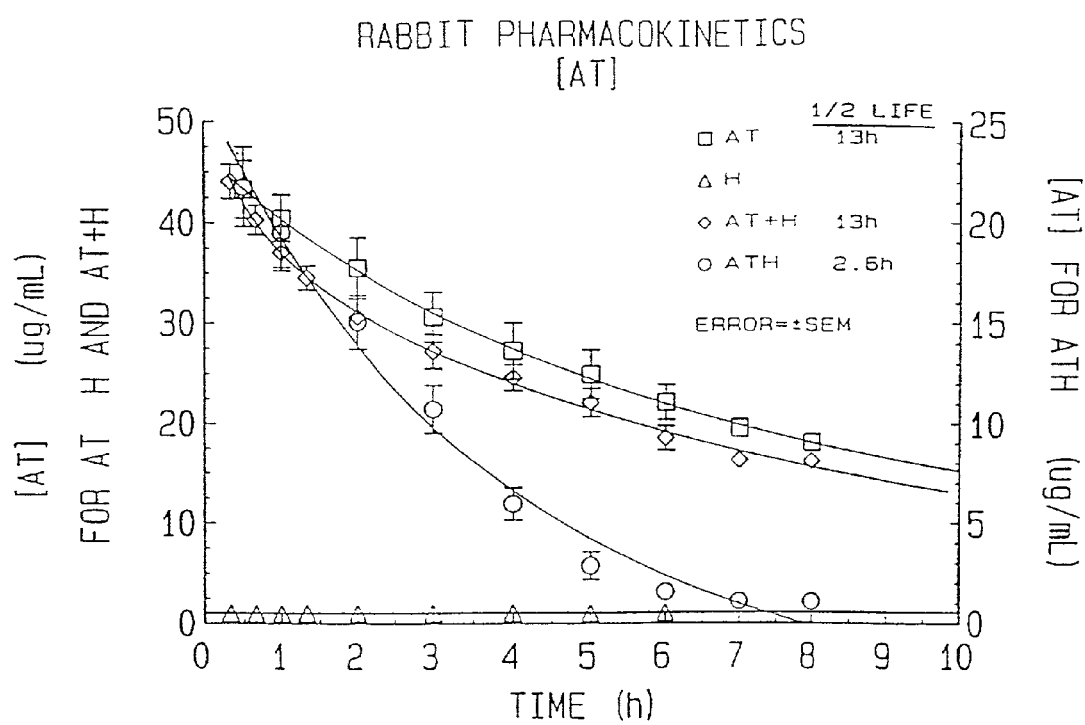

Five rabbits were used for each group. The compounds were administered intravenously to conscious, pathogen free, NZW rabbits. Citrated blood samples were taken from the rabbits at different time points up to 24 hours. Anti-factor Xa assays and ELISAs of human AT were performed on each sample. The half lives of ATH, AT+SH and SH by anti-factor Xa activity are about 2.4 hours, 0.41 hour and 0.32 hour respectively. The half lives of ATH, AT+SH and AT by ELISAs of human AT are 2.4 hours, 13 hours and 13 hours respectively. The results are summarized in FIGS. 12 and 13 and Table 9. The half lives of SH after intravenous injection and AT in humans are reported to be about 60 minutes and 66 hours respectively, which is approximately 2 times the half life of SH and 5 times the half life of AT in rabbits. Based on these observations, the half life of ATH in humans is expected to be 2–5 times that in the rabbit, which is about 5 hours to 12 hours. This long half life of ATH will be a distinct advantage for use in prophylaxis, as it can be administered infrequently. The maximal anti-factor Xa activities for ATH and SH were 8.4 u/ml and 1.17 u/ml respectively.

2. Pharmacokinetics After Subcutaneous Administration in Rabbits

The amounts of compound administered subcutaneously to the rabbits are shown in Table 10.

Figure 14:
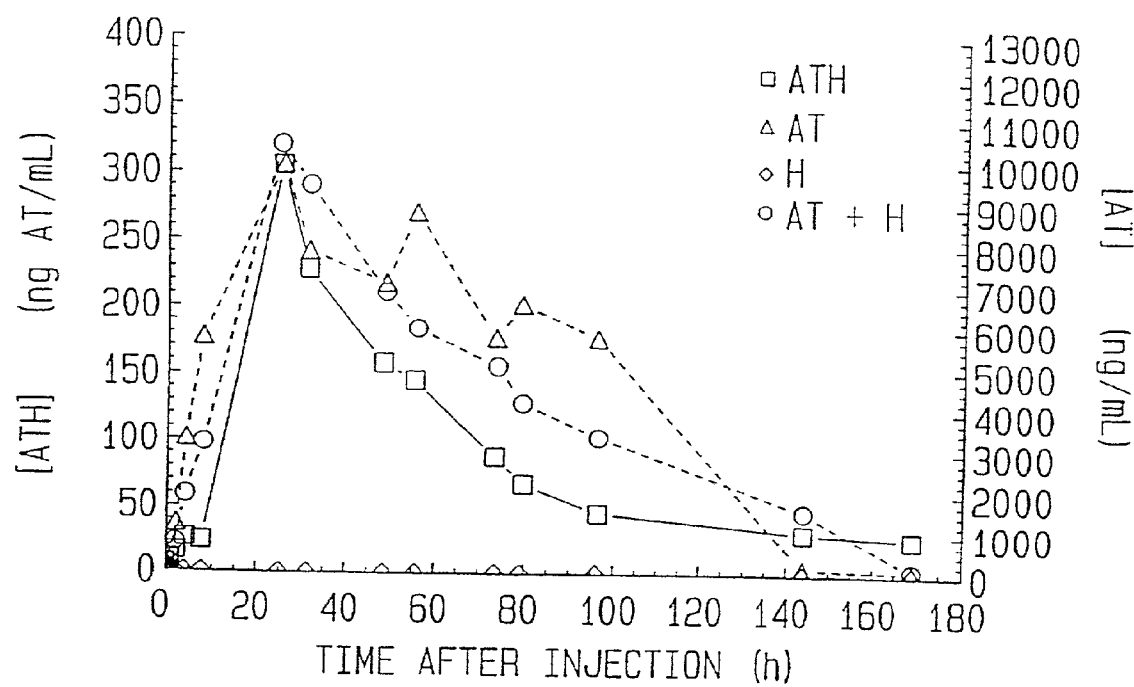
FIG. 14 shows the pharmacokinetic of ATH after subcutaneous injection.

Two dosages were tested and one animal was used for each dose. The compounds were administered subcutaneously to conscious, pathogen free, NZW rabbits. Citrated blood samples were taken from the rabbits at different time points up to 170 hours. Anti-factor Xa assays and ELISAs of human AT were performed on each sample. The maximal antifactor Xa activity for SH was 0.29 u/ml at 1 hour but there was essentially no anti-factor Xa activity in rabbits that received ATH. FIG. 14 shows the mean concentration of AT over time. These results suggested that ATH was not absorbed well with the dosage given by the subcutaneous route. This is probably due to the size of the molecule.

3. Pharmacokinetics After Tracheal Instillation in Rabbits

One potential use for ATH is to treat respiratory distress syndrome. Therefore, the effect of ATH after tracheal instillation was investigated.

Figure 15:
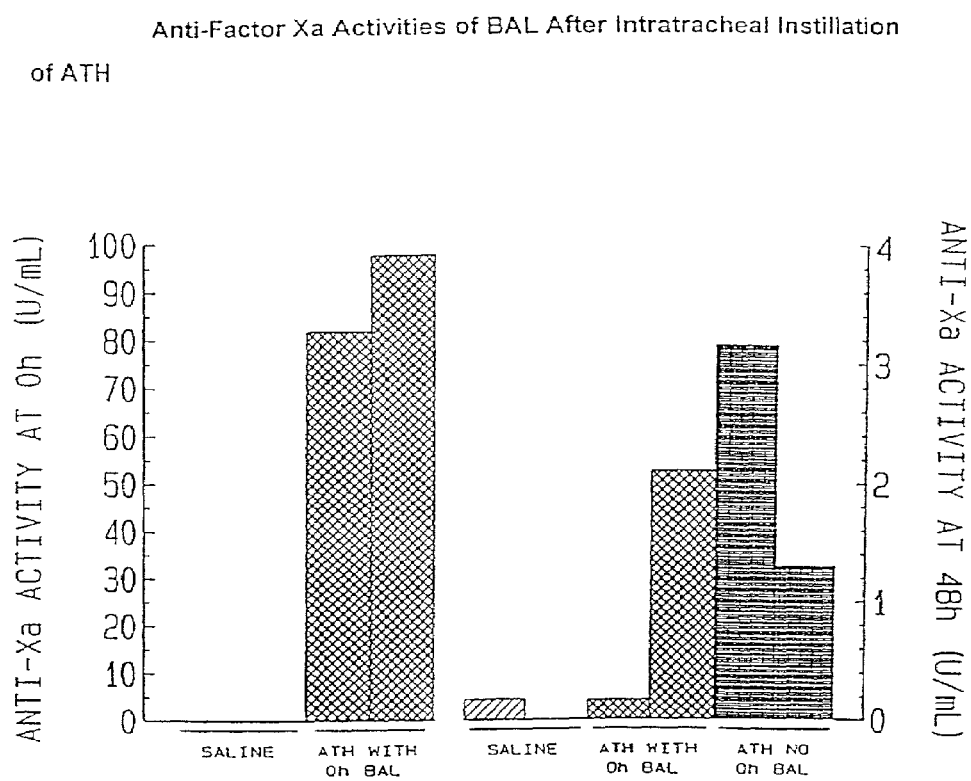
FIG. 15 shows the anti-factor Xa activities of BAL after intratracheal instillation of ATH.

ATH and saline were administered intratracheally through an endotracheal tube to anaesthetized pathogen free NZW rabbits. The amount of ATH administered was 100 anti-factor Xa u/kg. Four rabbits were used for ATH and two rabbits used for saline. For two of the rabbits that received ATH and rabbits that received saline, bronchoalveolar lavage (BAL) was done immediately after the instillation to assess whether it is possible to remove the compound after administration. BAL were collected on all animals at 48 hours. Citrated blood samples were taken at multiple time points up to 48 hours. Anti-factor Xa assays were done on both BAL and blood samples. There was essentially no anti-factor Xa activity in the blood samples. For the BAL at the time 0 hour, a significant amount of ATH was removed as evidenced by the high anti-factor Xa activity. At 48 hours, there was still anti-factor Xa activity remaining in the BAL (FIG. 15). These preliminary results demonstrated that ATH remained in the lung for a prolonged period of time and did not give rise to a significant anticoagulant effect systemically.

Example VII

Antithrombotic and Haemorrhagic Effects of ATH in Experimental Models: Comparison with Heparin The safety and efficacy of ATH has been tested in two animal models. The results of these experiments demonstrate that (i) ATH prevents thrombus growth and accelerates physiologic fibrinolysis in an animal model of venous thrombosis, and (ii) ATH is effective at doses that have acceptable haemorrhagic effects.

1. Comparison of ATH with Heparin in a Rabbit Bleeding Model

The relative effect of ATH, AT+SH, SH alone, AT alone and saline on experimental bleeding using a rabbit bleeding ear model were compared. The 5 treatment arms are shown in Table 11.

The doses given were equivalent by weight. Five rabbits were studied in each group.

In these experiments, rabbits were anaesthetized and test compounds were given as an intravenous bolus. Five minutes after the compounds were injected, one ear of the rabbit was punctured by a #11 surgical blade five times in a random fashion avoiding areas with visible vessels. The ear was then placed in a 37° C. water bath (total volume of 1 liter) that was stirred continuously. Ten ml aqueous samples from the water bath were taken at 5 minutes, 10 minutes, 20 minutes and 30 minutes from the time of the ear being punctured. Citrated blood samples were also taken at the same time points. Samples were centrifuged immediately at 1,700 g, platelet-poor plasma obtained and frozen at −70° C. until assays were performed.

Anti-factor Xa assays were done on the plasma samples. Absorbance of the water samples were measured at a wavelength of 540 nm and results were compared to a standard curve of known amounts of blood in water and the accumulative blood loss over time was calculated.

Figure 16:
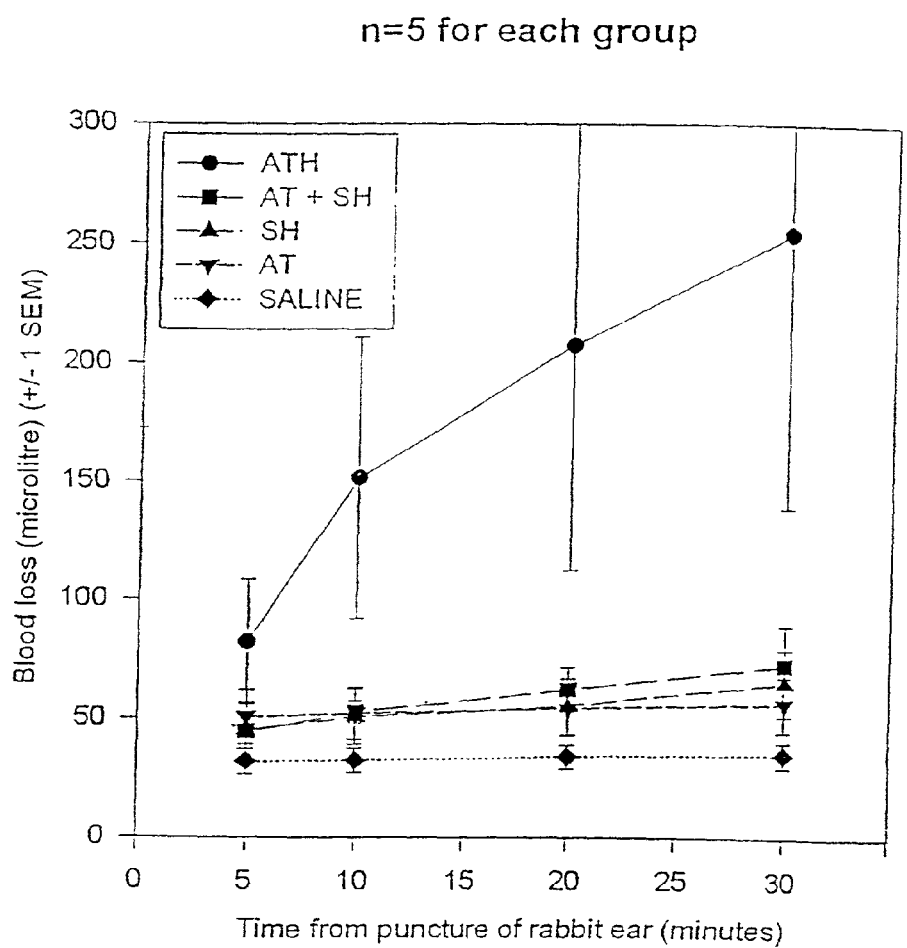
FIG. 16 shows cumulative blood loss after treatment in a rabbit bleeding ear model.
Figure 17:
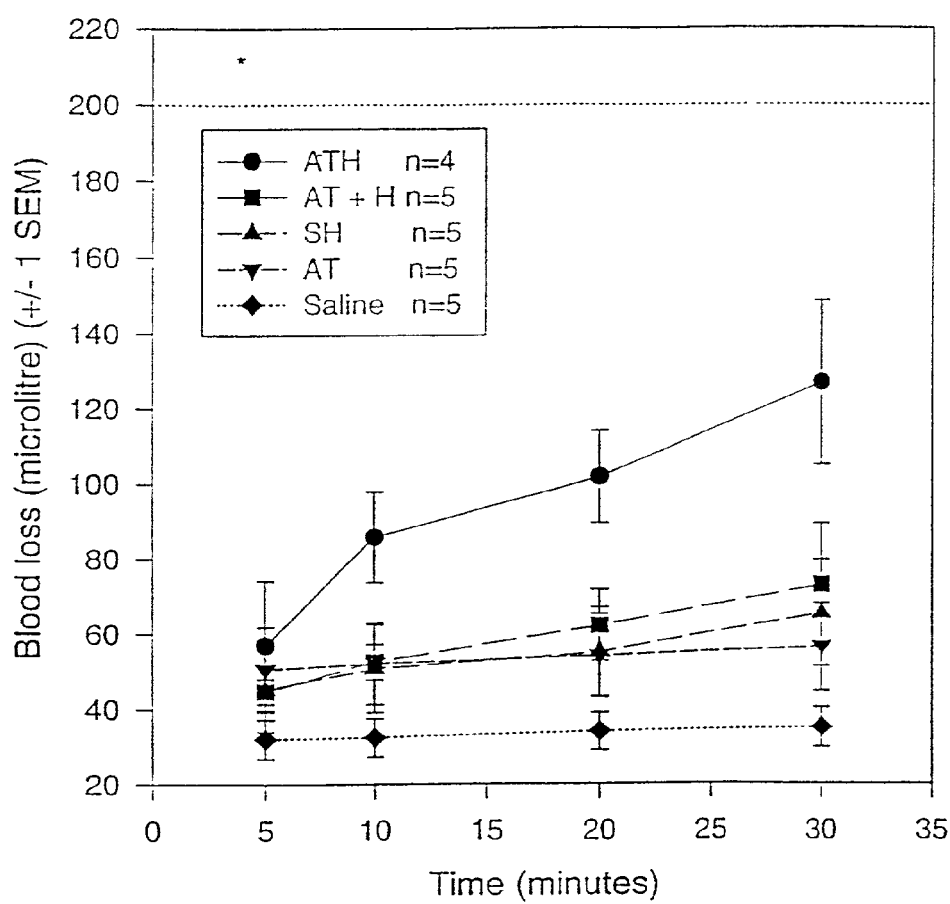
FIG. 17 shows cumulative blood loss after treatment (with outlier removed) in a rabbit bleeding ear model.
Figure 18:
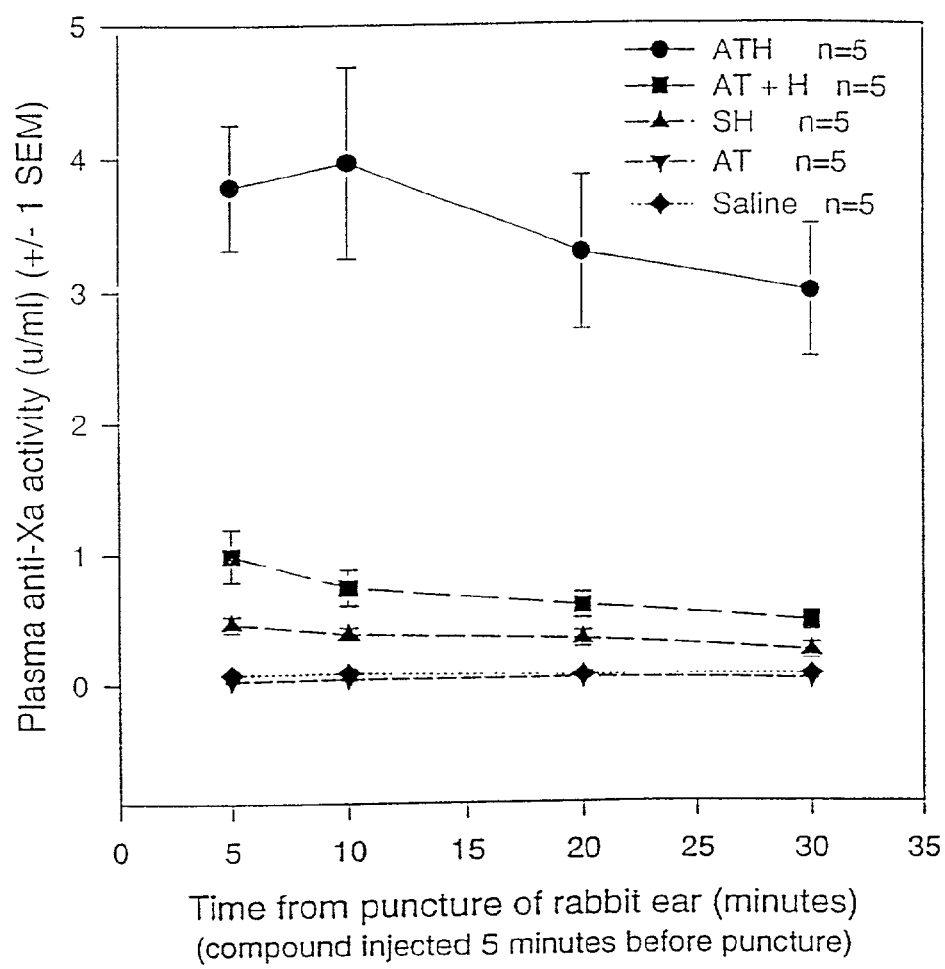
FIG. 18 shows plasma anti-factor Xa activity in a rabbit bleeding ear model.

FIG. 16 shows the cumulative blood loss over time. Bleeding was highest in the ATH group. One animal in the ATH group had significantly more bleeding than the rest of the animals in the same group. FIG. 17 shows the cumulative blood loss over time when this outlier was taken out of the analysis. The bleeding from the animals in the ATH group was well below the accepted amount of 200 pi blood loss over 30 minutes. Moreover, the cumulative blood loss in the first five minutes was essentially the same for all treatment groups that had anticoagulant. The increased cumulative blood loss in the ATH group is then likely due to its prolonged anti-factor Xa activity. The increased bleeding from ATH may also reflect the fact that anti-factor Xa activities were four times greater than those in the group that received AT+SH. FIG. 18 shows the plasma anti-factor Xa activity over time and demonstrates that anti-factor Xa activities of ATH last longer compared to the group that received AT+SH.

2. Comparison of ATH with Heparin in a Rabbit Venous Thrombosis Model

ATH was evaluated in a rabbit venous thrombosis treatment model. In these experiments ATH was compared to AT+SH, SH alone, AT alone and saline. The doses used were the same as those used for the rabbit bleeding ear model. The number of rabbits used for each group were n=5 for ATH, n=7 for AT+SH, n=8 for SH, n=5 for AT and n=5 for saline.

The rabbits were anaesthetized. The jugular vein was isolated and the side branches over 2 cm of the jugular vein ligated. The jugular vein segment was isolated with 2 tourniquets and a fogartry catheter inserted into the segment of vein. The endothelium was denuded by 15 passes of the inflated catheter and then 500 u of thrombin was injected into the segment. Then 0.2 ml of the rabbit's blood was injected into the segment to create a thrombus. At the same time 0.2 ml of the blood was placed into each of the two test tubes, acting as a control for the weight of the clot. Thirty minutes after the blood was injected into the vein, the tourniquets were released and the blood clot was exposed to systemic circulation. Ten minutes prior to the release of the tourniquets, the compounds tested were injected into the animals followed immediately by an injection of $^{125}$I-human fibrinogen. A 2 ml citrated blood sample and 1 ml clotted blood sample were taken at 10, 20, 30, 60, 120 and 180 minutes after the tourniquets were released. The citrated blood samples were centrifuged to obtain platelet poor plasma and then stored at −70° C. These samples were subsequently assayed for anti-factor Xa activity. At 180 minutes, the animals were euthanised and thrombi recovered. The weight and radioactivity of the thrombi were compared with the control thrombi from the same animal.

Figure 19:
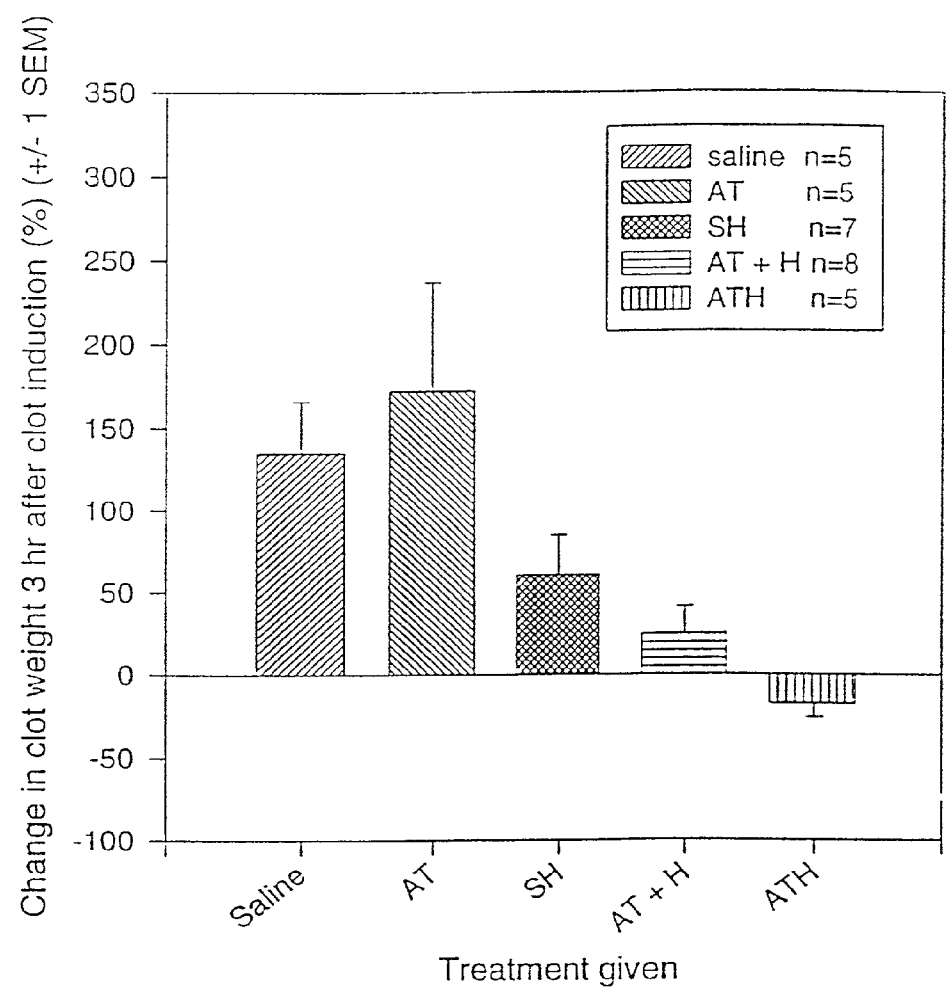
FIG. 19 shows the change in clot weight for different treatment groups in a rabbit venous thrombosis model.
Figure 20:
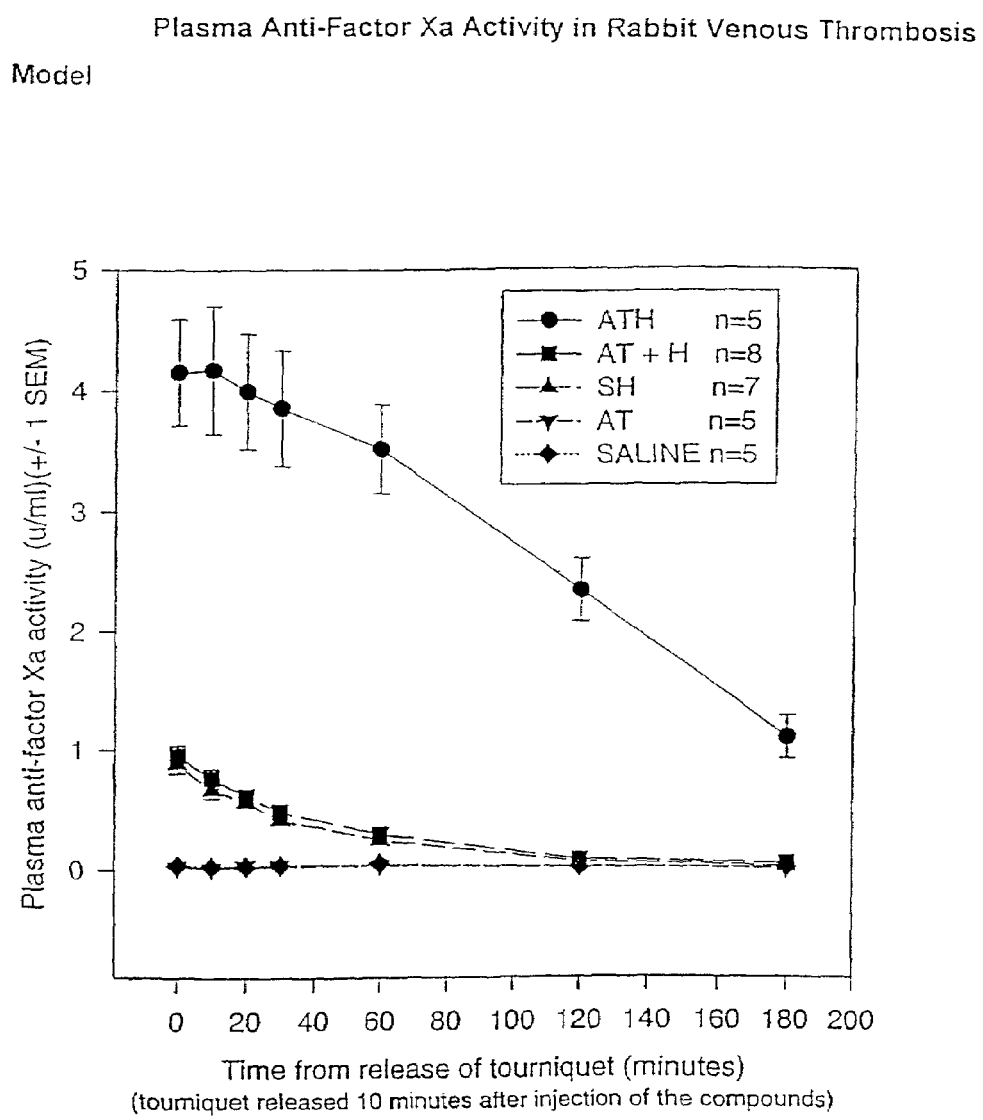
FIG. 20 shows plasma anti-factor Xa activity in a rabbit venous thrombosis model.

The model is designed to test the ability of an anticoagulant to prevent thrombus growth. The results shown in FIG. 19 indicate that ATH, AT+SH and SH were more effective than the saline control and AT control in preventing thrombus growth. However, ATH was the most effective treatment and was associated with an 18% reduction in thrombus size. The decrease in clot size was similar to results when agents that have activity towards fibrin bound thrombin were used. These data suggest that ATH has activity against fibrin bound thrombin. However, FIG. 20 shows that rabbits which received ATH had a higher anti-factor Xa activity compared to other groups. Therefore, it remains to be tested whether the more efficacious effect of ATH is due to a higher anti-factor Xa activity or to an accelerated activity of ATH itself.

It is likely that equivalent anti-factor Xa activities of heparin and ATH will result in less bleeding with ATH and that the reduced bleeding with ATH may be due to limited antiplatelet activity.

Example VIII

ATH as a Local Anticoagulant to Coat a Prosthetic Surface

ATH was used as a local anticoagulant to coat thrombogenic prosthetic surfaces. To do this, a polyurethane-polycarbonate endovascular tubing from Corvita was coated with ATH by covalent linkage of the urethane groups to ATH by an intermediate monomer linker. The thrombogenecity of the coated tubing was tested in a Rabbit Jugular Vein Model (rabbit perfusion model), and compared to hirudin coated tubing, AT coated tubing and non-treated tubing.

1. Methods of Coating Polyurethane-polycarbonate with ATH

Three steps are involved in the chemistry for coating ATH onto polyurethane-polycarbonate. First, the polymer of polyurethane-polycarbonate is activated with NaOCl. NaOCl reacts with urethane to make this relatively inert material chemically reactive. Second, a linking monomer (allyl glycidyl ether) is grafted onto the surface by reacting the activated tubing with an initiator ($Na_2S_2O_4$) and a monomer that can further react with other compounds such as ATH. Third, ATH (or other anticoagulants that have groups, such as, an amino group, that can react with the functional group of the monomer) is linked to the monomer.

2. Comparison of ATH Coated Tubing with Hirudin Coated Tubing

Hirudin was linked to polyurethane-polycarbonate tubing using the same method as that used for linkage of ATH. In these experiments, New Zealand White male rabbits were anaesthetized. The femoral artery and vein were cannulated with a cannula used for fluid administration and blood collection. The external jugular vein was exposed and a small segment of the facial vein partially occluded. A modified 14 gauge Angiocath (5 cm long) was inserted into the jugular vein. A 2 cm segment of the endovascular tubing was weighed and inserted into a modified 14 gauge Angiocath (5 cm long) catheter. The modification of the Angiocath consisted of cutting the tip off its stylet. The catheter was inserted 5 cm into the jugular vein via the partially occluded facial vein and the tubing then deployed. Thereafter, the catheter was withdrawn and the facial vein segment ligated. The tubing location can be seen through the jugular vein wall. Prior to insertion of the tubing and at 60, 120, 180 minutes after its deployment, 1 ml of blood was collected into citrate-PPACK as well as into citrate-THAT-M for thrombin-antithrombin complex (TAT) and fibrinopeptide A (FPA) analysis. At the end of 180 minutes, the segment of the external jugular vein containing the tubing was removed, flushed with 10 ml of saline and the outside diameter measured using callipers. Thereafter the segment of vein containing the tubing was opened longitudinally with scissors and the vein peeled off from the tubing. The tubing was cut longitudinally into two halves, blotted slightly on gauze and weighed. Blood samples were centrifuged immediately at 1,700 g, platelet-poor plasma obtained and frozen at $-70°$ C. until assays were performed. The tubing were stored in 10% formalin for histopathology.

Figure 21:
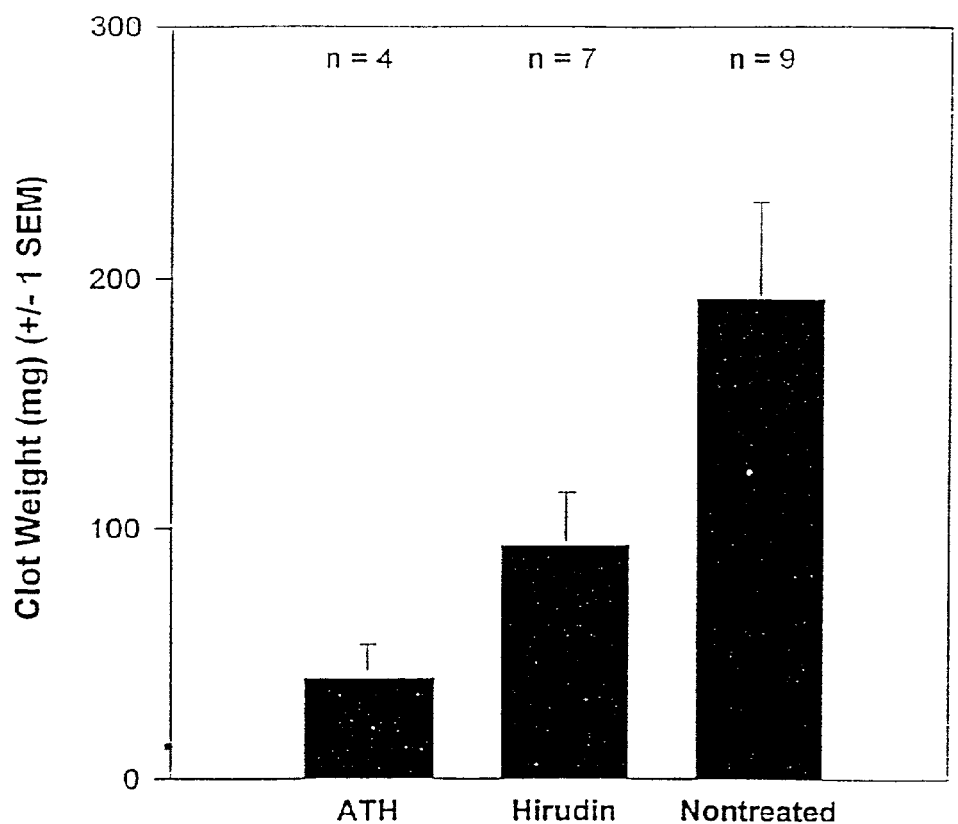
FIG. 21 shows the clot weights when ATH-grafted, hirudin-grafted, and untreated polyurethane tubing are used in a rabbit perfusion model.
Figure 22:
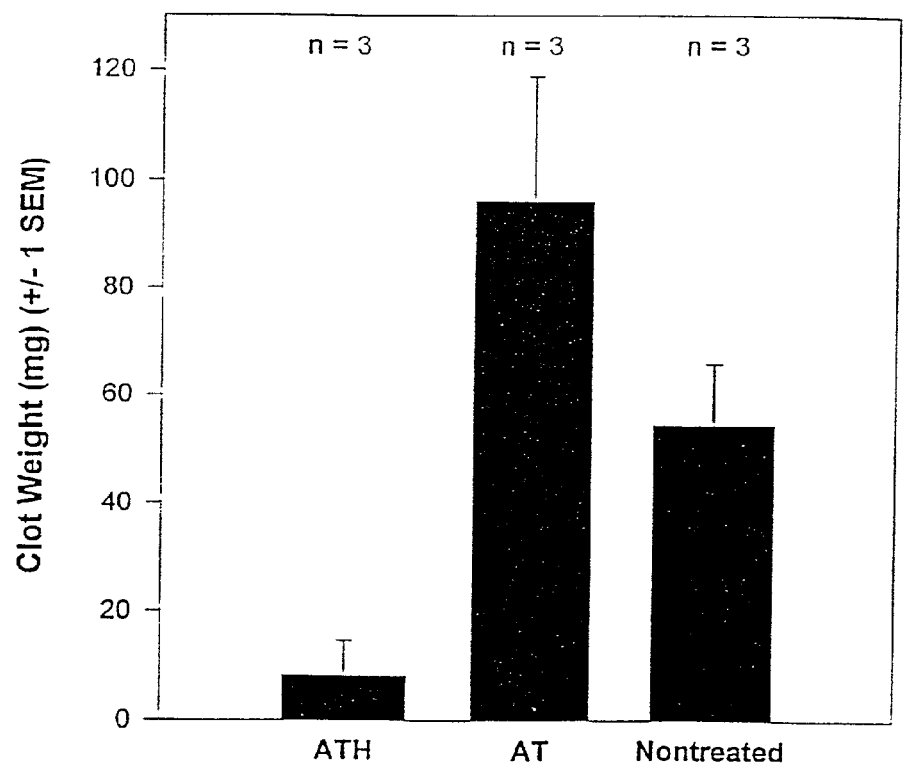
FIG. 22 shows shows the clot weights when ATH-grafted, AT-grafted, and untreated polyurethane tubing are used in a rabbit perfusion model.

FIG. 21 shows the weight of clots formed inside the tubing after they were inserted into rabbits for three hours. As shown in the graph, the weight of clots formed within the ATH coated tubing was statistically and strikingly less than that in the hirudin coated tubing, demonstrating that ATH coated tubing is more effective than Hirudin coated tubing 3. Comparison of ATH Coated Tubing with AT Coated Tubing and Non-treated Tubing The experimental procedures were the same as above. FIG. 22 shows the weight of clots that were formed inside tubing after the insertion into rabbits for three hours. ATH coated tubing induced smaller clots than AT coated tubing and non-treated tubing. Thus, the AT coated tubing was significantly more thrombogenic than ATH coated tubing.

Figure 23:
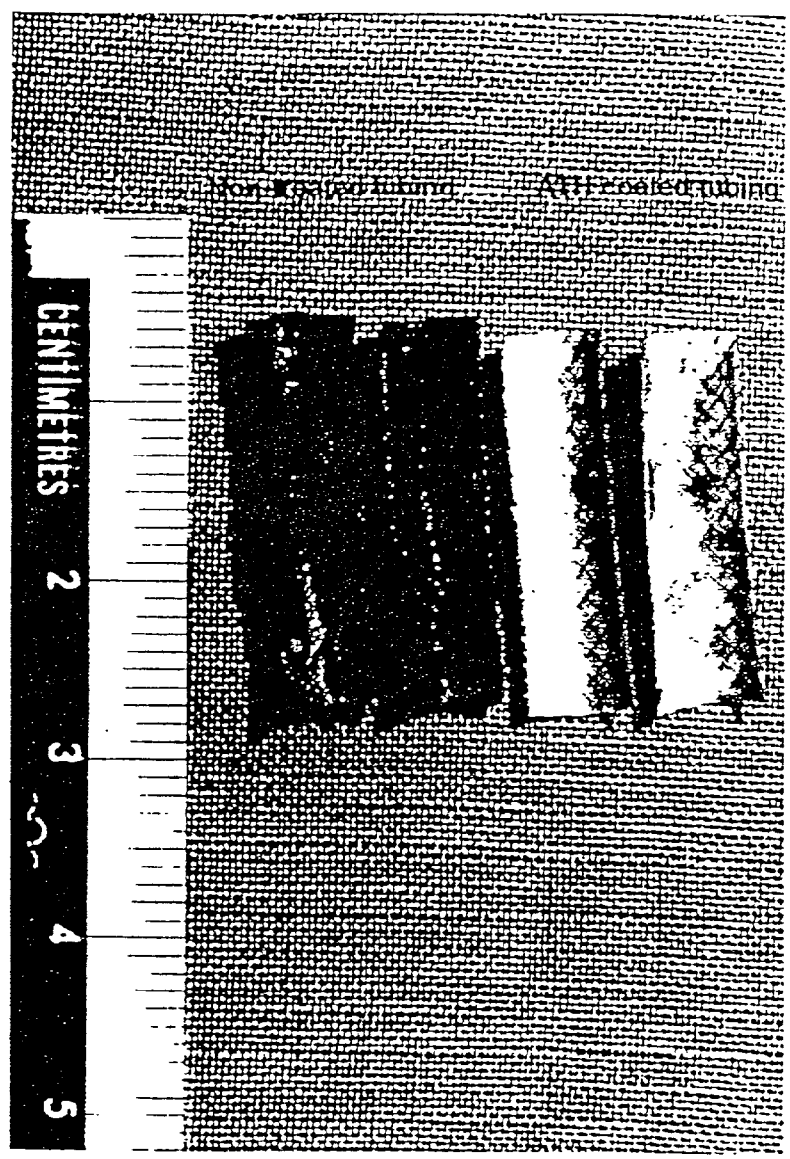
FIG. 23 shows the luminal surface of ATH-treated and untreated tubing after exposure to blood for three hours in rabbits.

FIG. 23 shows the luminal surface of an ATH coated tubing and a non-treated tubing after exposed to blood in a rabbit for three hours. The ATH coated tubing had minimal amount of blood clot on the surface but the non-treated tubing had clearly induced more clot.

Example IX

Formation of ATH In Vivo Following Heparin Injection

To study in vivo ATH generation, rabbits were injected with heparin (200 U/kg intravenously and 400 U/kg subcutaneously followed after 3 h by 100 U/kg intravenously and 400 U/kg subcutaneously) and then, at 5h after initial injection, exsanguinated into Na citrate (0.38% final concentration). Saturated $(NH_4)_2SO_4$ was added to the resultant plasma (1 µL/mL of plasma) to prevent any further Schiff base formation ex vivo. Covalent antithrombin-heparin generated in vivo was purified from plasma by initially collecting the supernatant after adding saturated $(NH_4)_2SO_4$ until 40% saturation was reached. After dialysis vs 0.01M Tris HCl pH 8.0, chromatography was carried out on DEAE Sepharose as described above. This was followed by chromatography on butyl agarose using the same method as the one described earlier except that elution of bound antithrombin-heparin was with 1.2M $(NH_4)_2SO_4$ in buffer. After concentration by pressure-dialysis, materials were analyzed by western immunoblotting using either an anti rabbit AT or anti human AT antibody raised in sheep (Affinity Biologicals).

Figure 27:
FIG. 27 shows a Western immunoblot of material isolated from plasma of rabbits injected with heparin. An antithrombin containing polydisperse, high molecular weight complex is present (lane 1) which disappears on treatment with heparinase, leaving only the antithrombin band.

FIG. 27 shows the results for a Western blot, developed using anti-rabbit AT antibody, of material recovered from the plasma of heparinized rabbits using a method adapted from the procedure for purification of covalent antithrombin-heparin produced in vitro. Polydisperse material, higher in molecular weight than rabbit AT, was recognized by the antibody (FIG. 27) which disappeared on treatment with heparinase (FIG. 27, lane 2). These data confirmed the presence of a species of ATH, produced in vivo, with the characteristics of a covalent complex. Western blots of AT, H and non covalent mixtures of AT+H showed no high molecular weight band, whereas an identical band compared to the in vivo material was observed with covalent ATH produced in vitro (data not shown).

In rabbits, 0.005% (by mass) of the peak level of H in plasma was recovered as antithrombin-heparin. Thus, injection of 7.5 mg of H subcutaneously in a rabbit yielded, after 4 h, 0.25 µg to 0.4 µg of ATH in terms of H.

Figure 28:
FIG. 28 shows a Western immunoblot of material isolated from plasma of a human injected with heparin. A high molecular weight antithrombin complex is seen (lane 1) which diminishes with heparinase treatment (lane 2), and is absent in the normal human plasma pool (lane 3). In both heparinase-treated and normal human plasma pool samples (lane 2 and lane 3, respectively), a band which corresponds to antithrombin without attached heparin is visible.

A single, subcutaneous injection of H to a human gave results similar to rabbits. 200 U heparin/kg was injected subcutaneously into a female human followed, after 5 h, by removal of 100 mL of blood into citrate. The resultant plasma was then processed as described above for rabbits. A polydisperse, high molecular weight antithrombin-heparin complex was obtained which was not present in plasma from untreated humans (FIG. 28). Gels of the complex stained positively for H in the same region as the protein band. Laser densitometry of the blots was used to determine the amount of ATH generated (compared to a standard curve of ATH produced in vitro) from the H injected. The recovery of ATH in the plasma of the human subject was comparable to the results, described above, for rabbits.

These findings are the first demonstration of spontaneous formation of covalent polypeptide-polysaccharide complexes in an organism.

Example X

Blood-compatible Biomaterials by Surface Coating with a Novel Antithrombin-Heparin Covalent Complex Covalent antithrombin heparin complex (ATH) was covalently grafted to a polycarbonate urethane (Corethane®) endoluminal graft (Corvita Corporation) after being activated using 0.3% m/m NaOCl in 0.15M phosphate pH 6.0. ATH graft density ($1.98 \times 10^{-7}$ moles/m$^2$) was 6 times the maximum amount of unfractionated heparin (UFH) that could be bound to polycarbonate urethane surfaces. Surface-bound ATH could be stored in sterile 0.15 M NaCl at 4° C. for at least two months with good antithrombotic activity before being implanted into rabbits. Analysis of ATH coated tubing showed that it contained significant direct thrombin inhibitory activity. In vivo testing in a rabbit model was compared to non-activated non-coated surfaces, activated-noncoated surfaces, Hirudin coated surfaces and antithrombin (AT) coated surfaces. The weight of the clot generated in the ATH coated graft tubing was significantly less than the weight of the clot generated within the hirudin coated graft (p=0.03 with a 1 tailed Student's t test). The anticoagulant nature of ATH grafts in vivo was shown to be due to bound ATH because both the AT-coated surfaces and non-coated but activated surfaces showed similar thromboresistant efficacy to that of untreated material (ANOVA; p<0.05). Apart from the direct antithrombin activity that contributed to much of the prolonged patency in vivo, surface-bound ATH likely catalyzed AT inhibition of thrombin, as evidenced by a significant number of $^{125}$I-AT binding sites ($1.5 \times 10^{-8} \times \geq$ moles/m$^2$). Thus, ATH appears to be a good candidate for coating cardiovascular devices, such as endoluminal grafts, with high levels of substitution and significant long-term blood-compatibility.

MATERIALS AND METHODS

Chemicals

All chemicals were of analytical grade. The AT used in all experiments was human AT from Bayer (Mississauga, ON). UFH was grade I-A, standard heparin (Na salt, 209 anti-factor Xa U/mg, obtained from porcine intestinal mucosa) from Sigma (Mississauga, ON). ATH was prepared by incubation of AT and UFH, and purification of the product as described previously (Berry L, et al, Polymeric Biomaterials. Part II: Medical and Pharmaceutical Applications of Polymers. 2 Ed. New York: Marcel Dekker Inc., 2000). The average molecular weights (determined by gel filtration) of UFH, and heparin isolated after protease treatment of ATH were 15000 D and 18000 D, respectively. Thrombin and factor Xa (FXa) were both from Enzyme Research Laboratories Inc. (South Bend, Ind.). Hirudin was purchased from Behring (Marlberg, Germany). Fibrinogen was from Sigma. $^{125}$I-labeled AT and Fibrinogen were prepared using Na$^{125}$I (New England Nuclear, Mississauga, ON) and Chloramine T (BDH, Toronto, ON)[29]. Polycarbonate urethane endoluminal graft tubing (Corethane®) was a gift from Corvita Corporation (Toronto, ON, Canada). NaOCl, sodium phosphate, Fe(NH$_4$)$_2$(SO$_4$)$_2 \cong$6H$_2$O, Na$_2$S$_2$O$_4$, and allyl glycidyl ether were purchased from Fisher chemicals (Fairlawn, N.J., USA). SDS-PAGE chemicals were purchased from Aldrich (Oakville, ON, Canada). Gel staining agents, (Alcian Blue and Coomassie Blue) were purchased from Sigma (Oakville, ON, Canada). Agents for bioactivity measurement, anti-factor Xa heparin activity assay kits and anti-factor IIa heparin activity assay kits were purchased from Diagnostica Stago (Asnieres, France). Chromogenic substrate for thrombin, S-2238, was purchased from DiaPharma (Milan, Italy). New Zealand White male rabbits (Charles River, St. Constant, Canada) were used for in vivo patency testing of ATH-coated grafts.

Graft Preparation

ATH was prepared by a method described previously (Chan A K, et al, J Biol Chem 1997; 272: 22111–22117). AT was incubated with UFH at 40° C. in pH 7.3 PBS buffer for 10 to 14 days. The product was then purified on butyl-agarose followed by DEAE Sephadex chromatography. Quality of ATH preparations was evaluated by SDS-PAGE. ATH-coated grafts were derived by first activating polycarbonate urethane by agitation in 0.3% m/m NaOCl 0.15M phosphate pH 6.0 at 23° C. for 5 min, followed by agitation for 5×15 sec with 0.15 phosphate pH 6.0 and 15 sec with water. The activated tubing was subsequently incubated with an initiator (either 3.77% m/m Fe(NH$_4$)$_2$(SO$_4$)$_2$·6H$_2$O or 0.1% m/m Na$_2$S$_2$O$_4$) and a monomer (5% m/m allyl glycidyl ether) in 0.15M phosphate pH 8.0 at 23° C. for 24 h. Previous work under these conditions and concentrations, with a variety of monomers, has shown that products with oligomers composed of 1–4 monomer units are formed at each urethane group (Hoerl H H, et al, Sartorius A-G. DE 3,929,647(DE 4,028,326). Mar. 14, 1991. Germany. Sep. 14, 1989). After rinsing for 5×1 min in 0.15 M phosphate pH 8.0 buffer, the endoluminal graft was finally incubated with either: pH 8.0 buffer, 15 mg/ml UFH/ml pH 8.0 buffer, or 2 mg protein/ml pH 8.0 buffer (either ATH, AT or Hirudin) at 4° C. for 24–48 hours. In typical experiments, 2 cm segments of 6 mm internal diameter tubing were incubated in rotating, capped 12 mm I.D×75 mm long polycarbonate test tubes containing 2 ml of coating solution. The final product was rinsed for 5×1 min with pH 8.0 buffer, followed by 2×1 min rinses with 0.15 M NaCl. The tubing was stored at 4° C. submerged in 0.15 NaCl.

Physico-Chemical Characterization

Analyses of the level of substitution of anticoagulant on the surface of the graft was determined by staining for either protein (Coomassie Blue) or heparin (Alcian Blue). Bound stain was dissolved into dimethylsulfoxide and absorbance measured at 678 nm. Comparison of results from stained grafts with those of known amounts of protein or heparin spotted onto cellulose polyacetate stripes, which were stained and analyzed as above, gave the amount of material coated on the graft surface. Stability of the product under different conditions was assessed by anti-factor Xa heparin activity assays (kit from Diagnostica Stago). Direct inhibition of thrombin by Hirudin- and ATH-coated surfaces was measured by incubation of grafts with thrombin, followed by detection of residual thrombin activity. Tubing segments (0.5 cm) were incubated with excess thrombin ($2.25 \times 10^{-11}$ moles thrombin) for 10 min at 37° C., followed by assay of residual thrombin activity with the chromogenic thrombin substrate S-2238 (DiaPharma). Residual thrombin was assayed by addition of substrate directly to the tubing+thrombin incubate (in the case that thrombin was bound to the surface but not inhibited) or to an aliquot of thrombin incubate solution (to check for any background colour ($A_{405}$) from the tubing). Comparison of residual activity to a standard curve of reaction of varying amounts of thrombin with S-2238 gave the number of moles of thrombin neutralized by the surface. The limit of detection for thrombin inhibition by the assay was within $2 \times 10^{-11}$ to $4 \times 10^{-11}$ moles of thrombin neutralized/m$^2$. Investigation of the exogenous AT binding capacity was tested by measurement of $^{125}$I-AT binding (AT labelled using iodobeads according to the manufacturer (Pierce)).

In Vivo Testing of Endoluininal Grafts

New Zealand White male rabbits (3–3.5 kg) were anaesthetized and the right jugular vein exposed. The weight of the endoluminal graft was obtained before insertion into the rabbit. A 2 cm (6 mm diameter) endoluminal graft was deployed into the external jugular vein of the rabbit through a 14 gauge 18-cm long Angiocath, after which the entry point was sutured closed. The endoluminal graft was left in situ for 3 hours. After 3 hours, the endoluminal graft was explanted and blotted on a gauze. The weight of the graft explanted from the vein was obtained. The weight of the clot formed inside the endoluminal graft was determined by calculating the weight of the graft after 3 hours in situ minus the weight of the graft taken before insertion into the animal. Net accretion of fibrin was assessed by measuring $^{125}$I-fibrin bound to explanted grafts from intravenous injection of 1 µCi $^{125}$I-fibrinogen (human fibrinogen from Sigma, labelled using the same method as for $^{125}$I-AT) immediately after insertion of the graft. In some experiments, venous blood samples were taken into citrate (9 volumes of blood to 1 volume 3.8% m/m sodium citrate) and the supernatant plasma assayed for thrombin-AT complexes (TAT) (using ELISA kits from Affinity Biologicals, Hamilton, ON, Canada).

Statistics

Results were reported as means±1 SEM unless otherwise indicated. Comparisons between different groups were made by analysis of variance (ANOVA) using Minitab® verion 11. Upon finding significance with ANOVA, the ATH group was then compared to other groups. An unpaired Student's t test was used when only two groups were compared. Values were considered statistically different for p values less than 0.05.

RESULTS AND DISCUSSION

Coating Technique, Coating Efficiency and Coating Stability

Figure 29:
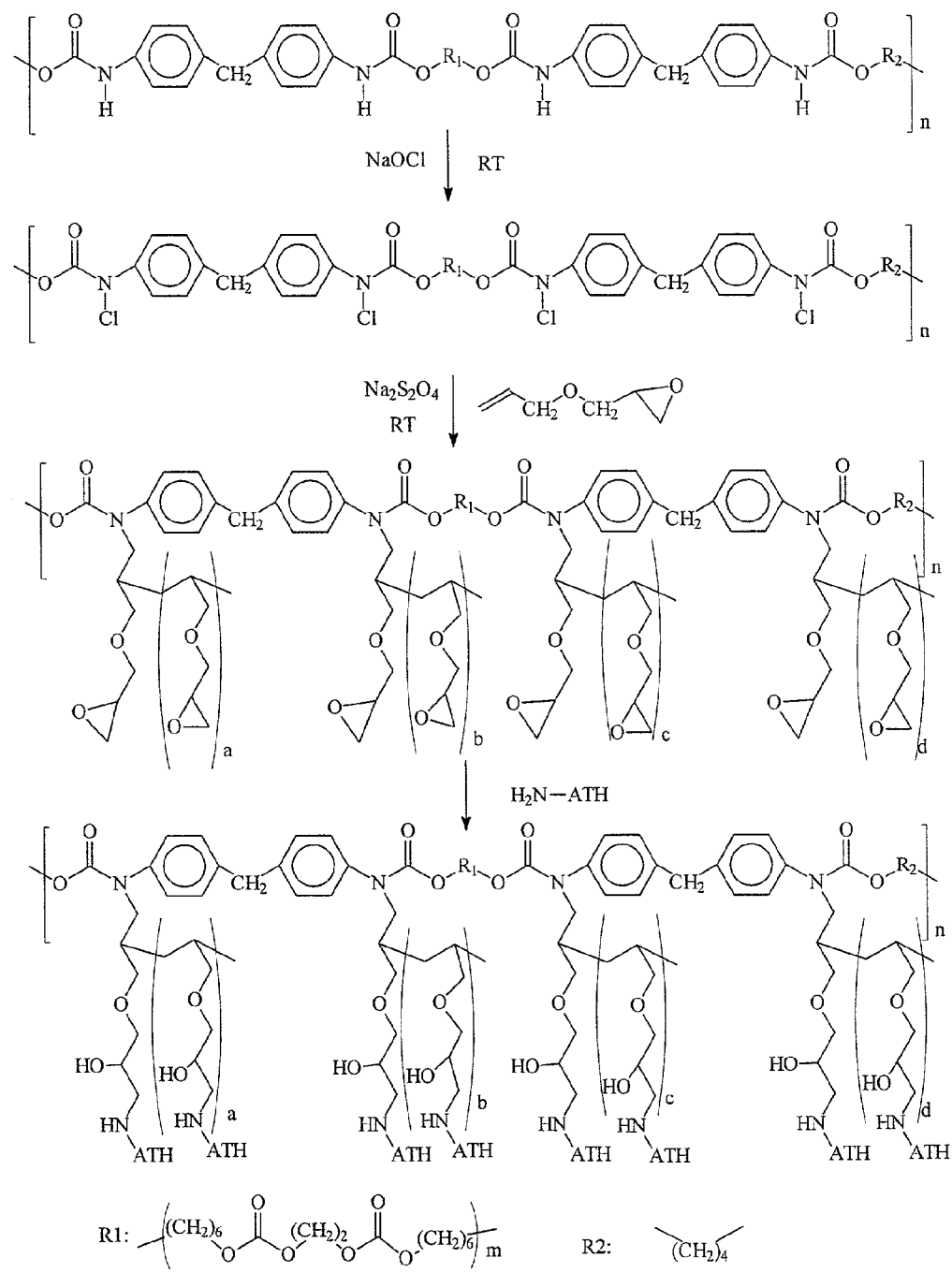
FIG. 29 shows a reaction protocol for the modification of polycarbonate polyurethane with an amino bearing molecule (i.e. ATH). The subscripts a, b, c and d are whole numbers.

One of the critical requirements for an efficient grafting is significant grafting density (Lee S J, et al, J Vasc Sci Technol 1994; 12: 2949–2955). For grafting onto a polyurethane, the most popular method is the activation of the polyurethane by a diisocyanate, followed by the reaction of the remaining isocyanate with an amino group or a hydroxyl group on the species being attached to the surface. However, this method may have reduced grafting density due either to limited reaction of the isocyanate with the imide group on polyurethane or reaction of the surface-bound isocyanate with water to yield amino groups. Free surface amino groups may lead to significant problems for heparin applications due to non-covalent binding of the highly sulfated and negatively charged chains to the cationic amino residues (Hatton M W, et al, Thromb Res 1978; 13: 655–670). Therefore, another route was pursued in order to modify the polyurethane surface. The grafting protocol is illustrated in FIG. 29. As can be seen from this reaction scheme, oligo(propyl glycidyl ether) was formed which may bear more than one glycidyl group at each grafting site. Thus at each site, more than one ligand (ATH given as an example) may be grafted, resulting in high grafting density. The grafting density of different materials coated on the surface surfaces are listed in Table 12. The grafting density of ATH on the modified polycarbonated urethane surfaces was $1.98 \times 10^{-7}$ moles/m$^2$, about 6 times the maximum amount of UFH that could be bound to activated polycarbonate urethane surfaces, in accordance with expectations (ATH protein has more amino groups per molecule than UFH).

In order to investigate the stability of this grafted surface, two experiments were carried out. The first experiment involved the incubation of the modified surface in blood at 4° C. for 96 hours. Graft samples (2 cm long, 6 mm I.D) were incubated in rotating capped polycarbonate polyurethane tubes (12 mm×75 mm) containing citrated human blood (2 mL) at 4° C. for 96 h. Incubated blood was centrifuged and the resultant supernatant plasma tested for either anti-factor Xa heparin activity or ability to inhibit thrombin. As can be seen in Table 12, no heparin activity was detected in the plasma, indicating that no significant bioactive ATH leached from the graft.

In the second type of experiment, grafted samples were maintained in sterile 0.15 M NaCl at 4° C. for at least two months. There was no significant loss of in vitro activity of modified surfaces for inhibition of thrombin, compared to the freshly modified surfaces, indicating the long term stability of the coated tubing.

Bioactivity of Different Surfaces

ATH has direct noncatalytic antithrombin activity because the presence of both AT and H provides a mechanism for the rapid direct inhibition of thrombin (Chan A K, et al, J. Biol Chem 1997; 272: 22111–22117). The direct non-catalytic effect of ATH relies on initial reaction of thrombin with ATH to form a covalent thrombin-ATH complex in which the thrombin has been neutralized. The capability of a surface coating to rapidly inhibit the small amounts of thrombin formed during the initial stages of the coagulation mechanism, prevents the feedback activation of factors V and VII by thrombin within the coagulation cascade (Ofosu F A, et al, Biochem J 1987; 243: 579–588). ATH has been shown to have the most rapid rate for direct thrombin inhibition ever reported (Chan A K, et al, J. Biol Chem 1997; 272: 22111–22117) and would thus effectively prevent induction of the coagulation cascade. Furthermore, formation of surface-bound neutralized thrombin (as thrombin-ATH) may provide a surface that inhibits further binding of either active thrombin or prothrombin. Additionally, ATH possesses an indirect antithrombotic effect. The indirect catalytic inhibition of thrombin by AT circulating in the plasma of an animal is enhanced by use of the ATH covalent complex, as opposed to ordinary H, because of the mechanism by which ATH is prepared. AT is incubated with H under conditions where H with high affinity pentasaccharide sites are selected by the AT during covalent bond formation. Thus, while unfractionated heparin contains only ~0.3 catalytic antithrombin binding sites/molecule, ATH has 1.3 to 1.5 catalytic sites per heparin chain (Chan A K, et al, J Biol Chem 1997; 272: 22111–22117; Berry L, et al J Biol Chem 1998; 273: 34730–34736). Surfaces coated with ATH would have significantly more indirect (catalytic) activity than surfaces coated to a similar density with heparin.

Both direct and indirect antithrombin activities of ATH may be maintained after it is attached to the surface. Thus, for comparison, activities of hirudin and UFH-modified surfaces were also investigated. In order to assess anticoagulant activities of the surfaces, grafts were tested for their ability to inhibit thrombin (direct non-catalytic activity) and $^{125}$I-AT binding capacity (number of pentasaccharide sites for catalysis of AT reaction with thrombin). Because both non-catalytic and catalytic antithrombin activities have been observed for ATH (Chan A K, et al, J Biol Chem 1997; 272: 22111–22117; Berry L, et al J Biol Chem 1998; 273: 34730–34736), control surfaces for either direct activity (hirudin modified surface) or indirect catalytic activity (UFH modified surface) were created. Table 13 shows the results for ATH- and hirudin- and UFH-coated polyurethanes. Thrombin inhibition tests of the surfaces modified with either ATH or hirudin showed that the direct non-catalytic activity of ATH is greater than that of hirudin modified surfaces. Also, results in Table 13 for the $^{125}$I-AT binding capacity of the surfaces (a measure of the ability to catalyze inhibition of thrombin by exogenous AT) showed that ATH modified surfaces had a higher capacity than that of surfaces coated with UFH, possibly due to the presence of multi-pentasaccharide sequences in the heparin chain of ATH (Berry L, et al J Biol Chem 1998; 273: 34730–34736). Both direct and indirect antithrombin activities may contribute to antithrombotic effects, as will be discussed in the next section.

It is most likely that increased effectiveness of the ATH coating, compared to the UFH coating, was a combination of increased surface coating density and increased anticoagulant activity of the attached ATH molecules. There were 2 pieces of evidence that give support to the hypothesis that improved antithrombotic activity of ATH-coated surfaces was due to both quantitative (surface density) and qualitative (activity per ATH molecule) increase in surface anticoagulant activity. First, while surface density of ATH-coating was 6.3 times greater than that for the UFH-coating (Table 12), $^{125}$I-AT binding data (a measure of indirect catalytic activity) showed that AT binding by the ATH surfaces was 9.2 times greater than that for UFH surfaces (Table 13). Thus, indirect catalytic activity was observed to be ~50% greater than what could be accounted for by increased substitution. Second, the ATH-coated grafts had significant direct non-catalytic activity against thrombin which was absent in the heparin-coated tubing. These results suggest that the overall anticoagulant nature of ATH-coatings has increased activity to that of UFH-coated surfaces, in addition to that provided by the increased surface density.

In Vivo Studies

In vivo tests provided crucial information to determine how efficient the modified surfaces were in preventing coagulation on the grafts. Hirudin coated grafts were used for comparison in vivo because hirudin is one of the most potent thrombin inhibitors and has been gaining clinical use as an anticoagulant therapy. Also, hirudin has previously been attached to biomaterials to yield surfaces with significant activity against thrombin (Wyers M C, et al, Cardiovasc Path 1999; 8: 153–159). Furthermore, since endoluminal grafts coated with covalent complexes of AT and heparin (ATH) had rapid direct (non-catalytic) inhibitory activity against thrombin, endoluminal surfaces coated with the direct (non-catalytic) thrombin inhibitor hirudin were chosen as a model for comparison in the animal experiments. Control experiments employing equal amounts of non-covalently linked AT+UFH bound to the surface were not possible given the much greater reactivity of AT for the epoxide groups compared to UFH. As shown in Table 12 and 13, surfaces coated with UFH had decreased surface density and an even more reduced $^{125}$I-AT binding (with, as expected, only non-direct antithrombin activity) compared to ATH-coated surfaces.

Figure 30:
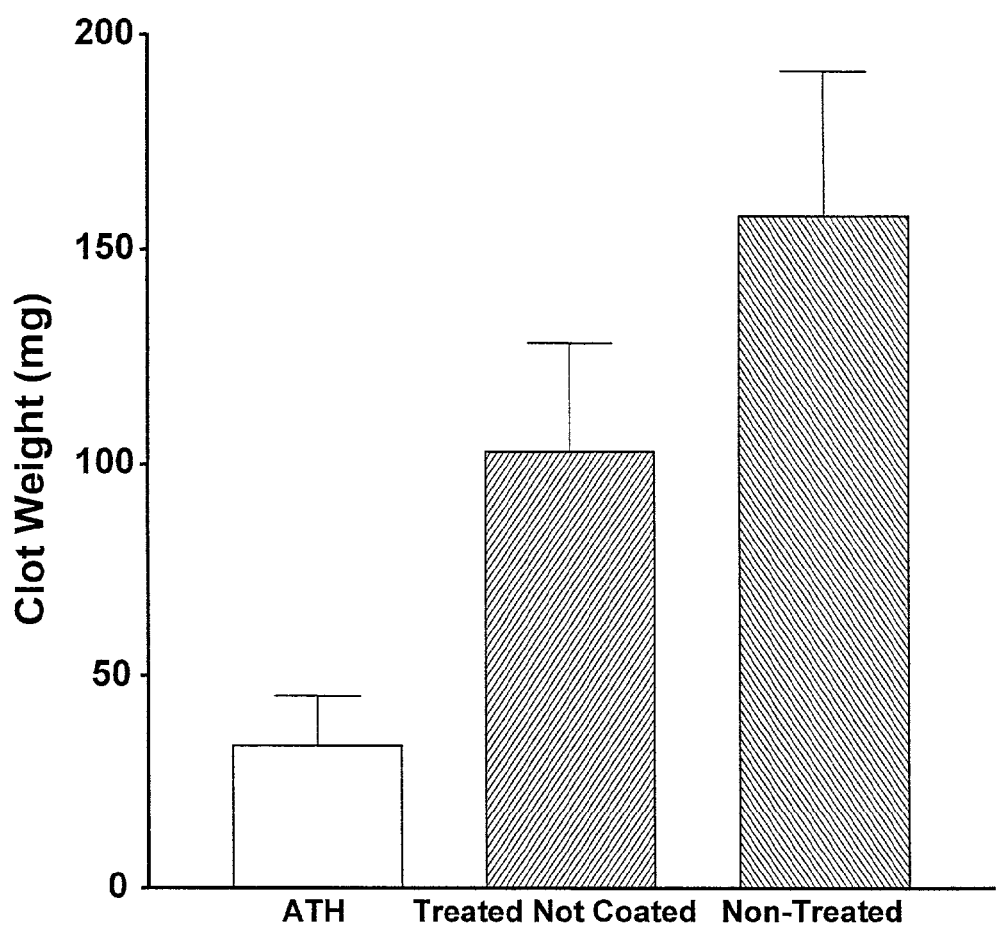
FIG. 30 Effect of antithrombin-heparin covalent complex (ATH) coating on clot formation on endoluminal grafts inserted into the jugular veins of rabbits. Polycarbonate urethane grafts (non-treated, treated with NaOCl followed by allyl glycidyl ether (but not coated with protein), or coated with ATH) were implanted into the jugular veins of anesthetized rabbits. After 3 hours, the grafts were explanted and the difference in graft weight due to clot formation determined.
Figure 31:
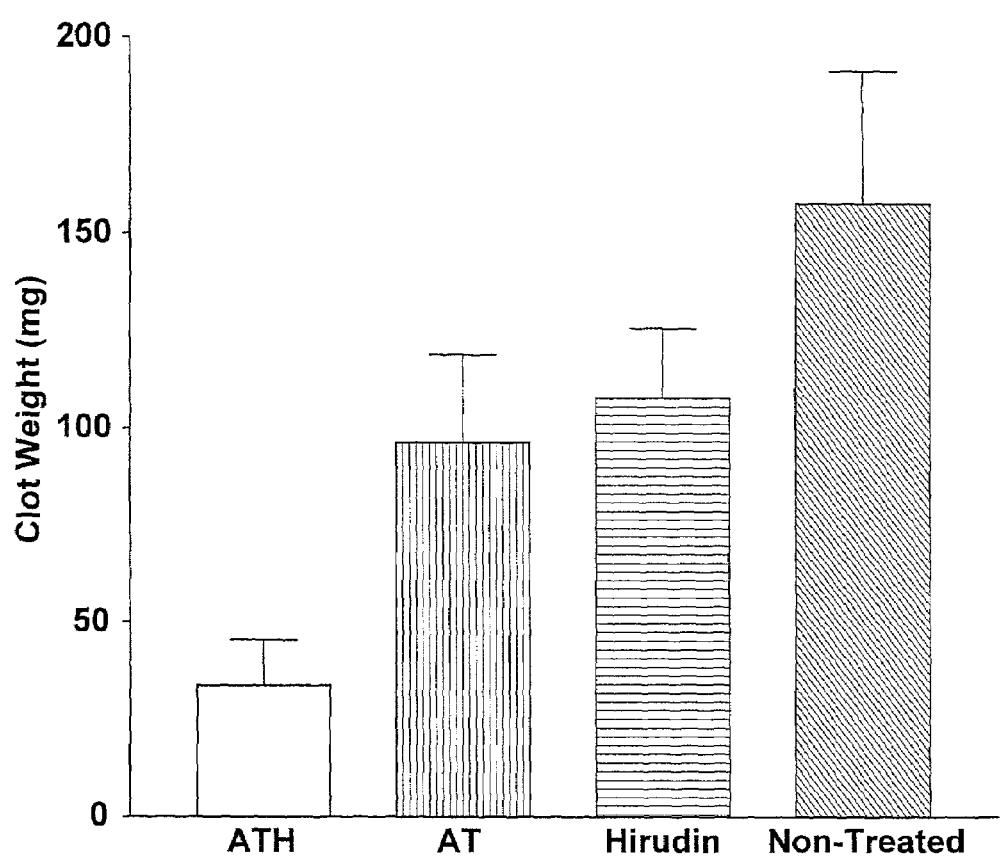
FIG. 31 Comparison of the effects of different coatings on the amount of clot formed on endoluminal grafts in vivo. Polycarbonate urethane grafts were coated with either anti-thrombin-heparin covalent complex (ATH), antithrombin (AT) or Hirudin. Grafts were inserted into the jugular veins of anesthetized rabbits. After 3 hours, the grafts were explanted and the difference in graft weight due to clot formation determined.

Endoluminal grafts were deployed into the external jugular vein of rabbits and, after being left in situ for 3 hours, the increase in weight of the endoluminal graft due to clot formation was measured. FIG. 30 shows the clot weight generated on surfaces that were either; coated with ATH, treated with NaOCl and allylglycidyl ether+Na$_2$S$_2$O$_8$ but not coated or given no treatment. ATH coated tubing showed significantly less clot generation than the weight of the clot formed within both the non-treated surface and the treated but non-coated surface, indicating that the reduction in clot weight generated by ATH grafts was not due to the surface activation process. The significant improvement in patency of ATH-coated grafts compared to untreated grafts is likely due to a combination of direct and catalytic thrombin inhibitory activities of the conjugate. The degree of ATH's anticoagulant effect was further investigated. The clot weights generated on grafts coated with ATH, AT alone or hirudin are shown in FIG. 31. Data for non-treated tubing was included for comparison. It can be clearly seen that the ATH modified surface showed a significant decrease in clot generation compared to the other surfaces. Since the AT coated surface showed a high clot generation, similar to that of the non-treated surface, it can be concluded that the heparin moiety of ATH is a critical part of its anticoagulant effect. Furthermore, statistical analysis showed that the weight of the clot generated in the ATH coated graft tubing was significantly less than the weight of the clot generated within the hirudin coated graft (p=0.03 with a 1 tail Student's t test).

Figure 32:
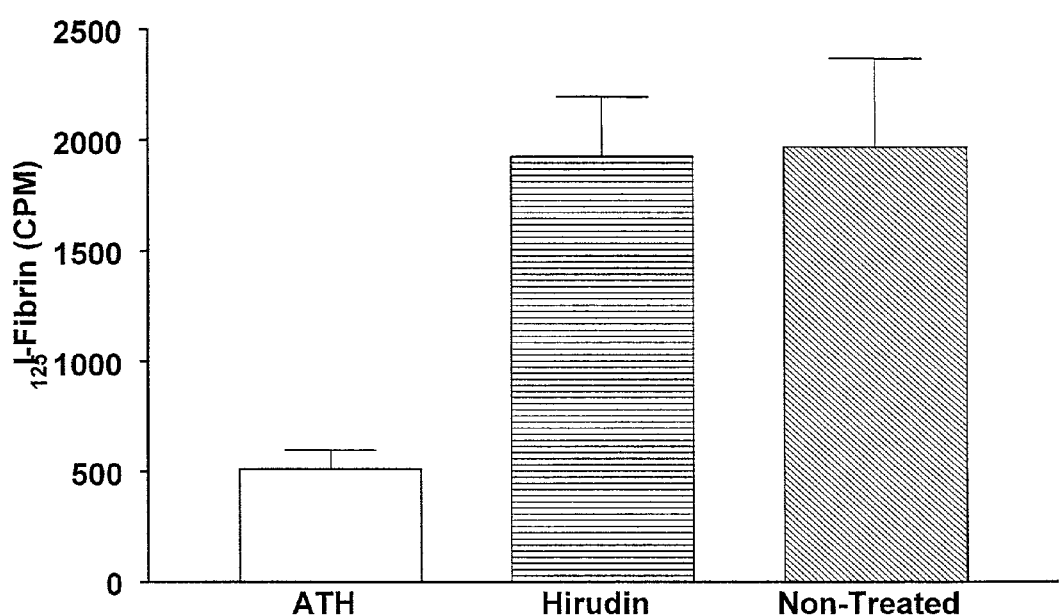
FIG. 32 Comparison of antithrombin-heparin covalent complex (ATH) and Hirudin coating of endoluminal grafts on fibrin accretion. Grafts were inserted into the jugular veins of anesthetized rabbits injected with $^{125}$I-fibrinogen. After 3 hours, the grafts were explanted and the amount of $^{125}$I-fibrin accreted onto the tubing was measured.

FIG. 32 shows the radioactivity of $^{125}$I-fibrin measured from the clot bound to the surfaces. Similar to the result of FIG. 31, the ATH modified surface had decreased $^{125}$I-Fibrin accretion compared to that of the other surfaces. This finding is important since it indicates that thrombin generating activity (which, in turn, converts fibrinogen to fibrin) is significantly reduced on the ATH-coated surface.

In order to investigate the effect of the grafts on systemic coagulant activity within the circulation, markers of thrombin generation (TAT) were measured in plasma from venous blood samples taken distal to the location of the graft. Table 14 lists the results. The data showed that ATH was considerably more effective in regulating thrombin generation compared to hirudin-coated or non-treated surfaces. While the non-treated surface and the hirudin coated surface had an increase in plasma TAT concentration compared to the average concentration in the blood before insertion of the graft, the ATH coated surface had plasma TAT concentrations which were similar to or lower than the starting background level. Since it has been shown previously that the direct inhibition of thrombin by ATH is extremely rapid (Chan A K, et al, J Biol Chem 1997; 272: 22111–22117; Berry L, et al J Biol Chem 1998; 273: 34730–34736), the delay in appearance of circulatory TAT in animals with the ATH modified surface, may be due to rapid inhibition of the small amounts of thrombin formed initially around the graft. Inhibition of the initial thrombin generated would block thrombin mediated feedback activation of the coagulation cascade (Ofosu F A, et al, Biochem J 1987; 243: 579–588.). The superior antithrombin activity by ATH may be due to the conjugation of AT to heparin, since the reaction step of AT-heparin binding in the thrombin inhibition mechanism (which has been shown to be rate limiting (Pletcher C H, et al, J Biol Chem 1982; 257: 5342–5345)) is not required by ATH.

Figure 33:
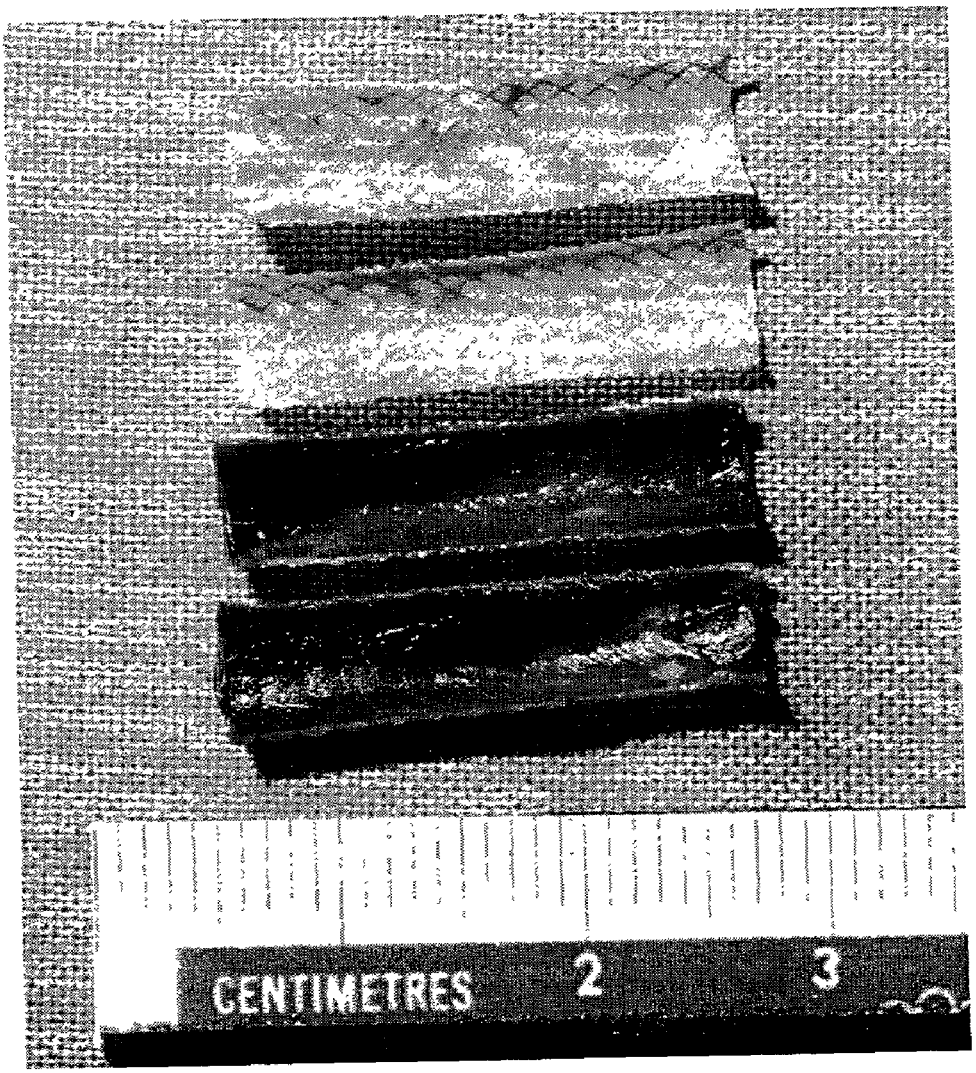
FIG. 33 Effect of antithrombin-heparin covalent complex (ATH) coating on performance of polycarbonate urethane grafts. Grafts that were present in the jugular veins of anesthetized rabbits for 3 hours were rinsed and cut longitudinally for inspection. The two cut pieces for ATH coated and uncoated grafts are shown at the top and bottom of the figure, respectively.

Finally, inspection of explanted ATH-coated tubing showed that the graft had a markedly increased antithrombotic activity. The difference in the performance of ATH-coated graft tubing compared to non-treated grafts can be seen in FIG. 33.

Conclusion

ATH-coated surfaces showed high graft density ($1.98 \times 10^{-7} \pm 6.4 \times 10^{-8}$) compared to Hirudin coated surfaces ($9.7 \times 10^{-9} \pm 1.3 \times 10^{-9}$) or heparin-coated surfaces ($3.14 \times 10^{-8} \pm 1.7 \times 10^{-8}$). ATH-grafts can be stored for over two months at 4° C. after ATH is attached to the surface. Furthermore, ATH maintained both non-catalytic antithrombin activity (as evidenced by direct in vitro thrombin inhibition) and indirect antithrombin activity (as evidenced by a significant number of catalytic $^{125}$I-AT binding sites ($\geq 66 \times 10^{-8} \pm 2.0 \times 10^{-9}$ moles/m$^2$), after it was attached to the polycarbonate urethane. Polycarbonate urethane endoluminal grafts coated with ATH induced significantly less clot formation compared to either hirudin coated, AT coated or non-treated grafts in the animal model described. Thus, ATH appears to be a good candidate for coating cardiovascular devices, such as endoluminal grafts, with high levels of substitution and significant long-term blood-compatibility.

Example XI

Inhibition of Fibrin-Bound Thrombin by a Covalent Antithrombin-Heparin Complex Experimental Procedures Materials—All reagents were of analytical grade. Human AT was from Bayer (Mississauga, ON, Canada) and UFH was from Sigma (grade I-A, Na salt, 15000 average molecular weight, from porcine intestinal mucosa (Mississauga, ON, Canada)). DEAE Sepharose Fast Flow, Sephadex G-200 and cyanogen bromide-activated Sepharose were from Amersham Pharmacia Biotech (Uppsala, Sweden).

Plasminogen free human fibrinogen, human IIa and human factor Xa (Xa) were from Enzyme Research Laboratories (South Bend, Ind., USA). The IIa chromogenic substrate N-p-tosyl-gly-pro-arg-p-nitroanilide (tGPR-pNA), hexadimethrine bromide (polybrene), gly-pro-arg-pro-amide (GPRP-NH$_2$), gelatin agarose and butyl agarose were from Sigma. S-2288 was from DiaPharma (West Chester, Ohio, USA). Na$^{125}$I was from New England Nuclear (Mississauga, ON, Canada) and IODO-BEADS® iodination reagent was from Pierce (Rockford, Ill., USA). IIa with reduced binding affinity for H (designated RA-IIa, with exosite II mutations arg$^{93}$: ala, arg$^{97}$: ala, and arg$^{101}$: ala (Ue, J., et al, 1994, J. Biol. Chem 269, 17965–17870) was from Charles T. Esmon, Howard Hughes Medical Institute, Oklahoma City, Okla., USA. Low molecular weight heparin (LMWH) was obtained from UFH by gel filtration on Sephadex G-200 to get a small molecular weight cut. The LMWH was recycled on the gel filtration column to obtain a fine fractionation with H of 1000–4000 Da molecular mass.

High Affinity and Low Affinity Heparin—Unless otherwise stated, all kinetics experiments were carried out using heparin (H) with high affinity for AT. H with high affinity for AT was prepared by Sepharose-AT chromatography of UFH. Sepharose-AT was prepared by reaction of AT with cyanogen bromide-activated Sepharose according to the manufacturer's instructions (approximately 2–5 mg AT per mL of packed gel). UFH (10 mg in 1 mL of 0.05 M Tris-HCl 0.15 M NaCl pH 7.4 buffer) was loaded onto a 50 mL column, that was pre-equilibrated with buffer. Unbound, low affinity heparin was eluted with 2 column volumes of buffer. The unbound fraction containing low affinity heparin was exhaustively dialyzed versus H$_2$O, freeze-dried and stored dry at 23° C. for future use. Bound high affinity H was eluted from the column with 90 mL of 2 M NaCl; 3 mL fractions being collected. H-containing fractions were identified (by Alcian blue staining—Chan A k et al, J. Biol Chem. 272, 22111–22117), pooled and treated with 3 volumes of ethanol. Precipitated material was dissolved in starting buffer and rechromatographed on the column. After repeating the chromatographic procedure 3 times, the final ethanol precipitate was redissolved in 0.15 M NaCl, and the H concentration in the resultant solution determined by a protamine sulfate turbidimetric assay (Hatton M W, et al, Thromb Res 1978; 13: 655–670). The high affinity H had an anti-Xa activity of 280 units/mg H and a mass average molecular mass of 15000 Da, as determined by high-pressure liquid chromatographic gel filtration (Cosmi B et al, Circulation 95: 118–124).

Preparation of Covalent Complexes—Synthesis of covalent antithrombin-heparin complex (ATH) has been described previously (see above and Chan A K 1997, J. Biol. Chem 272, 22111–22117). Briefly, AT (1.2 mg/mL)+UFH (66.7 mg/mL) were heated in 0.02 M phosphate 0.15 M NaCl pH 7.3 buffer at 40° C. for 14 days, followed by addition of 1 volume of 0.5 M NaBH$_3$CN per 9 volumes of reaction mixture and a further heating at 37° C. for 5 hours. ATH was purified by a 2-step procedure utilizing butyl agarose hydrophobic chromatography to remove excess UFH, followed by DEAE Sepharose Fast Flow anion exchange chromatography to remove unreacted AT. The resultant ATH eluted from DEAE Sepharose Fast Flow was concentrated to 8.77 mg/mL AT (ATH protein extinction coefficient at 280 nm=0.75), 2.23 mg/mL H (protamine sulfate turbidimetric assay) using pressure dialysis versus 0.02 M phosphate 0.15 M NaCl pH 7.3. Concentrated ATH was stored at −80° C. ATH was also prepared by incubating AT with LMWH (molecular mass 1000–4000 Da) and purifying the product (ATLMWH) as described above. AT conjugated to a low affinity heparin (ATLAH) was prepared in a similar manner. Also, ATH containing the fraction of LMWH with low affinity for Sepharose-AT (ATLMWLAH) was obtained by taking the low molecular weight fraction of ATLAH chromatographed on Sephadex G-200.

Preparation of Soluble Fibrin Monomer—Contaminating fibronectin was removed from the commercial fibrinogen by 2 incubations of 15 mL of 130 μM fibrinogen (molecular mass 340000 Da) with 5 mL of gelatin agarose for 30 min, followed by centrifugation and collection of the fibrinogen containing supernatant. Fibrinogen concentration were determined by absorbance at 280 nm using $\epsilon \epsilon^{1\%}$=15.1 (Hogg P J and Jackson C M, 1989, Proc. Natl. Acad, Sci. 86,3619) (after correction for light scatter at 320 nm using the equation corrected A$_{280}$=A$_{280}$−1.7×A$_{320}$ (Bloom, J W, et al, 1979, Biochem 18, 4419–4425). Soluble fibrin monomer was prepared by the following method. Purified fibrinogen (60–100 μM) was incubated with IIa (2 nM) at 37° C. for 4–6 hours, followed by centrifugation at 2000 g for 5 min. The fibrin polymer pellet was placed in a dialysis bag (12000–14000 molecular weight cut-off), dialyzed versus H$_2$O(4° C.) to remove fibrinopeptides A and B and then further dialyzed versus 0.02 M acetic acid until the fibrin dissolved (~8 hours). Concentration of the soluble fibrin in solution was obtained by absorbance at 280 nm and using a molecular weight of 340000 and $\epsilon^{1\%}$=14.0 (Lewis, S D et al, 1985, Biochem 24: 6772–6777). Typically, 100 μM soluble fibrin was obtained and stored at −80° C. Soluble fibrin in 0.02 M acetic acid was neutralized with 40% v/v 1 M Tris-HCl pH 7.5 and polymerization blocked with 5 mM GPRP-NH$_2$ (Kawasaki, K. et al Chem Pharm. Bull 40, 3253–3260) to give soluble fibrin monomer for kinetics experiments.

Measurement of Rate of Protease Inhibition—The rates of IIa, RA-IIa and Xa reactions with inhibitors were measured discontinuously under pseudo first-order conditions (molar ratio of enzyme:inhibitor was ≦0.1). Twenty nM IIa, 40–120 nM RA-IIa or 40 nM Xa (at 2-times final reaction concentration) were incubated in up to 8 separate 96-well round-bottomed microtiter plate wells (Fisher, Nepean, ON, Canada) for 5 min at 23° C. in 0.02 M Tris-HCl 0.15 M NaCl 0.6% polyethylene glycol 8000 pH 7.4 (TSP) containing 0.01 M GPRP-NH$_2$±H (0–10000 nM)±fibrin monomer (0–4000 nM). An equal volume of either AT+H, ATH, ATHLM, ATLMWH or ATLMWLAH (all at≧10 times the enzyme concentration) was added to each well at time intervals ranging from 2–600 s. Termination of the reactions was carried out by simultaneous addition to each well of 200 μL of a 10 mg polybrene/mL solution containing 222 μM tGPR-pNA substrate. Remaining enzyme activity was calculated from the rate of substrate hydrolysis determined by measurement of the change in absorbance at 405 nm using a Spectra Max 340 Microplate Reader (Molecular Devices, Menlo Park, Calif., USA). The pseudo first-order rate constants for the inhibition reactions were calculated according to equation 1.

$$V_t/V_o = e^{-k_1 t} \quad \text{(equation 1)}$$

where: $V_o$=enzyme activity at time=0 s, $V_t$=enzyme activity at time=t, and $k_1$=the pseudo first-order rate constant. Apparent second order rate constants ($k_2$) were calculated by dividing $k_1$ values by the inhibitor concentrations. Due to the extremely rapid rates of enzyme inhibition at the concentrations of inhibitor and enzyme used, some reactions were carried out in the presence of S-2288, which acted as a competitive inhibitor (Griffith, M J, 1982, J. Biol. Chem. 257:7360–7365). In cases where competitive inhibitor (S-2288) was used, the pseudo first-order rate constant of inhibition was calculated according to equation 2.

$$k_1 = (k_{app}) \times (1 + [S]/Km) \quad \text{(equation 2)}$$

where: $k_{app}$=the apparent pseudo first-order rate constant, [S]=the concentration of competitor and Km=the Michaelis-Menton constant of enzyme for S-2288 (3 μM for thrombin, 2000 μM for Xa). In a few experiments, pseudo first-order rate constants were calculated using equation 2 and compared to those calculated using equation 1 where direct measurement in the absence of S-2288 could be made using the same inhibitor concentrations. Equations 1 and 2 were confirmed to give equivalent values in this system. Effects of fibrin or H on the second-order rate constants for reaction of IIa, RA-IIa or Xa with ATH were determined. Effects on rates for similar reactions with AT+H, ATLMWH, ATLAH or ATLMWLAH were measured and comparisons made.

Binding Experiments—Detailed investigations of the complexes formed during combination of ATH, fibrin and/or IIa were carried out to determine the interactions that occur between components in the system. Buffer (0.02 M Tris-HCl 0.15 M NaCl 0.1% polyethylene glycol pH 7.4)±fibrin monomer (4000 nM final concentration combined with 5 mM (final) GPRP-NH$_2$)±UFH (495 nM final concentration) ±inhibitor (either ATH or AT (17 nM final))±IIa (17 nM final) were mixed and incubated at 23° C. for 10 min. In different experiments, ATH, AT or IIa were spiked with $^{125}$I-labeled ATH, AT, or IIa, respectively (proteins labeled using Na$^{125}$I and IODO-BEADS®, according to the manufacturer (Pierce)). After incubation, the mixtures were combined with either 2-mercaptoethanol containing SDS sample buffer or 5% glycerol in buffer. Two-mercaptoethanol/SDS samples were heated at 100° C. for 1 min and run on SDS PAGE gels according to the method of Laemmeli et al (Nature, 1970, 227:680–685). Alternatively, samples in 5% glycerol only were run on non-denaturing gels (no SDS). Gels were dried and autoradiography performed. The degree of migration of radiolabeled species in the non-denaturing (native) gels indicated covalent and non-covalent associations occurring between the radiolabeled molecules and other non-radioactive components in the incubation mixtures. Degree of migration in the reduced SDS PAGE gels verified the formation of covalent complexes between radiolabeled molecules and non-radioactive molecules in the incubation mixtures.

Fluorescence Studies—Experiments were carried out to evaluate alterations in physical properties occurring during interaction of ATH with fibrin-bound IIa. Fluorescence spectral determinations were used to assess any changes in environment (due to change in conformation or binding) of tryptophanyl (and tyrosinyl) residues in the ATH/IIa/fibrin polypeptide chain(s). All fluorometric determinations were made, with rapid stirring in 1×1 cm quartz fluorescence cuvettes, in a cuvette chamber heated at 25° C., using a Perkin Elmer LS50B luminescence spectrometer. Experiments were performed in 0.02 M Tris-HCl 0.15 M NaCl pH 7.4 buffer. Intrinsic fluorescence measurements of the proteins were done using excitation at 280 nm (with a 290 nm filter). The excitation slit width was 10 nm and the emission slit width was 7 nm. Mixtures of IIa (400 nM final concentration)±ATH (400 nM final)±fibrin monomer (1000 nM final in the presence of GPRP-NH$_2$ (5 mM final)) in buffer were made and the fluorescence spectrum obtained within 10 min. Differences in fluorescence spectral profiles were noted due to addition of fibrin to IIa and/or ATH. Time course changes in peak fluorescence intensity (at 340 nm) were also recorded immediately after addition of the various mixture components.

Statistics—Data were compared for significant differences using either the students t-test (in the case of two groups) or by analysis of variance (ANOVA, for more than two groups). Upon finding a significant difference within several groups by ANOVA, testing between two groups within that set was carried out by t-test. A p value of <0.05 was considered significant and results were expressed as mean±SEM with n ≧2.

RESULTS

Inhibition of IIa by ATH or AT+H in the Presence of Fibrin

Figure 34:
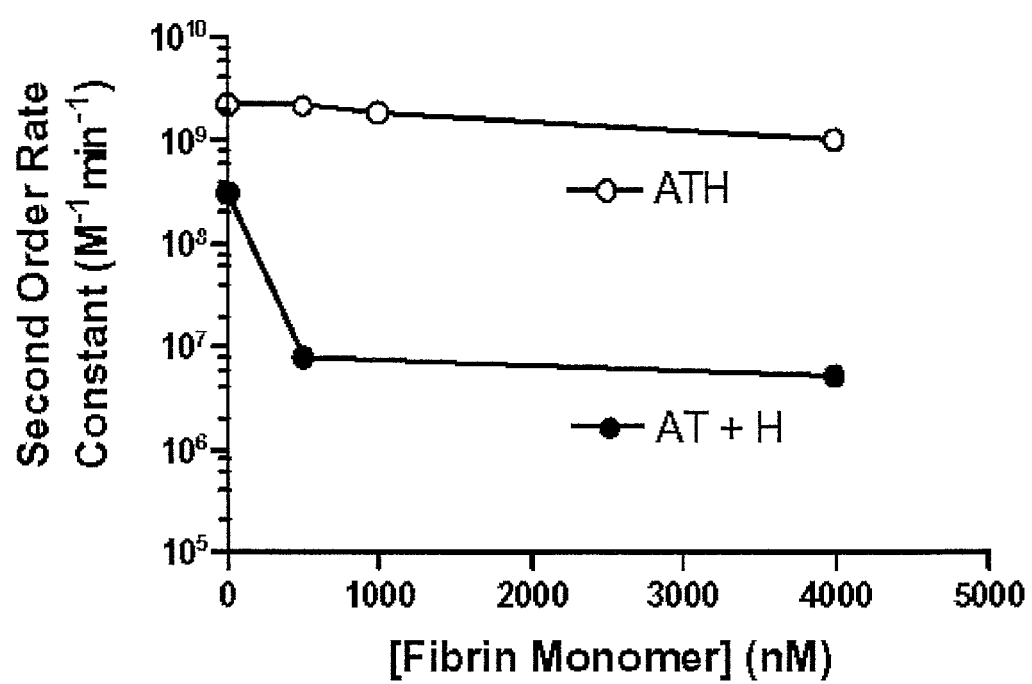
FIG. 34 is a graph showing the effect of fibrin on the rate of inhibition of thrombin (IIa) by either covalent antithrombin-heparin complex (ATH) or non-covalent mixture of antithrombin (AT) and heparin (H). Pseudo first-order rate constants were determined under pseudo-first order conditions. Apparent second-order rate constants ($k_2$) were calculated by dividing $k_1$ (rate of loss in IIa chromogenic activity) values by the inhibitor concentrations. The second order rate constant is plotted versus increasing concentration of fibrin monomer in solution. Values are means±SEM.
Figure 35:
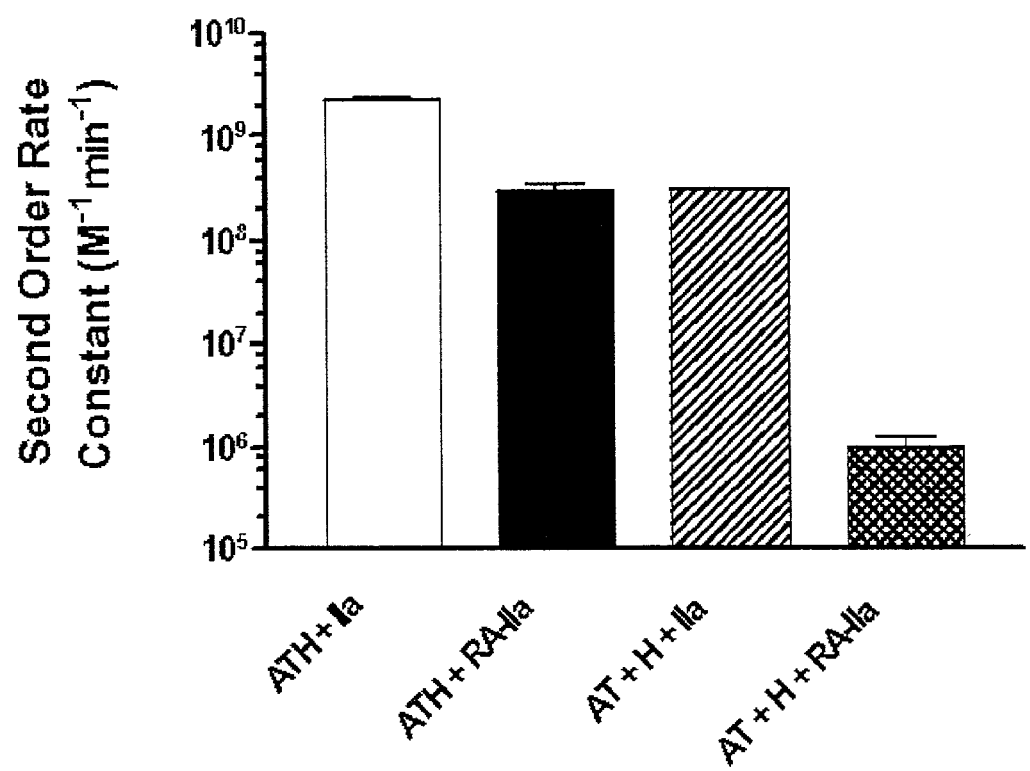
FIG. 35 shows a comparison of the rate of inhibition of thrombin (IIa) to that of a thrombin variant (RA-IIa) with either covalent antithrombin-heparin complex (ATH) or non-covalent mixture of antithrombin (AT) and heparin (H). Rates of inhibition of a thrombin variant (RA-IIa) that has reduced H-binding affinity were compared to that with α-thrombin (IIa). Pseudo first-order rate constants were determined under pseudo-first order conditions. Apparent second-order rate constants were calculated by dividing first-order rates by the inhibitor concentrations. Values are means±SEM.
Figure 36:
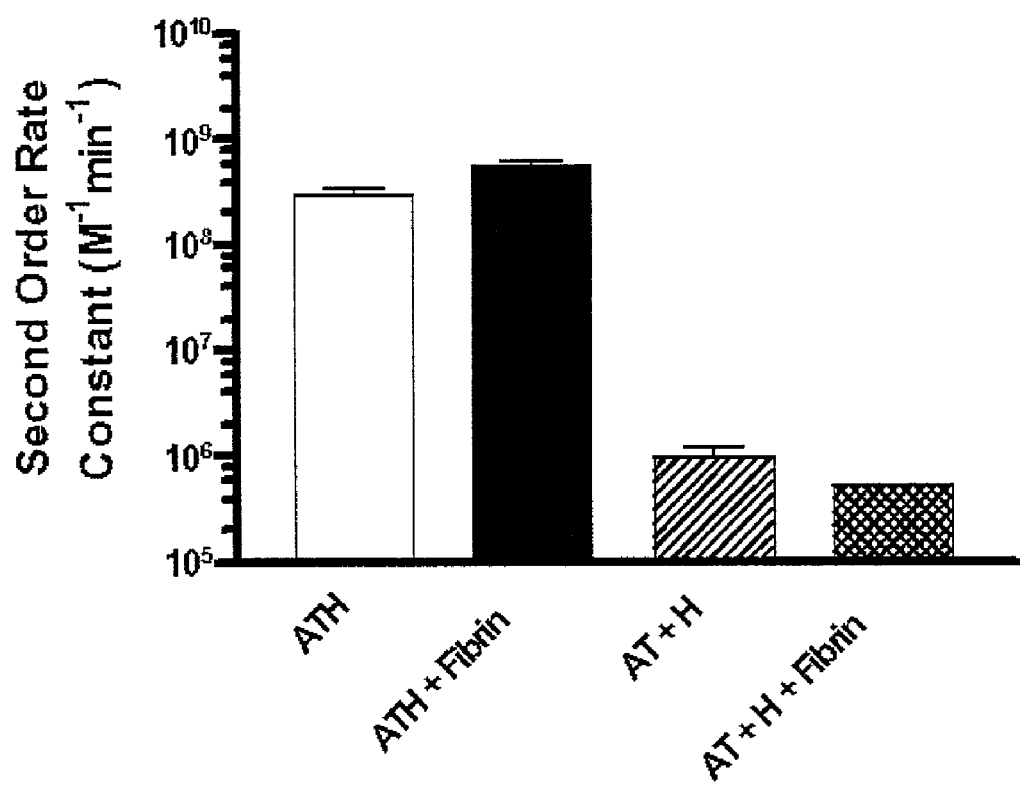
FIG. 36 shows the effect of fibrin on the rate of inhibition of a thrombin variant (RA-IIa) by either covalent antithrombin-heparin complex (ATH) or non-covalent mixture of antithrombin (AT) and heparin (H). The effect of fibrin on the rates of inhibition of a thrombin variant (RA-IIa) that has reduced H-binding affinity was studied. Pseudo first-order rate constants were determined under pseudo-first order conditions. Apparent second-order rate constants were calculated by dividing the first-order rate values by the inhibitor concentrations. Values are means±SEM.

ATH or non-covalent AT●H (AT bound to the fraction of UFH with high affinity to AT) were reacted for different times with IIa in the presence of varying concentrations of fibrin monomer (with added GPRP-NH$_2$ peptide to prevent polymerization) and the rates of reaction determined. Pseudo first-order rate constants ($k_1$) were calculated for ATH and the other inhibitors from the apparent pseudo first-order rate constant obtained from the measured disappearance of enzyme activity. Second-order rate constants ($k_2$) were calculated as $k_1$ divided by the inhibitor concentration. Rate values ($k_2$) for the reactions of IIa with either ATH or AT+H were plotted versus concentration of added fibrin. The results are shown in FIG. 34. Increasing fibrin concentration caused a decrease in the rate of IIa inhibition for both ATH and non-covalent AT+H mixture. However, the effect of fibrin on inhibition of IIa was significantly decreased for reactions with ATH compared to those with AT+H. Reaction rates for IIa inhibition by ATH were decreased up to 3-fold in the presence of 4 μM fibrin, while rates of IIa reaction with AT●H were reduced by 57-fold when fibrin was present (FIG. 34). Thus, fibrin monomer had 20 times as great an effect on inhibiting IIa reactions with AT●H compared to reactions with ATH. Results for the effects of fibrin on reaction rates of IIa+ATH and IIa+AT+H are summarized in Table 15. Inhibition of Xa by ATH was also studied. Addition of fibrin had minimal effect on Xa inhibition by ATH. Inhibition of RA-IIa by ATH or AT+H in the presence of fibrin In order to study the structural aspects of IIa that may be important for the differing effects of fibrin on reactions with ATH compared to AT+H, a IIa mutant with reduced binding to high affinity H (RA-IIa) was used. Direct reaction of RA-IIa with ATH was markedly slower than the corresponding reaction with IIa (FIG. 35). However, the rate of RA-IIa inhibition by AT+H mixtures was decreased (relative to rates of IIa+AT+H reaction) to an even greater degree than that of the corresponding reactions with ATH. Thus, while ATH reacted at a 7.6-fold slower rate with RA-IIa compared to IIa, reaction of AT+H with RA-IIa was more than 2 orders of magnitude slower than that with IIa (FIG. 36, Table 15). Increasing concentrations of H in the RA-IIa (10 nM)+AT (100 nM)+H (100 nM or 500 nM) reaction did give a several-fold increase in rate (6.68×10$^5$M$^{-1}$min$^{-1}$ and 2.0× 10$^6$ M$^{-1}$min$^{-1}$ for 100 nM H and 500 nM H, respectively), indicating that RA-IIa still retained some H-binding ability (albeit greatly reduced). When fibrin was added to the system, the rate of RA-IIa inhibition by AT+H was only moderately decreased compared to reactions in the absence of fibrin (FIG. 36). Alternatively, there was no reduction in reaction rate when fibrin was added to reactions of RA-IIa+

ATH (FIG. 36, Table 15). In comparison, ATH was more reactive with the RA-IIa mutant than AT●H, regardless of whether fibrin was present.

Effect of Added H on the Inhibition of IIa by ATH with or without Fibrin

Figure 37:
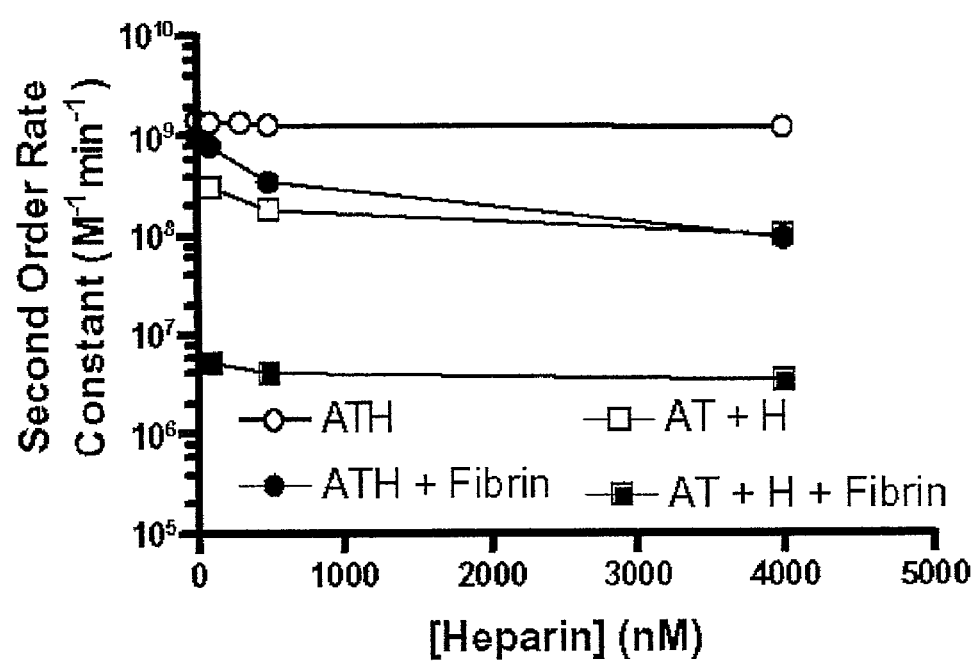
FIG. 37 shows the effects of heparin (H) and fibrin on the rate of inhibition of thrombin (IIa) by either covalent anti-thrombin-heparin complex (ATH) or non-covalent mixture of antithrombin (AT) and heparin (H). The effect of H concentration on the rate of thrombin inhibition was investigated in the presence or absence of fibrin. Pseudo first-order rate constants were determined under pseudo-first order conditions. Apparent second-order rate constants were calculated by dividing the first-order rate values by the inhibitor concentrations. Values are means±SEM.

Further experiments were conducted to evaluate the importance of the H moiety of ATH for the inhibition of fibrin-bound IIa. Reactions of IIa+ATH were carried out in the presence or absence of added H and/or fibrin. Rate of IIa inhibition by ATH was decreased by only 10% when equimolar H was added (FIG. 37). Addition of a 40-fold molar excess of H caused a reduction of 1.3-fold in the reaction velocity. Alternatively, when 4000 nM fibrin was present in reactions containing 10 nM IIa+100 nM ATH, addition of 4000 nM H caused a 12-fold decrease in rate of IIa inhibition compared to that in corresponding experiments without added H (FIG. 37). Thus, addition of a significant molar excess of exogenous H decreased the rate of inhibition of IIa by ATH to a much greater degree in the presence of fibrin than in the absence of fibrin. In the case of IIa reaction with AT, a large molar excess of H gave a significantly smaller effect in rate reduction (FIG. 37).

Heparin Chain Length and Pentasaccharide Dependence of ATH Reaction With IIa

Figure 38:
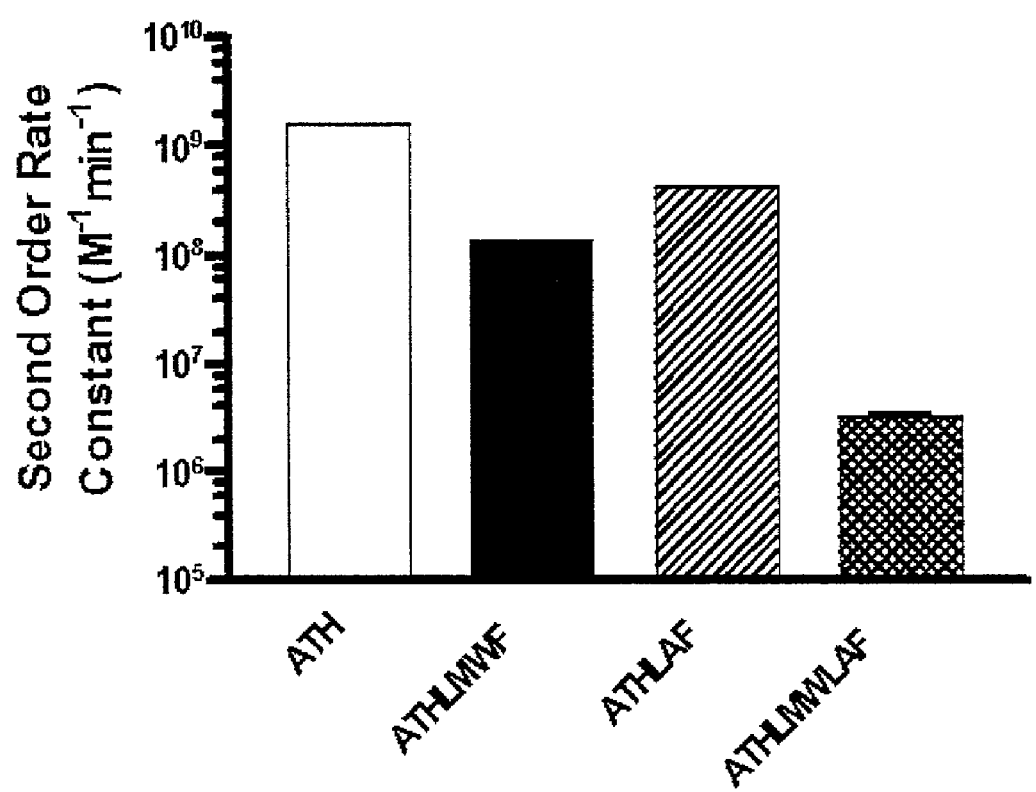
FIG. 38 shows the influence of heparin (H) chain length and antithrombin (AT) binding site (pentasaccharide) content on inhibition of thrombin (IIa) by covalent antithrombin-heparin complex. Covalent antithrombin-heparin complex (ATH) was compared with covalent complexes of AT and a low molecular weight heparin fraction (ATLMWH), AT and a heparin fraction with low AT-affinity (ATHLA), or AT and a low molecular heparin fraction with low AT-affinity (ATLMWLAH). Inhibition reactions with IIa were studied. Pseudo first-order rate constants were determined under pseudo-first order conditions. Apparent second-order rate constants were calculated by dividing the first-order rate values by the inhibitor concentrations. Values are means±SEM.

Further experiments were carried out to investigate the effect of H chain length and pentasaccharide content in ATH on the inhibition of IIa. In comparison with ATH, the rates of IIa reaction with ATH containing short H chains (ATLMWH) or ATH prepared using the fraction of UFH with low affinity for AT (ATLAH) were significantly lower (FIG. 38). In particular, inhibition of IIa with ATHLMWH was ~12-fold slower than the corresponding reaction with ATH. However, inhibition of IIa by ATH that contained a low molecular weight fraction of low affinity heparin (ATLMWLAH) was reduced by 2 orders of magnitude compared to native ATH (>450-fold, FIG. 38). Therefore, both H chain length and AT affinity (pentasaccharide content) were critical for ATH reaction with IIa. In comparison, reaction rates of ATLMWH and ATLAH with Xa were also decreased compared to that with ATH ($k_2$ values for Xa inhibition by ATH, ATLMWH and ATLAH were $2.1 \times 10^8$, $1.2 \times 10^8$ and $2.1 \times 10^7$ $M^{-1}min^{-1}$, respectively). As expected, the reaction velocity of ATLMWH with Xa was much less decreased compared to the reaction of ATLMWH with IIa, given the fact that, unlike IIa, inhibition of Xa with AT+H does not require binding of the enzyme to the H chain (Hirsh, J, et al, 1998, Chest 114, 489S–510S).

Binding Experiments

Figure 39:
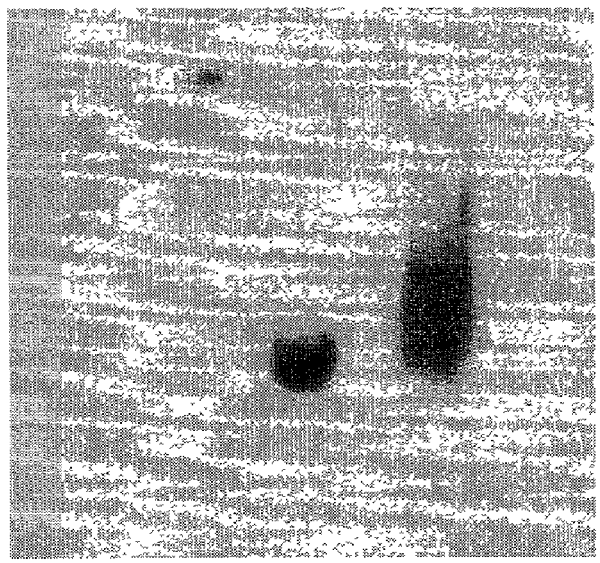
FIG. 39 shows a comparison of fibrin (Fn) binding to covalent antithrombin-heparin complex (ATH) with Fn binding to antithrombin (AT) in non-covalent mixtures of AT and unfractionated heparin (UFH). Solutions of $^{125}$I-labeled covalent antithrombin-heparin complex ATH) or $^{125}$I-labeled antithrombin (AT) mixed with unfractionated heparin (UFH) were prepared in the absence or presence of soluble fibrin monomer (Fn). Subsamples of the solutions were either mixed with 5% glycerol in buffer and electrophoresed on native gels under non-denaturing conditions (panel A) or heated for 1 min at 100° C. with 2-mercaptoethanol/SDS and electrophoresed on SDS gels under denaturing conditions (panel B). Autoradiograms of the dried gels are shown.
Figure 39:

Mixtures of ($^{125}$I-)ATH and fibrin monomer showed formation of non-covalent complexes on non-denaturing gels (FIG. 39A). The non-covalent nature of the complexes between ATH and fibrin was verified by the fact that the radiolabeled ATH could be dissociated from the fibrin on SDS gels under reducing conditions (FIG. 39B). In contrast, mixtures of ($^{125}$I-)AT+UFH+fibrin monomer showed no binding of AT to fibrin or UFH (AT migrated as free AT on native gels (FIG. 39A)). Control experiments with ($^{125}$I-)AT+UFH resulted in the expected non-covalent complexes of AT●H (FIG. 39). Interaction of ATH with IIa±fibrin was investigated. Use of $^{125}$I-IIa showed that IIa formed a complex with fibrin monomer ($^{125}$I-IIa had a reduced rate of migration on a non-denaturing gel in the presence of fibrin compared to that of $^{125}$I-IIa alone (FIG. 40A)) which was non-covalent (dissociated on SDS PAGE to run at the same position as that of $^{125}$I-IIa alone (FIG. 40B)). In the absence of fibrin, ATH formed a 1:1 complex with ($^{125}$I-)IIa (FIG. 40A) that was verified to be covalent under the dissociating conditions of an SDS PAGE gel (FIG. 40B). However, combination of ATH with ($^{125}$I-)IIa in the presence of fibrin monomer gave a $^{125}$I-IIa band that migrated at an intermediate position between that of $^{125}$I-IIa+ATH and $^{125}$I-IIa+fibrin on non-denaturing gels (FIG. 40A). $^{125}$I-IIa was determined to exist as a covalent complex with ATH when mixed with ATH+fibrin, since the radiolabel migrated as a high molecular weight smear on denaturing SDS PAGE (similar to incubations of ATH+($^{125}$I-)IIa in the absence of fibrin (FIG. 40B)). Therefore, although ($^{125}$I-)IIa reacted to form inhibitor complexes with ATH in the presence of fibrin, covalent $^{125}$I-IIa-ATH continued to interact with the fibrin under physiological conditions. Addition of exogenous H in experiments with $^{125}$I-IIa+ATH+fibrin decreased the yield of fibrin-bound $^{125}$I-IIa-ATH. Variation of the order of addition of ATH and $^{125}$I-IIa to the fibrin made no significant difference in outcome of the experiments.

Fluorescence Studies

Mixture of equimolar quantities of IIa and ATH gave a combined intrinsic fluorescence at 340 nm which dropped dramatically over time, indicative of changes in environment of tryptophanyl groups on IIa and/or ATH occurring during covalent IIa-ATH inhibitor complex formation. This rapid fluorescence decrease occurring when covalent IIa-ATH complexes were forming was observed in the presence or absence of fibrin. Spectral emission scans of various combinations of ATH, IIa and fibrin were carried out. In the absence of fibrin, ATH+IIa mixtures gave a fluorescence profile, at final equilibrium, that was significantly less than the sum of the individual fluorescence spectra for the ATH and IIa before mixing (FIG. 41A). Even more striking was the observation that addition of fibrin (1000 nM) to ATH (400 nM)+IIa (400 nM) resulted in an emission peak which was not increased compared to that of fibrin+IIa or fibrin+ATH (FIG. 40B). Thus, ternary complexes of fibrin●IIa●ATH had a significantly altered environment for fluorescent residues in the polypeptide chains compared to fibrin●IIa or fibrin●ATH complexes.

DISCUSSION

Treatment of patients with thrombosis requires the control of IIa generation and the subsequent action of thrombin on fibrinogen to form fibrin leading to clot formation. IIa inhibition is critical for reduction of prothrombotic complications since active IIa promotes its own formation by feedback activation of coagulation cascade factors V, VIII and XI (Ofosu, F, et al, Semin. Thrombos, Haemostas 22, 303–308; Naito, K, and Fujikawa, K, 1991, J. Biol. Chem. 266, 7353–7358; Gailani, D., and Broze, G. Jr. 1991, Science 253, 909–912). Both UFH and LMWH have been successfully used for the amelioration of IIa-induced coagulation in vivo. Inhibition of IIa by H relies on the activation of the plasma inhibitor AT (Gettins, P. et al, J. Biol Chem. 267, 21946–21953), followed by binding of the AT●H complex to IIa through the H moiety (Jordan, E. et al, J. Biol Chem. 255, 10081–10090). Reaction of AT and IIa in the AT●H●IIa complex results in an inactive covalent AT-IIa product (Jin, L, et al, 1997, Proc. Natl, Acad, Sci USA 94, 14683–14688, Carrell, R. W. and Owen M C, 1985, Nature 317, 730–732) that dissociates from the GAG chain (Hatton, M W et al, 1978, Throm Res. 13, 655–670, Byun, Y et al, 1996, J. Biomed. Mater. Res. 30, 423–427). Thus the H molecule is free for catalysis of another AT+IIa reaction.

It has been shown previously that after fibrin generation has occurred, IIa can remain bound to the fibrin molecule through the anion binding exosite I of the enzyme (Hsieh, K, 1997 Thromb Res 86, 301–316; Guillin M C et al, Thromb. Haemost, 74, 129–133). Furthermore, IIa that is bound to fibrin has been shown to retain procoagulant enzymatic activity (Eisenberg, P et al, 1993 J. Clin. Invest. 91, 1877–1883; Prager, N A et al, 1995, Circulation 92, 962–967; and Weitz J I, et al, 1990, J. Clin Invest, 86, 385–391). However, fibrin-bound IIa is resistant to inhibition by either AT●UFH or AT●LMWH complexes (Hogg P J and Jackson C M, 1989, Proc. Natl. Acad, Sci. USA 86, 3619–3623; Bendayan, P. et al, 1994 Thromb. Haemostas. 71, 576–584). The mechanism for protection of IIa inhibition by fibrin involves initial formation of a ternary fibrin●IIa●H complex (Hogg, P J and Jackson, 1960, J. Biol. Chem. 265:248–255; Hogg P J, et al, 1996, J. Biol. Chem. 271:26088–26095). In fact, it has been shown that binding of free H (dissociated from AT) to fibrin can actually recruit IIa to the fibrin surface (Hogg, P J, and Jackson, 1990, J. Biol. Chem. 265:241–247). In this trapped form where fibrin is bound to IIa's anion-binding exosite I and H is bound to IIa's anion-binding exosite II (Hogg, P J and Bock, P E, 1997, Thromb. Haemostas. 77:424–433), the enzyme is unable to interact with approaching AT●UFH or AT●LMWH complexes. Thus, it is apparent that bridging of IIa and fibrin by free H is a critical step in preventing the successful pacification of fibrin-bound IIa and prevention of clot extension.

To address the limitations of H inhibition of fibrin-bound IIa, we have developed an active, covalent complex of AT and H has been developed (Chan, A K, et al, J. Biol. Chem. 272:22111, 1997). We showed that ATH can react rapidly with IIa and Xa in vitro (Chan, A K, et al 1997 supra; Berry, L., et al 1998, supra). Results from experiments in vivo indicated that ATH might be capable of facile reaction with fibrin-bound IIa, since intravenous administration of low dose ATH caused a reduction in size of venous thrombi compared to an increase in clot size with treatments using the same molar concentrations of non-covalent AT+UFH. Given the antithrombotic potency of ATH and the fact that the GAG chain in ATH could not dissociate to form a ternary fibrin●H complex, we decided to study the effects of fibrin on the inhibition of IIa by ATH in vitro were studied.

Reactions were carried out with IIa+inhibitors, with or without the presence of varying concentrations of fibrin (maintained as a monomer by the addition of GPRP-NH$_2$). Reactions were stopped with polybrene at various time intervals, the residual IIa activity determined with chromogenic substrate and the rate of IIa neutralization calculated (second order rate constant, k$_2$). Although reaction of IIa by ATH was impaired by fibrin monomer, the inhibition by fibrin was only 4% of that observed for IIa+AT●H (FIG. 34). The result was consistent with preliminary studies on the effect of fibrin on IIa inhibition by ATH (Becker, D L, et al 199, J. Biol, Chem. 274:6226). This finding was in agreement with the suggestion that free H (not sterically hindered by covalently attached AT) was required to form a fibrin●IIa●H complex that prevented the approach of AT-bound H. It was possible that AT●H was unable to react with the IIa in fibrin●IIa●H complexes due to an inability of the approaching H moiety to bind to IIa's exosite II. Therefore, unlike the H in AT●H (which dissociates to form a complex with IIa●fibrin) the GAG portion of ATH may assist in reaction with fibrin-bound IIa by bridging the AT to IIa's anion exosite. In order to test the importance of H binding to IIa (when bound to fibrin), experiments were conducted to measure the effect of fibrin on inhibition of a mutant IIa with reduced H affinity (RA-IIa). While inhibition of RA-IIa by AT+H was 306 times slower than that with IIa, the reaction rate of RA-IIa+ATH was only decreased by 7.6-fold compared to IIa+ATH (FIG. 35, Table 15). This result suggested that because the AT in ATH is always activated, reactions with IIa are more rapid (rate-determining step of AT●H formation eliminated in the covalent complex); which partially moderates any problems with the bridging of IIa and AT by the heparin moiety. Further experiments with fibrin gave a similar trend where the rate of RA-IIa reaction with AT+H was decreased 2-fold when fibrin was present, compared to a mild increase in rate of inhibition of RA-IIa by ATH with fibrin (FIG. 36, Table 15). Since binding of H to IIa is a charge-dependent phenomenon, the reaction of IIa with ATH (±fibrin) was challenged by addition of exogenous H. The presence of equimolar H caused an approximate 10% reduction in rate of IIa inhibition by ATH. Furthermore, addition of up to 40-fold molar excess caused approximately 20% decrease in rate of IIa reaction with ATH (FIG. 37). Thus, there was only a moderate effect on inhibition of IIa by ATH if binding to the enzyme was reduced by surface modifications or competition by a polyanion. Addition of heparin in reactions of ATH+IIa were studied in the presence of fibrin. ATH+IIa reactions with equimolar amounts of added H and 4000 nM fibrin resulted in a 2-fold reduction in rate compared to experiments without added H or fibrin (FIG. 37). However, inclusion of a 40-fold molar excess of H in the ATH+IIa reaction mixture led to a 12-fold rate reduction when fibrin was present (FIG. 37). The fact that H competitively inhibited the ATH+IIa reaction to a greater degree when fibrin was present suggested that the H moiety in ATH might be involved in additional interactions to those occurring when fibrin was absent. In contrast, similar reactions of IIa+AT with 40-fold excess of H in 4000 nM fibrin decreased the rate by about 40% compared to experiments with equimolar added H (FIG. 37). Structural characteristics of ATH reaction with IIa were considered. Studies of ATLMWH showed a marked decrease in reaction velocity for inhibition of IIa compared to that for ATH+IIa (12-fold difference (FIG. 38)). Alternatively, the decrease in rate of ATLMWH inhibition of Xa compared to ATH+Xa was less pronounced than the corresponding reactions with IIa (6.7-fold less reduction in the inhibition rate of Xa than IIa). This is not surprising given that inhibition of IIa by AT●H requires binding of the enzyme to the GAG while inhibition of Xa does not (Jordon, R E, et al, 1980, J. Biol. Chem. 255:10081. The rate of IIa reaction with ATHLA was significantly decreased compared to that for ATH (FIG. 38). Thus, activation of the AT in ATH by the H pentasaccharide is important for IIa inhibition and simple covalent linkage of AT and H is insufficient for rapid reaction. ATH that contained a heparin fraction with low molecular weight and low affinity (ATLMWLAH) had vastly reduced rate of reaction with IIa, confirming the importance of both the bridging to IIa and activation of AT in the mechanism of IIa inhibition by ATH (FIG. 38).

Figure 40:
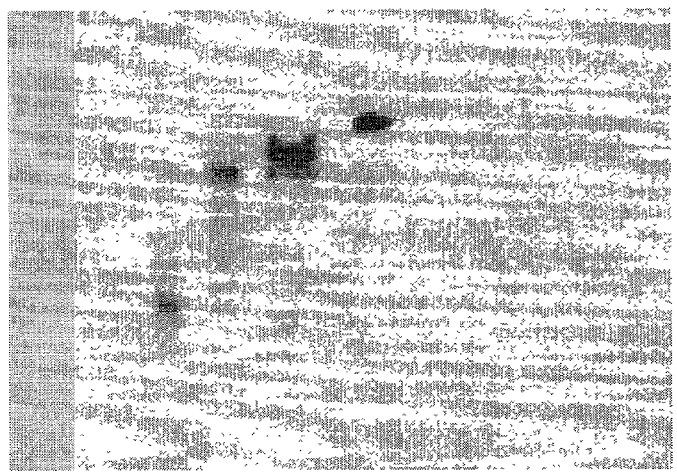
FIG. 40 shows binding of thrombin (IIa) to covalent antithrombin-heparin complex (ATH) in the presence of fibrin (Fn). Solutions of $^{125}$I-labeled thrombin (IIa)±covalent antithrombin-heparin complex (ATH)±soluble fibrin monomer (Fn) were prepared. Subsamples of the solutions were either mixed with 5% glycerol in buffer and electrophoresed on native gels under non-denaturing conditions (panel A) or heated for 1 min at 100° C. with 2-mercaptoethanol/SDS and electrophoresed on SDS gels under denaturing conditions (panel B). Autoradiograms of the dried gels are shown.
Figure 40:
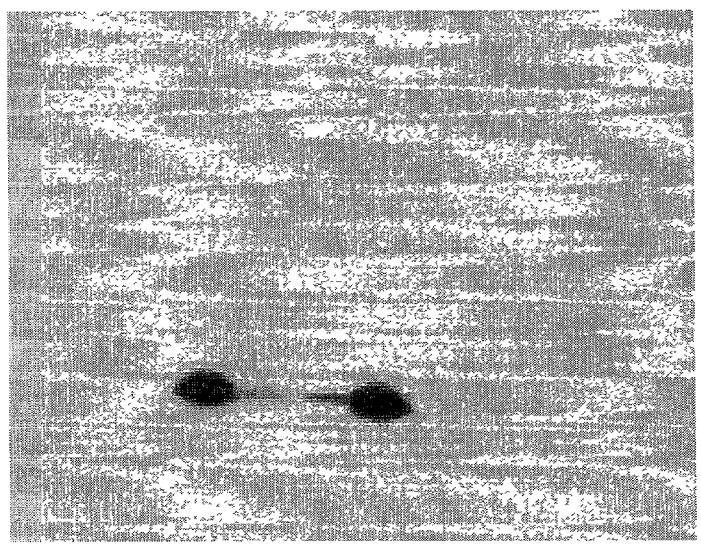
Figure 41:
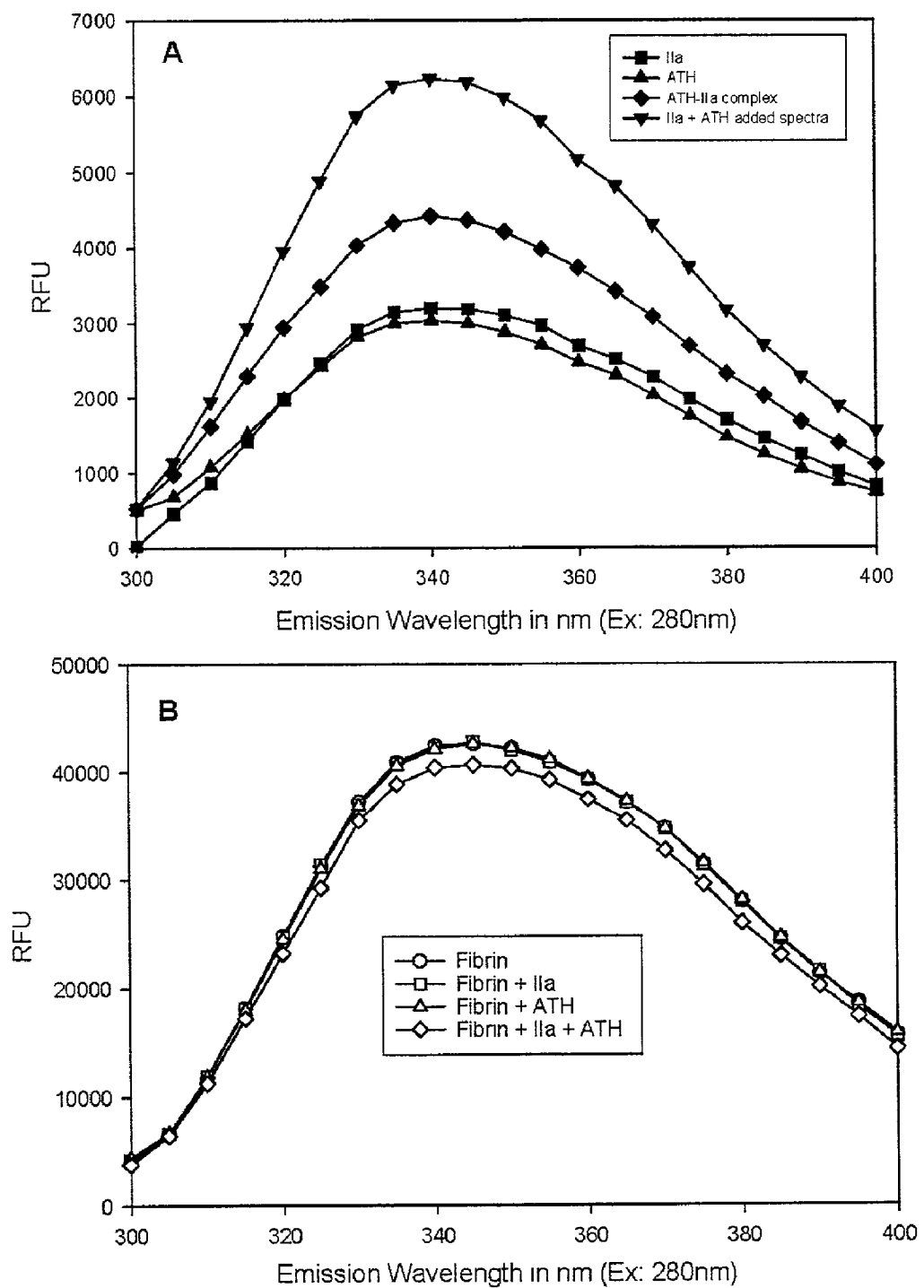
FIG. 41 shows spectral analysis of intrinsic fluorescence of the reaction of thrombin (IIa) with covalent antithrombin-heparin complex (ATH) in the absence or presence of fibrin (Fn). Solutions of 400 nM thrombin (IIa), 400 nM covalent antithrombin-heparin complex (ATH) and 400 nM ATH-IIa complex (IIa reacted with equimolar ATH) were prepared and spectral scans carried out (panel A). The mathematical sum of spectra for IIa and ATH (added spectra) is shown for comparison. Similar solutions of 1000 nM soluble fibrin monomer±400 nM IIa±400 nM ATH were prepared and scanned (panel B). Fluorescence spectral scans were performed from 300 nm to 400 nm with excitation at 280 nm (290 nm filter). Relative fluorescence units (RFU) from the spectrometer are plotted versus emission wavelength.
Figure 42:
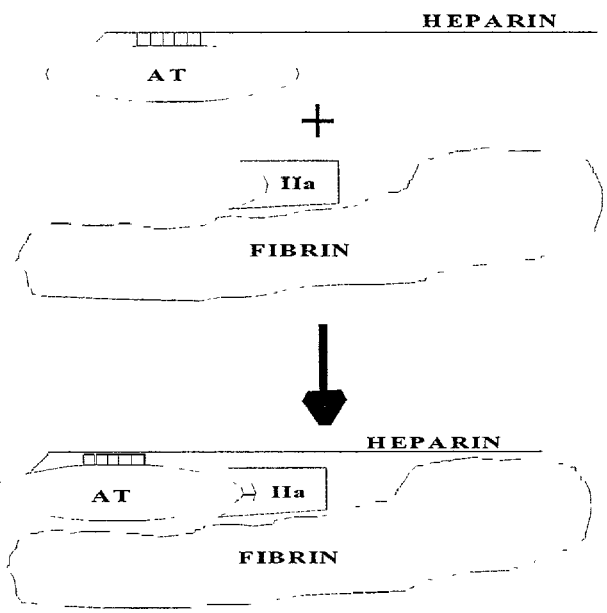
FIG. 42 shows a model of the inhibition of fibrin-bound thrombin (IIa) by covalent antithrombin-heparin complex (ATH). Panel A shows a reaction mechanism for inhibition of thrombin (IIa) on fibrin by covalent antithrombin-heparin complex (ATH). For comparison, panel B shows the formation of ternary fibrin●IIa●heparin complex+free antithrombin (AT) when non-covalent AT●heparin approaches fibrin-bound IIa.
Figure 42:
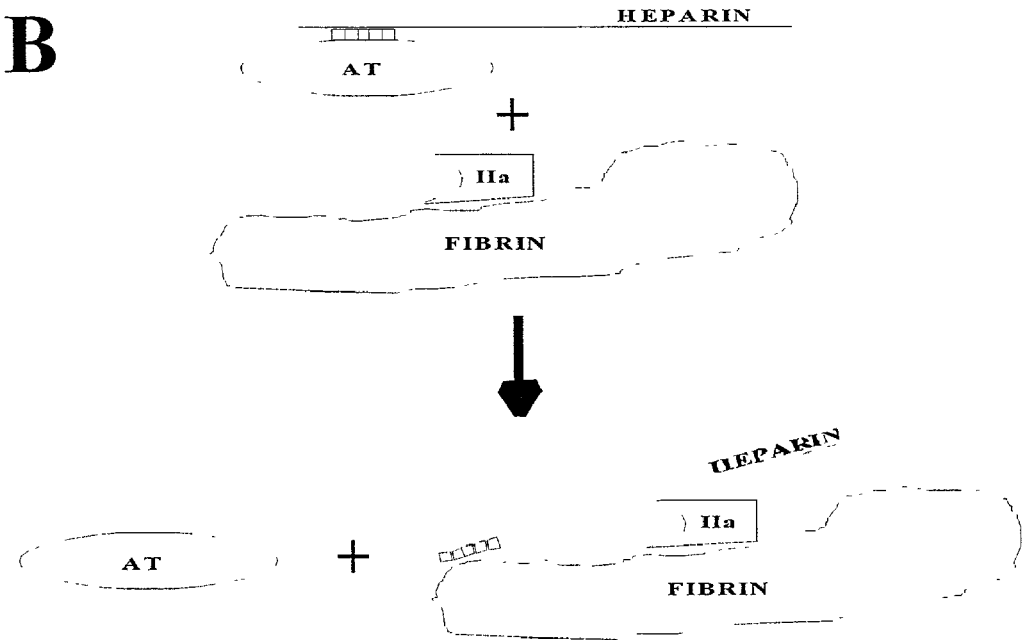

In order to further characterize the mechanisms involved in ATH interaction with IIa+fibrin, direct binding studies were performed. Initial experiments showed that, unlike the AT in AT●H, ATH bound strongly to fibrin monomer in buffer (FIG. 39). Previous reports have shown that since the H in AT●H has sufficient affinity for fibrin, AT in the complex can dissociate, allowing for fibrin●H formation (Hogg, P J, et al, 1996, J. Biol. Chem. 271:26088; Raut, S, and Gaffney, P J, 1996, Throm. Res. 81:503–509). Conversely, since AT is covalently linked to H in ATH, binding of the H moiety in the conjugate to fibrin would necessitate AT-fibrin localization. Further experiments with $^{125}$I-IIa verified that ATH reacted rapidly to form IIa-ATH inhibitor complexes with fibrin-bound IIa. In addition, once formed, IIa-ATH remained bound to the fibrin (FIG. 40). Retention of IIa-ATH by fibrin after IIa+ATH reaction was likely through the GAG chain of ATH, since addition of large quantities of exogenous H inhibited the ATH reaction with IIa●fibrin (FIG. 37). Binding of the ATH to fibrin may assist in localizing the inhibitor with fibrin-bound RA-IIa, partially compensating for the lack of H-binding affinity of the IIa mutant. Fluorescence measurements further confirmed that significant conformation/environmental changes occurred during reaction of ATH and IIa on fibrin, that were not observed with fibrin bound to either ATH or IIa alone (FIG. 41). A model for the ATH inhibition of IIa bound to fibrin can be constructed which incorporates all of the observations to date. ATH reacts with fibrin-bound IIa to form a covalent ATH-IIa inhibitor complex that remains bound to the fibrin (FIG. 42A). However, non-covalent AT●H interacts with fibrin-bound IIa to form a ternary fibrin●IIa●H complex and dissociated free AT (FIG. 42B).

In summary, covalent ATH can inhibit fibrin-bound thrombin at a rate much faster than that for non-covalent AT●H complexes. Although binding to fluid phase IIa by the GAG chain on ATH appears to be important, the activated AT moiety in the conjugate reacts with a IIa mutant, that has reduced H-affinity, to a similar degree whether fibrin is present or not. Thus, it seems likely that ATH can access the H-binding site on IIa that is fibrin bound and react rapidly due to the permanently activated covalently-linked AT. The importance of AT activation by the pentasaccharide on ATH's GAG component was verified by the reduced activity of AT complexed to low affinity H. Direct binding experiments showed that ATH interacts with fibrin and the final ATH-IIa inhibitor complex formed remains fibrin-bound (likely through the H moiety since exogenous H inhibited formation of fibrin●ATH-IIa).

Example XII

The following experiments were performed.

2,566 IU (368.5 mg) of human antithrombin (AT)(Thrombate III® Bayer) was mixed with 3,000,000 IU (16.4 gm) of porcine heparin (Sigma) in 260 ml PBS buffer and incubated in a 40° C. constant temperature water bath for 13 days. The NaCNBH$_3$ was added to reduce any remaining un-rearranged Schiff Bases. A final ATH yield of 46.5% was achieved.

At the end of the first day, a 0.5 ml aliquot of the reaction mixture was transferred to an eppendorf microtube for continued parallel incubation and sampling at various time points. For electrophoresis, 10 µl (14 µg AT) was removed at each time point and transferred to another eppendorf tube that was stored at −80° C. The following time points were collected:

| | | |
|---|---|---|
| $t_1$ | 21 hr. | "1 day" |
| $t_2$ | 44.5 hr. | "2 day" |
| $t_3$ | 68.5 hr. | "3 day" |
| $t_6$ | 140 hr. | "6 day" |
| $t_7$ | 165.0 hr. | "7 day" |
| $t_8$ | — | "8 day" |
| $t_9$ | — | "9 day" |
| $t_{10}$ | — | "10 day" |

35 µl sample buffer containing SDS and mercaptoethanol was added to each time point tube, and the tube boiled for 5 minutes. 15 µl of each of the resulting time point samples was then loaded on a 7.5% SDS PAGE gel and electrophoresed at 100V for 20 minutes. The gel was then fixed overnight in 40% methanol+10% acetic acid, stained for 10 minutes with 0.5% coomassie blue, destained with 10% acetic acid, and dried between two sheets of a Bioscience semi-permeable membrane for gels on a BioRad gel drier under vacuum at 80° C. for 2 hours.

The gel was scanned and bands quantitated on a Pharmacia ImageMaster VDS gel documentation system. Baseline gel density values appeared to be about 0.024, typically varying by about 0.015.

Results:

There was a five day lag period before stable covalent ATH made at 40° C. was detected. Yield drops drastically to about 6% in 14 days when the reaction incubation temperature is reduced to 37° C. Significantly lower yield is expected at room temperature (25° C.) and lower temperatures.

Example XIII

Mechanisms Responsible for Catalysis of the Inhibition of Factor Xa or Thrombin by Antithrombin Using a Covalent Antithrombin-Heparin Complex Chemicals—All reagents were of analytical grade. Standard heparin (H) was from Sigma (grade I-A, Na salt, 15 kD average molecular mass, from porcine intestinal mucosa (Mississauga, ON, Canada)). Human antithrombin (AT) was from Bayer (Mississauga, ON, Canada). Stachrom Heparin kits (containing the CBS 31.39 substrate for factor Xa) were obtained from Diagnostica Stago (Asnières, France) and anti-IIa kits were from American Diagnostica Inc. (Greenwich, Conn., USA). Protamine Sulfate was obtained as the solid from ICN (Cleveland, Ohio, USA) while Arginine was purchased from Sigma. Sephadex G-200 beads, CNBr-activated Sepharose 4B and Heparin-Sepharose CL6B were all from Amersham Pharmacia Biotech (Uppsala, Sweden). Molecular weight standards used to characterize Sephadex G-200 chromatograms were: Dextran 70000 (Pharmacia, catalogue # T-70), Dextran 42000 (Sigma, catalogue # D-4133), Dextran 10 (Pharmacia, catalogue # Dextran 10, Lot No. To 5400), and Dextran Sulfate 8000 (Sigma, Na salt, catalogue # D-4911). Bio-gel P-6 was from Bio-Rad (Mississauga, ON, Canada). Molecular weight standards used to characterize Bio-gel P-6 chromatograms were: disodium 2-acetamido-2-deoxy-4-O-(4-deoxy-α-L-threo-hex-4-enopyranosyluronic acid)-6-O-sulfo-D-glucose (Seikagaku America Inc, Ijamsville, Md., USA, Catalogue # 400575, MW=455.4), tetrasodium 2-deoxy-2-sulfamino-(4-deoxy-2-O-sulfo-α-L-threo-hex-4-enopyranosyluronic acid)-6-O-sulfo-D-glucose (Seikagaku America Inc, catalogue #400575, MW=665.5), heparin tetrasaccharide (produced by exhaustive treatment of heparin with NaNO$_2$+dilute acetic acid, isolated on Sephadex G-25 (Pharmacia) and the molecular weight (1192 g/mole) determined by end group analysis (Hurst, R E and Settine, J M, 1981 Anal. Biochem 115, 88–92) of weighed samples) and low molecular weight heparin fragment (Na salt, Sigma, catalogue # H-3400, MW=3000 (verified by HPLC)). Human factor Xa and human thrombin were obtained from Enzyme Research Laboratories (South Bend, Ind., USA) while the S-2238 chromagenic substrate for thrombin titrations was from DiaPharma (West Chester, Ohio, USA). ATH was prepared as described previously (Chan, A. K., et al. (1997) supra; Chan, A. K., et al,(1998) Blood Coag Fibrinol 9, 587–595). Briefly, AT was incubated with H at 40° C. in 0.15 M NaCl 0.02 M phosphate buffer pH 7.3 for 14 days, followed by purification of the covalent product by sequential chromatographies on butyl-agarose (Sigma) and DEAE Sepharose Fast Flow (Amersham Pharmacia Biotech). SDS PAGE (reducing conditions) of the ATH produced showed that <5% of free unreacted AT or H were present in the final preparation. In order to ascertain the AT and H present in the conjugate, detailed chemical analyses were carried out (see below). Heparin chains from ATH were prepared according to a procedure similar to that described previously (Berry, L., et al (1998) supra). In brief, ATH (equivalent to 8.66 mg AT)+2 mg protease P-5147 (Sigma) in 1 mL of 0.5 M Tris-HCl pH 8.0 were heated at 37° C. for 24 h. The incubate was centrifuged in a microfuge and the supernatant dialyzed against 0.01 M Tris-HCl pH 8.0. Dialyzed product was loaded onto DEAE Sepharose Fast Flow (3 mL packed beads) that was pre-equilibrated with 0.01 M Tris-HCl pH 8.0. After washing the column with 0.25 M NaCl in 0.01 M Tris-HCl pH 8.0, heparin chains were eluted with 2 M NaCl in 0.01 M Tris-HCl pH 8.0. The eluted heparin (~2 mg) was dialyzed versus 0.1 M NaCl and stored at 4° C. Heparin isolated from protease-treated ATH was designated as H'.

Physicochemical Analyses of ATH—The AT and heparin content in ATH was measured using several methods in order to rigorously determine the AT:heparin mole ratio as a confirmation of earlier studies. ATH was hydrolyzed in 6 M HCl at 100° C. for 20 h and, after evacuation under vacuum, analyzed for amino acid content (Beckman System 6300 High Performance Analyzer) against an amino acid reference that had been added as an internal standard. Given the known protein sequence and N-linked glycan content for human antithrombin (Manson, H. E., et al (1989) Transf Med Rev 3, 264–281; Miller-Andersson, J., et al (1974) Thromb Res 5, 439–452) the molecular weight of AT was calculated to be 57769. Analysis of results for amino acids which are stable to acid hydrolysis (ie.: Alanine, Arginine) was used to determine the number of moles of AT in the original sample (31 Alanine residues and 22 Arginine residues per AT molecule) and, thus, the number of mg of AT per unit volume of original ATH solution. Measurement of the absorbance at 280 nm of ATH stock solution and use of the mg AT/mL determined by amino acid analysis allowed for calculation of an extinction coefficient for ATH in terms of AT concentration. Three different methods were used to evaluate the heparin content in ATH. Heparin mass concentration in stock ATH solution was analyzed using the carbazole (Bitter, T., and Muir, H. M. (1962) Anal Biochem 4, 330–3340), azure A (Grant, A., Linhardt, R. J., Fitzgerald, G. L., Park, J. J., and Langer, R. (1984) Anal Biochem 137, 25–32) and alcian blue (Gold, E. W. (1979) Anal Biochem 99, 183–188) techniques. In each case, background measured in samples containing a similar concentration of purified AT was subtracted from values calculated for ATH. Standards were prepared from solid commercial Sigma heparin (H). The number average molecular weight (Mn) of heparin released from ATH by exhaustive protease treatment was measured by gel filtration on a Sephadex G-200 column (Amersham Pharmacia Biotech) that was pre-calibrated using dextran (sulfate) standards (Sigma) of known molecular weight. Calculation of Mn was according to the formula $Mn=\Sigma(C_f)/\Sigma(C_f M_f)$ where: Mn=number-average molecular weight, $C_f$=relative weight/volume concentration of heparin in the fraction, and $M_f$=the molecular weight of material within the fraction (according to the standard curve). Finally, the number of moles of AT and heparin in ATH stock solutions were used to calculate the heparin:AT mole ratio in ATH.

Anti-Factor Xa and Anti-Factor IIa Assays—Anti-Factor Xa activities were determined using the commercially available Stachrom Heparin Kit. H standards (0, 0.4 and 0.8 anti-factor Xa IU/mL), controls or samples (50 µL), diluted in the presence (for catalytic activity) or the absence (for checking non-catalytic activity) of AT, were incubated with purified bovine factor Xa for 120 seconds at 37° C. After the incubation period, the chromogenic substrate CBS 31.39 is added, mixed and incubated for 90 seconds before reading the absorbance at 405 nm. Control and unknown sample values were determined by interpolation from the linear heparin standard curve. The anti-factor IIa assay was determined chromogenically by commercially available kits called Actichrom Heparin anti-IIa. Heparin standards (0.0–0.6 USP units/mL), controls (1:16 dilution), or samples (1:16 dilution) were added to AT-containing reagent, followed by mixing and incubation at 37° C. for 2 minutes. Thrombin reagent was then added, followed by mixing and incubation for a further 2 minutes at 37° C. Finally, Spectrozyme TH substrate was added and the mixture incubated for 1 minute before reading the absorbance at 405 nm. Similar to the anti-Xa assay, control and unknown sample absorbance values were interpolated from the heparin standard curve. All assays were performed on an automated ACL 300+machine (Instrumentation Laboratories, Milano, Italy). The heparin values were converted from U/mL to U/mg by dividing the heparin activity values by the heparin mass concentrations (mg/mL), as determined by protamine sulfate assay (see below).

Protamine Sulfate Assay—The protamine sulfate assay is an aggregation assay used to determine the heparin mass concentration in a sample (Hatton, M. W. C., et al (1979) Can J Biochem 57, 1183–1190; Hatton, M. W. C., et al (1978) Thromb Res 13, 655–670). Briefly, 0.2 mL of 1.0 mg/mL protamine sulfate solution in H₂O was added to 0.5 mL of H standards, ATH standards or unknown samples, following by immediate vortexing. After 10 minutes at room temperature, 1.0 mL of 0.1 M L-arginine was added to the mixture and vortexed, followed immediately by the addition of 2.3 mL of 0.1 M Tris-HCl pH 8.0 and further vortexing. Absorbances of H standards, ATH standards or unknown samples were read at 470 nm within 1 hour and unknown samples were read from the appropriate H or ATH standard curve.

Sepharose-AT Chromatography—Lyophilized AT powder was reconstituted with 10 mL of sterile H₂O from the kit. It was then dialyzed against coupling buffer before conjugation to CNBr-activated Sepharose beads. Conjugation of AT to the beads was done according to the manufacturer's instructions and resulted in affinity matrix material containing 9.84 mg of AT/mL. Sepharose-AT columns (10 mL, pre-equilibrated with 0.15 M NaCl in 0.01 M phosphate pH 7.3 buffer) were loaded with either ATH (equivalent to 2 mg AT and 0.6 mg H), H, AT+H, H', HMWATHF, LMWATHF, HMWH or LMWH at similar loading levels (33.9 nmoles of each species). After loading, the column was washed with 3 column volumes of 0.15 M NaCl buffer before elution of any bound material with a linear gradient (25 mL of 0.15 M NaCl buffer in the mixing chamber and 25 mL of 2 M NaCl buffer as limit solution). Finally the column was treated with two column volumes of 2 M NaCl buffer to ensure equilibration of the column with high salt. NaCl concentrations in the eluate were determined using a conductivity meter (E C. Meter, Amber Science Inc., Eugene, Oreg., USA). Fractions were analyzed for either protein or heparin by measuring absorbance (280 nm or 215 nm) or taking samples for assay with protamine (as described above), respectively. AT or heparin peaks were dialyzed against $H_2O$, freeze-dried and resuspended in 0.15 M NaCl for further assays for activity (anti-factor Xa or anti-IIa, described above). Smaller columns of Sepharose-AT (1.5 mL) were constructed for chromatographies of factor Xa-ATH or thrombin-ATH complexes using the same washing and elution protocols as those for the larger columns.

Fractionation of ATH or H into High and Low Molecular Weight Fractions—Fractionation of ATH by molecular weight was performed on a Sephadex G-200 column. The Sephadex G-200 column was prepared swollen and poured according to the manufacturer's instructions. The column (300 mL) was equilibrated with 2 M NaCl and 20 mg of ATH was loaded, elution being with 2 M NaCl. Fractions were collected ($\approx$3.9 mL/fraction) and analyzed for protein concentration ($A_{280}$). The column fractions of high (the first to be eluted from the column) and low molecular weight species were designated high molecular weight ATH fraction HMWATHF and low molecular weight ATH fraction LMWATHF, respectively. The first 2–9% (HMWATHF) and the last 2–9% (LMWATHF) of the eluted fractions were separately pooled, and then dialyzed against 0.15 M NaCl in 0.01 M phosphate pH 7.3 buffer before further fractionation on Sepharose-AT. To confirm the molecular weight of LMWATHF, the chain length of heparin released from LMWATHF by long incubations at 37° C. with catalytic amounts of protease (<10% by mass) was assessed by gel filtration on a Bio-gel P-6 column. Elution of the LMWATHF heparin chains from the Bio-gel P-6 column (calibrated using heparin oligosaccharide standards from Seikagaku America Inc. (Rockville Md., USA) and Sigma (Mississauga, ON, Canada), as well as H tetrasaccharide (Na salt) prepared and characterized as described in the chemicals section) was with 0.15 M NaCl (1 mL fractions), detection being with a refractive index detector (Jasco RI-1531, Tokyo, Japan). The HMWATHF (equivalent to 1.4 mg of AT) and LMWATHF (equivalent to 1.6 mg AT) samples were subjected to Sepharose-AT chromatography (10 mL column) that was pre-equilibrated with 0.15 M NaCl buffer at pH 7.3. After loading, the column was washed with 2 column volumes of 0.15 M NaCl buffer before elution of any bound material, using a linear NaCl gradient and a 2 column volume 2 M NaCl wash as described above. Fractions were analyzed for protein by measuring absorbances at 280 nm and 215 nm. Sepharose-AT chromatographic peaks were pooled then dialyzed against $H_2O$, freeze-dried and resuspended in 0.15 M NaCl for further assays for activity (anti-factor Xa or anti-IIa, described above). HMWH and LMWH were prepared in the same way as described for HMWATHF and LMWATHF, except that 5 mg of H was gel filtered and heparin analyses were by the protamine sulfate assay.

Sepharose-AT Chromatography of Serine Protease-ATH Inhibitor Complexes—Factor Xa-ATH or thrombin-ATH inhibitor complexes were prepared as follows. Each serine protease was used to titrate ATH to $\approx$100% equivalence, as determined by the presence of a small amount of activity against its chromogenic substrate (CBS 31.39 substrate from the Stachrom Heparin kit for factor Xa, S2238 substrate for thrombin). Factor Xa or thrombin was added to 0.25 mg of ATH (in terms of AT) and, after adjusting the total volume to 1 mL, immediately loaded onto a 1.5 mL Sepharose-AT column. Identical washing and elution protocols were used as those for the larger (10 mL) columns. The various eluted peaks, as well as preformed factor Xa-ATH and thrombin-ATH complexes, were assayed for anti factor-Xa activity as described above. In order to investigate the possibility that excess free AT may actually protect the AT of ATH from attack by protease, competition experiments were carried out. Either factor Xa or thrombin was reacted for various time periods with ATH±100 fold molar excess of added AT at 37° C. Reaction was stopped by heating at 100° C. for 5 min and the ATH containing material purified from free thrombin, factor Xa or AT by chromatography on DEAE Sepharose using the same method as that for ATH purification given above (Chan, A. K., et al (1997) J Biol Chem 272, 22111–22117). ATH+enzyme-ATH inhibitor complexes were treated with heparinase for 2 h at 37° C., followed by SDS PAGE and staining of the gels with Coomassie Blue R 250 for protein as described previously (Chan, A. K., et al (1997) J Biol Chem 272, 22111–22117). Laser densitometry of bands on dried gels was carried out to determine the proportion of free ATH (as AT) compared to enzyme complexed ATH (as either factor Xa-AT or thrombin-AT). Comparison of results from lanes of experiments that had no added AT to those with added AT revealed the effect of added AT on direct reaction of ATH with either factor Xa or thrombin.

Determination of Binding Affinities Using Intrinsic Fluorescence—All fluorometric determinations were made with stirring in a 1×1 cm quartz fluorescence cuvette placed in a cuvette holder heated at 25° C. and using a Perkin Elmer LS50B luminescence spectrometer. Experiments were carried out by adding either 1 mL of 100 nM AT, 100 nM AT+234 nM H, 100 nM ATH or 100 nM LMWATHF in 0.02 M Tris-HCl pH 7.4 to the cuvette, followed by titration with 5 M NaCl 0.02 M Tris-HCl pH 7.4 containing either 100 nM AT, 100 nM AT+234 nM H, 100 nM ATH or 100 nM LMWATHF, respectively. Thus, the NaCl concentration of AT, AT+H, ATH or LMWATHF was increased from 0 M to 2.25 M. Protein intrinsic fluorescence was measured (after each high salt solution addition (added in 10–100 µL increments)) with an excitation at 280 nm and emission detected at 340 nm (with a 290 nm cut-off filter). Excitation and emission slit widths were 5 nm and 7 nm, respectively. The effect of NaCl on intrinsic fluorescence was determined as the fluorescence intensity after each high salt addition minus the value at equilibrium end point (2.25 M NaCl) and calculated as a percentage of the difference in fluorescence intensity at 0 M and 2.25 M NaCl. Values for the percent difference in fluorescence for AT+H, ATH and LMWATHF were corrected for change in fluorescence of AT alone at similar NaCl concentrations.

Sepharose-Heparin Chromatography—The heparin Sepharose CL-6B column was prepared according to the manufacturer's instructions. The column (10 mL) was equilibrated with binding buffer (0.15 M NaCl in 0.01 M phosphate pH 7.3 buffer). ATH (equivalent to 2 mg of AT), AT (2 mg or 4 mg of protein), AT (2 mg)+H (0.5 mg), or AT (2 mg)+H' (0.6 mg) were loaded onto the column, followed by washing with 3 column volumes of binding buffer before elution of bound material with a linear NaCl gradient (0.15 M–2.0 M) and final washing with 2 column volumes of 2.0 M NaCl. Absorbance at 280 nm and 215 nm of the collected fractions was used to determine protein concentration and protamine sulfate assay was used to measure H concentration. Fractions in the different peaks were pooled, dialyzed against H$_2$O, freeze-dried and resuspended in 0.15 M NaCl for activity testing (anti-factor Xa or anti-IIa).

Statistical Analysis—Data were compared for significant differences using either the students t-test (in the case of two groups) or by analysis of variance (ANOVA, for more than two groups). Upon finding a significant difference within several groups by ANOVA, testing between two groups within that set was carried out by t-test. A p value of <0.05 was considered significant and results were expressed as mean±SE.

RESULTS

Physicochemical Analysis of, ATH—Stringent analyses of the protein and heparin content of ATH preparations were carried out to verify the heparin:AT mole ratio present in the conjugate. Aliquots of ATH stock solution were treated with HCl and the hydrolyzate analyzed to determine amino acid content. Given the known sequence for human AT, the number of moles of acid stable amino acids (Alanine, Arginine) recovered were used to calculate the molar concentration (in terms of AT) of the original ATH solution. Typical ATH stock solutions were $1.4 \times 10^{-4}$ M in AT. Given a molecular weight for AT of 57769 (calculated from the amino acid sequence and known carbohydrate content (Manson, H. E. et al (1989) Transf Med Rev 3, 264–281; Miller-Anderson, J. et al (1974) Thromb Res 5, 439–452), absorbance readings at 280 nm for dilutions of ATH stock solutions gave an extinction coefficient of 0.641 for ATH concentrations of 1 mg AT/mL. A value of 0.630 obtained for purified human AT was in agreement with that found previously (Nordenman, B., et al (1977) Eur J Biochem 78, 195–203). Three separate methods were used to determine the mass concentration of heparin in ATH solution. Background contribution due to AT in the ATH sample was assessed using AT solutions of similar concentration. Although AT control values were low in azure A and alcian blue heparin assays, a significant value was obtained when the carbazole assay was applied (Table 16). The relatively high signal given by AT controls in the carbazole assay was not surprising given that neutral sugars in the N-linked glycans of AT give H$_2$SO$_4$ dehydration products that condense with carbazole in the assay procedure (Bitter, T., and Muir, H. M. (1962) Anal Biochem 4, 330–334; Dubois, M. et al (1956) Anal Chem 28, 350–356). Nevertheless, after correction for AT control values, heparin:AT mass concentration ratios were similar for all 3 assay methods (although precision was reduced for the carbazole procedure). Heparin:AT mole ratios for ATH were calculated from the heparin mass assays, given the number of moles of AT in the stock solution (as determined above) and an average molecular weight for heparin chains in ATH of 15400 (see below). Results from the 3 heparin mass analysis procedures indicated that the heparin:AT mole ratio for ATH was close to 1:1 (Table 16). Heparin mass concentration analyses of HMWATHF and LMWATHF using the Azure A method gave results that were proportional to the relative molecular weights of the conjugate heparin chains.

Figure 43:
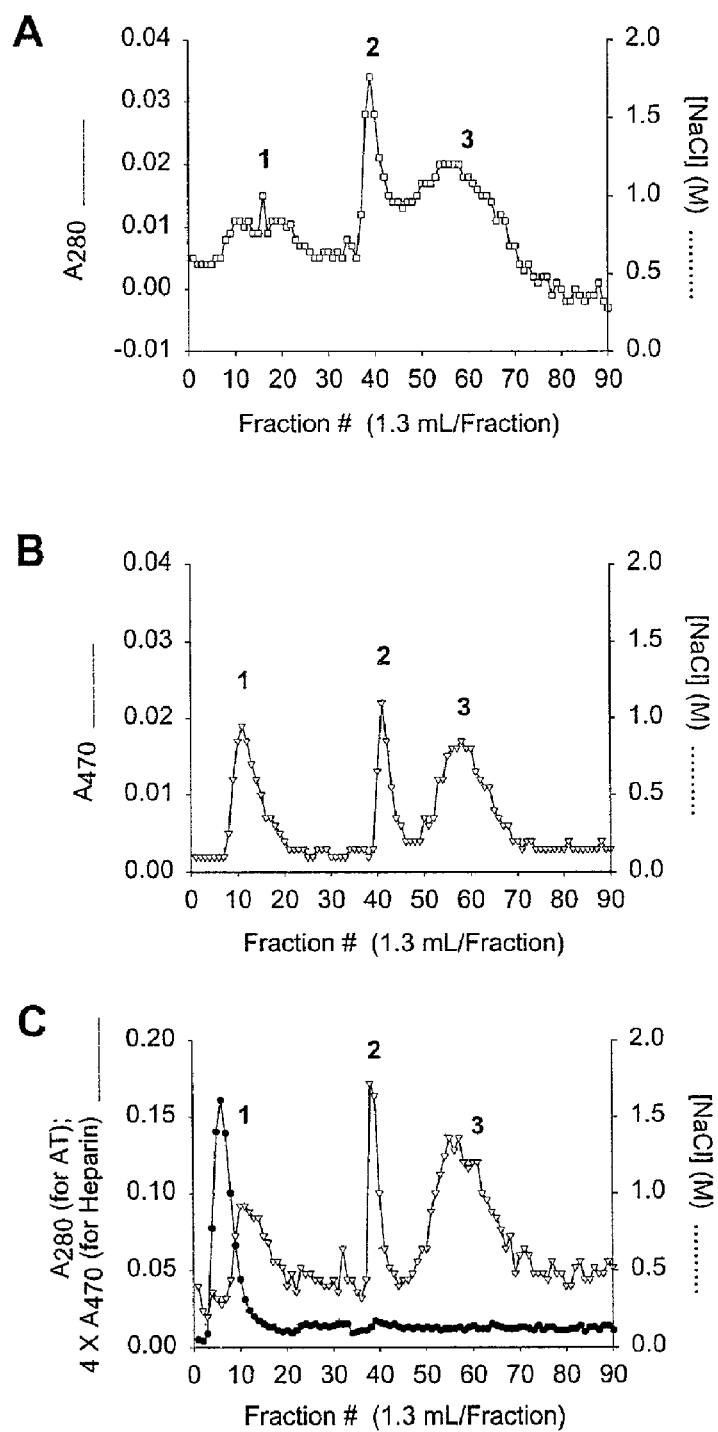
FIG. 43 Chromatography of covalent antithrombin-heparin complex (ATH), unfractionated heparin (H) and non-covalent complexes of antithrombin (AT)+H on Sepharose-AT. (A) ATH (2 mg in terms of AT), (B) H (0.5 mg) or (C) AT (2 mg)+H (0.5 mg) were chromatographed on 1 cm (I.D.)×12 cm (long) columns of Sepharose-AT (pre-equilibrated with 0.15 M NaCl in 0.01 M phosphate pH 7.3 buffer) with 1.3 mL fractions of effluent being collected. After loading, the column was washed for 30 fractions with 0.15 M NaCl in 0.01 M phosphate pH 7.3 buffer. Elution of bound material was with a linear gradient (25 mL of buffered 0.15 M NaCl in the mixing chamber and 25 mL of buffered 2 M NaCl as limit solution) followed by 2 column volumes of 2 M NaCl in buffer. Eluted material was detected by $A_{280}$ (protein) or protamine sulfate assay (heparin ($A_{470}$)) and appeared as either unbound, low affinity or high affinity peaks (numbered 1, 2 or 3, respectively). In the case of AT+H chromatographies, unbound (peak 1) AT (●) and H (∇) materials chromatographed separately.
Figure 44:
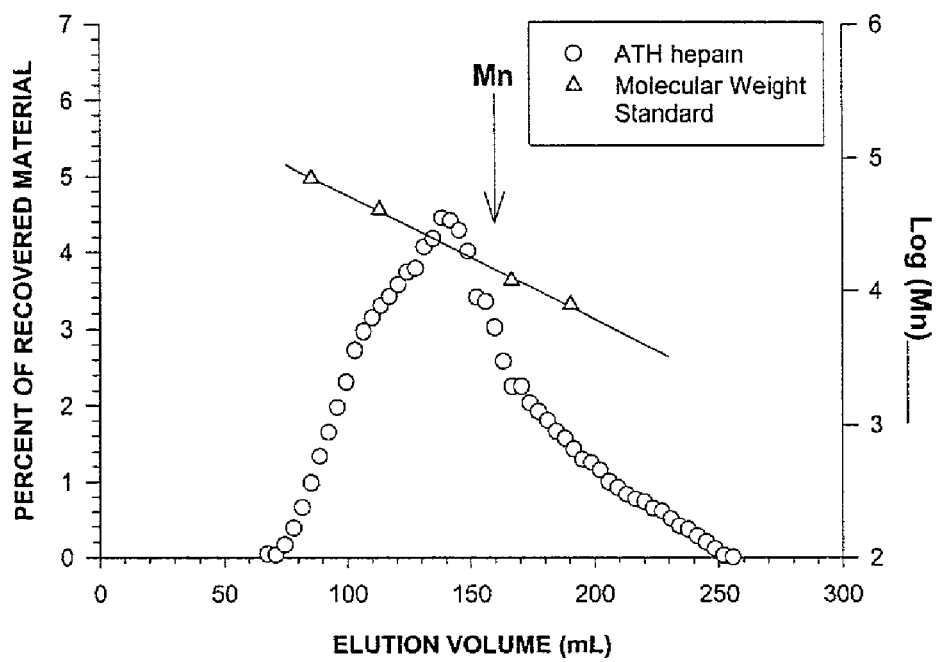
FIG. 44 Analysis of chain length and Sepharose-AT binding affinity of heparin chains from covalent antithrombin-heparin complex (ATH). Heparin chains released from ATH using protease (H') were gel-filtered on Sephadex G-200 (2.6 cm I.D.×49 cm long) using 2 M NaCl as irrigant (A). A number-average molecular weight (Mn) standard curve is shown and the elution position of the calculated Mn value for H' indicated with an arrow. H' was chromatographed on Sepharose-AT (column and conditions the same as in FIG. 43) to give unbound, low and high affinity peaks 1, 2 and 3, respectively (B).
Figure 44:
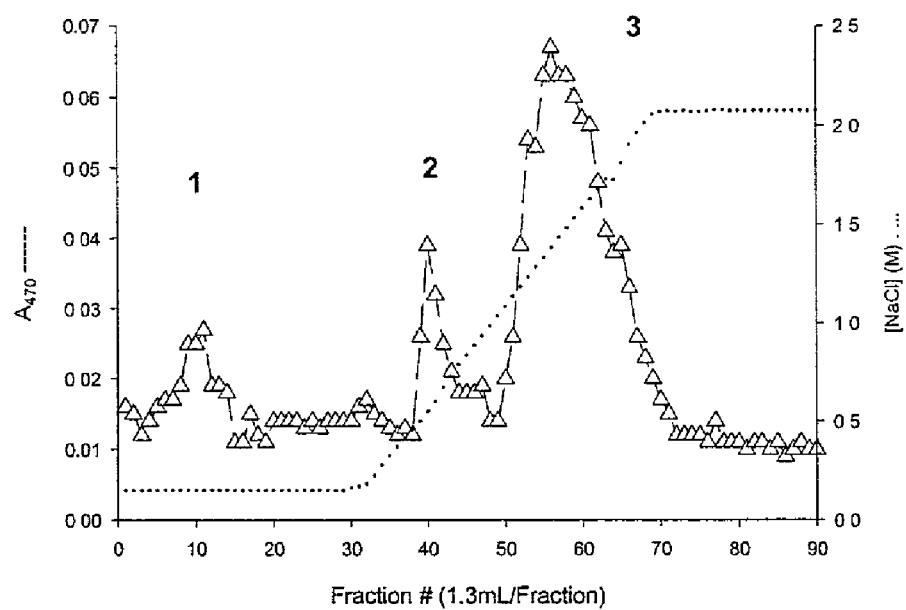

Sepharose-AT Fractionation of ATH and H—Chromatography of ATH on immobilized AT resulted in binding of >80% of the load (>70% as a high affinity fraction, FIG. 43A). In order to ensure that the Sepharose-AT column was not overloaded, chromatographies with different loading amounts were run. Similar chromatographies of H gave sizable peaks of unbound (~40% of the total recovery (FIG. 43B). Sepharose-AT chromatographies of either ATH or H resulted in 3 distinct peaks: peak 1 appearing in the wash fraction as unbound material, as well as peaks 2 and 3 which represented low and high affinity products, respectively, that were eluted from the column by linear NaCl gradient (0.15 M to 2 M). This 3 peak pattern (no affinity (unbound peak 1), low affinity (peak 2) and high affinity (peak 3)) was typical of separations of heparin containing species on immobilized AT. Chromatography of non-covalent AT●H complexes on the AT column lead to dissociation of protein and GAG, with free AT running slightly ahead of unbound H, followed by the usual low (peak 2) and high (peak 3) affinity gradient eluted peaks (FIG. 43C). The relative proportions and elution positions of peaks produced by Sepharose-AT fractionation of AT+H was essentially the same as those of H alone (compare FIGS. 43B and 43C) and in agreement with the 45% –55% high affinity AT-binding observed previously for this commercial H (Berry, L. et al (1998) J Biol Chem 273, 34730–34736). Fractions in the peaks obtained from Sepharose-AT chromatographies were pooled and concentrated. Initial testing of the Sepharose-AT peaks showed that all ATH peaks had significant, direct non-catalytic activity against factor Xa, whereas peaks containing only H were completely inactive. Further assays were done to determine the ability to catalyze inhibition of factor Xa by added AT (catalytic anti-factor Xa assay). All assays for catalytic activity showed high sensitivity and reproducibility. As expected, while unbound and low affinity material from either H or AT+H chromatographies had very low catalytic anti-factor Xa activities (<10 U/mg heparin (Table 17)), H with high affinity for AT had significant catalytic activity (463 or 447 U/mg for H or AT●H, respectively (Table 18)). Alternatively, assays of unbound and low affinity material from Sepharose-AT chromatograms of ATH had moderate anti-factor Xa catalytic activities (231 and 112 U/mg heparin for peaks 1 and 2, respectively (Table 19)), and high affinity ATH contained 1.53 times the activity of high affinity H (t-test, p<0.01). Thus, the vast majority of ATH with potent activity to catalyze the factor Xa+AT reaction was capable of strong AT-binding, prior to complexation with a serine protease (ie. factor Xa or thrombin). In order to verify that the heparin chains of ATH were responsible for the significant binding affinity to immobilized AT, ATH was treated with protease and the heparin released (H') purified on DEAE Sepharose. The anti-factor Xa activity of H' was measured to be 644 U/mg. Gel filtration of H' showed that the ATH heparin chains had a number-average molecular weight (Mn) of 15400 (FIG. 44A). Thus, H' had a much higher proportion of molecules with longer chain length than standard H (Mn calculated from similar chromatographies of H was 11500). Chromatography of H' on Sepharose-AT resulted in 83% of the material having high affinity binding and potent (660 U/mg) anti-factor Xa activity (FIG. 44B and Table 17). Therefore, the vast majority of heparin chains in ATH contained catalytically active, high affinity AT-binding sites.

Figure 45:
FIG. 45 Analysis of fractions from size exclusion chromatography of covalent antithrombin-heparin complex (ATH). ATH was chromatographed on a Sephadex G-200 column (2.6 cm (I.D.)×43 cm (long)), followed by SDS polyacrylamide gel electrophoresis of alternating fractions (3.9 mL). The gel was stained for heparin using alcian blue, followed by silver for increased sensitivity. Alternating fraction number of the ATH peak increases (and molecular mass decreases) for lane numbers going from left to right and molecular weight on the gel decreases going from top to bottom.
Figure 46:
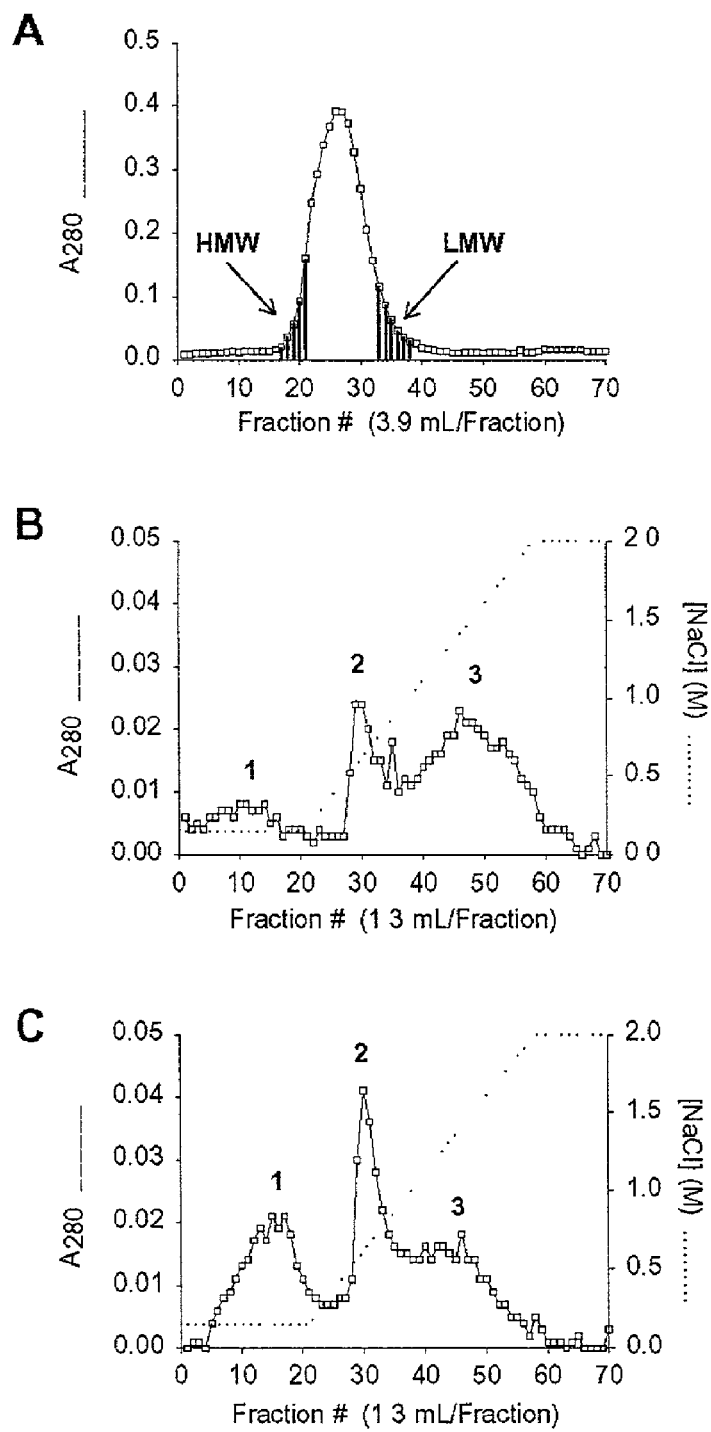
FIG. 46 Preparation of high molecular weight covalent antithrombin-heparin fraction (HMWATHF) and low molecular weight covalent antithrombin-heparin fraction (LMWATHF), followed by chromatography on Sepharose-antithrombin (AT). Covalent antithrombin-heparin (ATH, 20 mg in terms of AT) was gel filtered on a 2.6 cm (I.D.)×43 cm (long) column of Sephadex G-200 with 2 M NaCl as irrigant (A). Material in pooled fractions containing either HMWATHF (first 9% of peak) or LMWATHF (last 9% of peak) were separately fractionated on Sepharose-AT (B and C, respectively). Chromatography (as in FIG. 43) gave unbound, low and high affinity peaks 1, 2 and 3, respectively.
Figure 47:
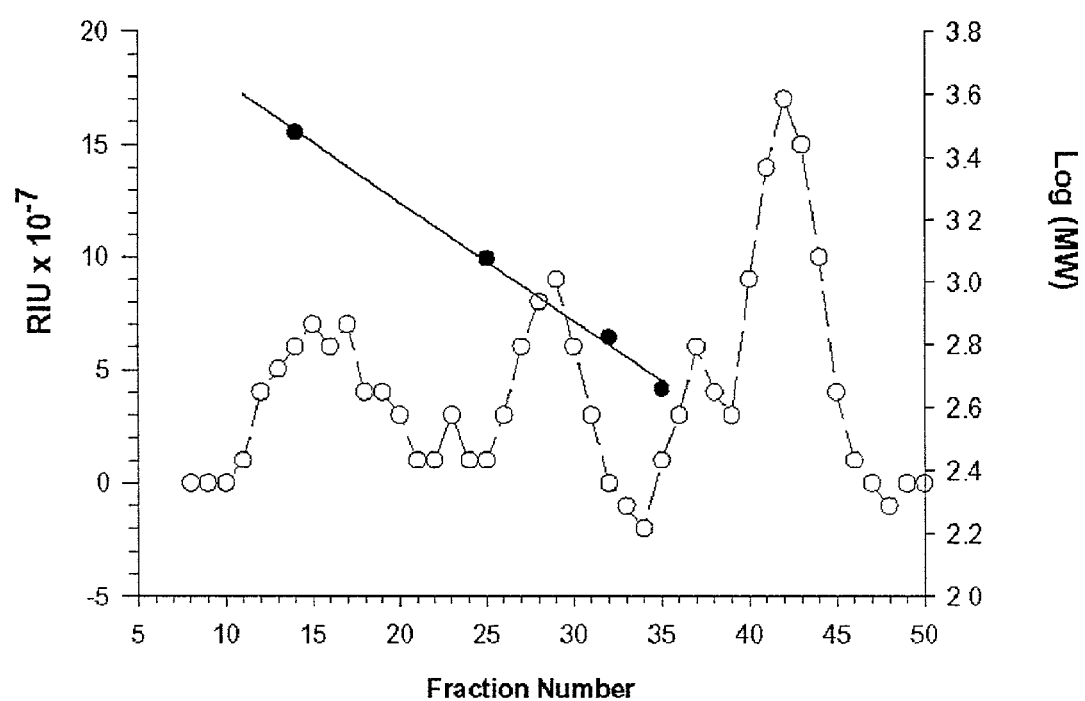
FIG. 47 Chromatography of protease treated low molecular weight fraction of covalent antithrombin-heparin complex (LMWATHF) on Bio-gel P-6. LMWATHF was incubated with catalytic amounts of a general protease (P-5147 from Sigma) at 37° C. and chromatographed on a Bio-gel P-6 column (1 cm I.D.×49 cm long). Elution was with 0.15 M NaCl and 1 mL fractions were collected (void volume=fraction 11). Heparin chains (fractions 12–20) were well separated from complex-type Asn-linked glycans (fractions 26–31) or free amino acids (fractions 35–45), as confirmed by control digests of uncomplexed antithrombin. Eluted material was detected by a refractive index detector and measurements given as refractive index units (RIU, O) relative to 0.15 M NaCl in the reference cell. Log (MW) of heparin fragment standards (●) versus elution position is also plotted.
Figure 48:
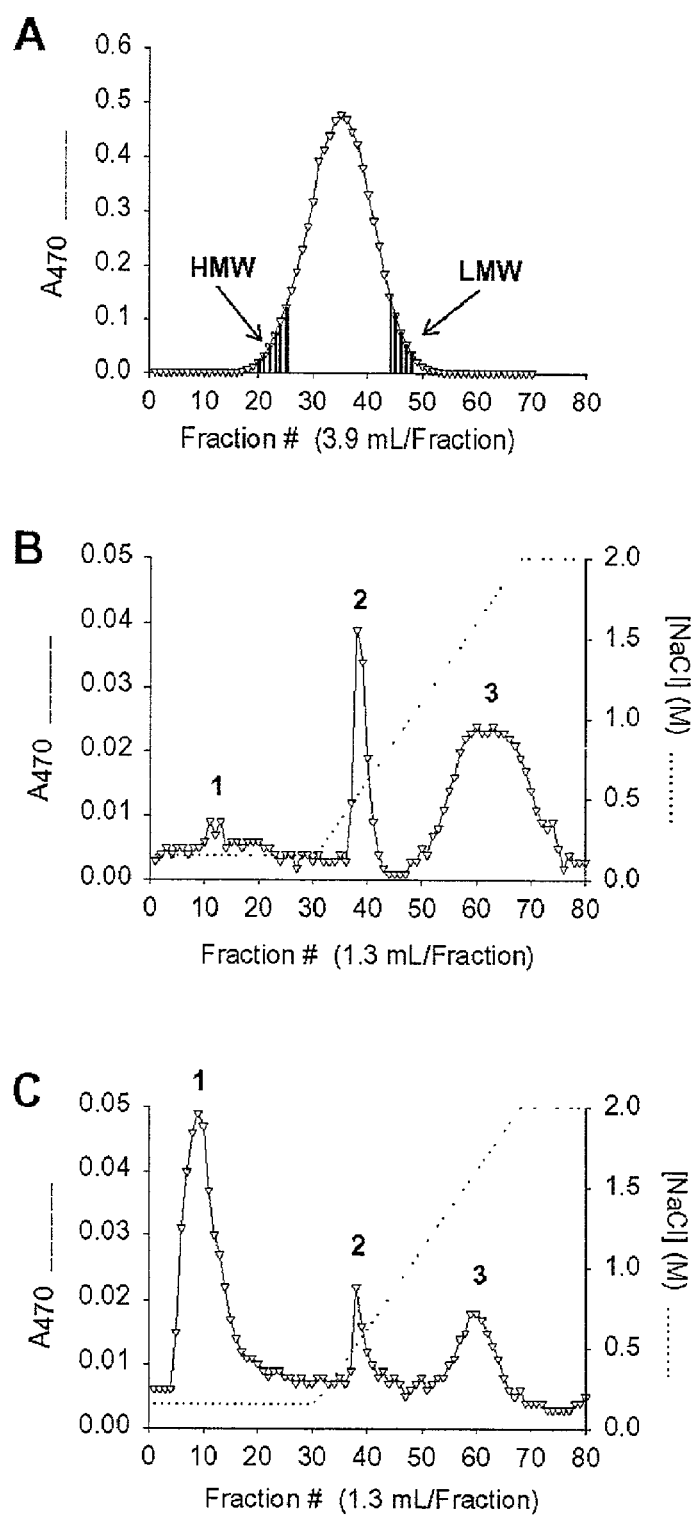
FIG. 48 Preparation of high molecular weight unfractionated heparin (HMWH) and low molecular weight unfractionated heparin (LMWH), followed by chromatography on Sepharose-antithrombin (Sepharose-AT). H (5 mg) was gel filtered on a 2.6 cm (I.D.)×43 cm (long) column of Sephadex G-200 with 2 M NaCl as irrigant (A). Material in pooled fractions containing either HMWH (first 9% of peak) or LMWH (last 9% of peak) were separately chromatographed on Sepharose-AT (B and C, respectively). Chromatography (as in FIG. 43) gave unbound, low and high affinity peaks 1, 2 and 3, respectively.

Sepharose-AT Chromatography of Different Molecular Weight Fractions of ATH and H—In order to further distinguish the sites within ATH heparin chains which were binding to immobilized AT, ATH was fractionated according to molecular weight by gel filtration on Sephadex G-200 under high ionic strength conditions. As a rule, ATH was gel filtered under high salt conditions (2 M NaCl) to prevent possible binding of the AT moiety in one ATH molecule with the pentasaccharide on the heparin chain in another ATH molecule. However, no differences in size exclusion profiles (which would be indicative of complexes forming due to intermolecular ATH-ATH interactions) were observed under low ionic strength (0.15 M NaCl) conditions. SDS PAGE analysis of the fractions from ATH material gel-filtered on Sephadex G-200 indicated that subpopulations of ATH molecules with discrete molecular weight ranges could be obtained across the peak (FIG. 45). ATH fractions with high molecular weight (first 2–9% of eluted material) or low molecular weight (last 2–9% of eluted material) were concentrated and designated as HMWATHF or LMWATHF, respectively (FIG. 46A). Since polydispersity of ATH results from variation in length of the heparin chains, HMWATHF and LMWATHF contained covalently-linked heparin with greater and smaller numbers of saccharide units, respectively. Previous gel filtration analyses of the heparin chains from HMWATHF and LMWATHF (isolated after protease treatment of the conjugate) indicated that the heparin moieties had >83 and <10 saccharide units, respectively. To further confirm the molecular weight range of heparin in the LMWATHF preparation, protease-treated LMWATHF was gel filtered on a calibrated Bio-gel P-6 column. The molecular weight for heparin prepared from the LMWATHF ranged from an estimated 11–6 saccharide units, with an average chain length of 9 saccharides (FIG. 47). Sepharose-AT chromatography of HMWATHF gave trace amounts (3% of recovery) of unbound material, followed by low and high affinity bound peaks (FIG. 46B) that had significant anti-factor Xa activities (210 and 762 U/mg heparin, respectively (Table 18)). Thus, the ATH fraction with longer heparin chains tended to have slightly improved binding to exogenous AT with somewhat increased catalytic activities compared to the parent unfractionated preparation. The LMWATHF was further fractionated on Sepharose-AT into a significant amount of unbound material (~40% of recovery), a low affinity peak and (relative to ATH and HMWATHF) a reduced amount of high affinity material (~30% of recovery (FIG. 46C)). Interestingly, although nearly half of the LMWATHF did not have affinity for exogenous AT, this unbound material possessed significant ability to catalyze reaction of factor Xa and AT (190 U/mg heparin (Table 18)). In contrast to the HMWATHF, catalytic activity of the high affinity peak of the LMWATHF was considerably reduced, tending towards the level of that for H (ANOVA for specific activity of LMWATHF vs H, p>0.05). As a control, H with similar chain lengths to that within HMWATHF and LMWATHF were prepared by gel filtration (FIG. 48A). Chromatography of high molecular weight H (HMWH) on the AT column resulted in<10% in the unbound fraction and an approximately 1:3 ratio of low:high affinity peaks (FIG. 48B). Anti-factor Xa catalytic activities of unbound, low affinity and high affinity HMWH peaks (0.5, 1.7 and 436 U/mg heparin, respectively (Table 18)) were similar to the values for the corresponding H peaks (ANOVA, p>0.05). In comparison, Sepharose-AT fractions of the HMWATHF had increased catalytic activities. The majority of LMWH molecules (~75%) were unable to bind to AT and had no activity (FIG. 48C), while the small proportion of LMWH molecules with high AT affinity had significant activity (277 U/mg heparin (Table 18)).

Analysis of anti-thrombin (anti-IIa) catalytic activity—All peaks obtained from chromatographies on Sepharose-AT were analyzed for the ability to catalyze reaction of added AT with thrombin (anti-IIa). The relative anti-IIa catalytic activities of unbound, low affinity and high affinity peaks eluted from Sepharose-AT were directly proportional to AT binding strength (Table 19). Furthermore, relative specific activities of peaks from ATH, H and AT+H chromatographies were similar to those measured by the anti-factor Xa assays (Table II). Anti-IIa catalytic activities (Table 19) of the high affinity material (peak 3) of LMWATHF and particularly LMWH were greatly reduced compared to high affinity peaks of other species (in each case p<0.05, (ANOVA)). This result would be expected given that thrombin requires longer chain heparin molecules in order to bridge both AT and the enzyme (Andersson, L. O. et al (1979) Thromb Res 15, 531–541). The fact that the LMWATHF had any significant anti-IIa activity was interesting, given that the heparin chain length was not likely to bridge both AT and thrombin. Subtraction of the activity due to direct reaction of LMWATHF with thrombin (non-catalytic activity) gave a value of 106 U/mg for the high affinity material (peak 3).

Figure 49:
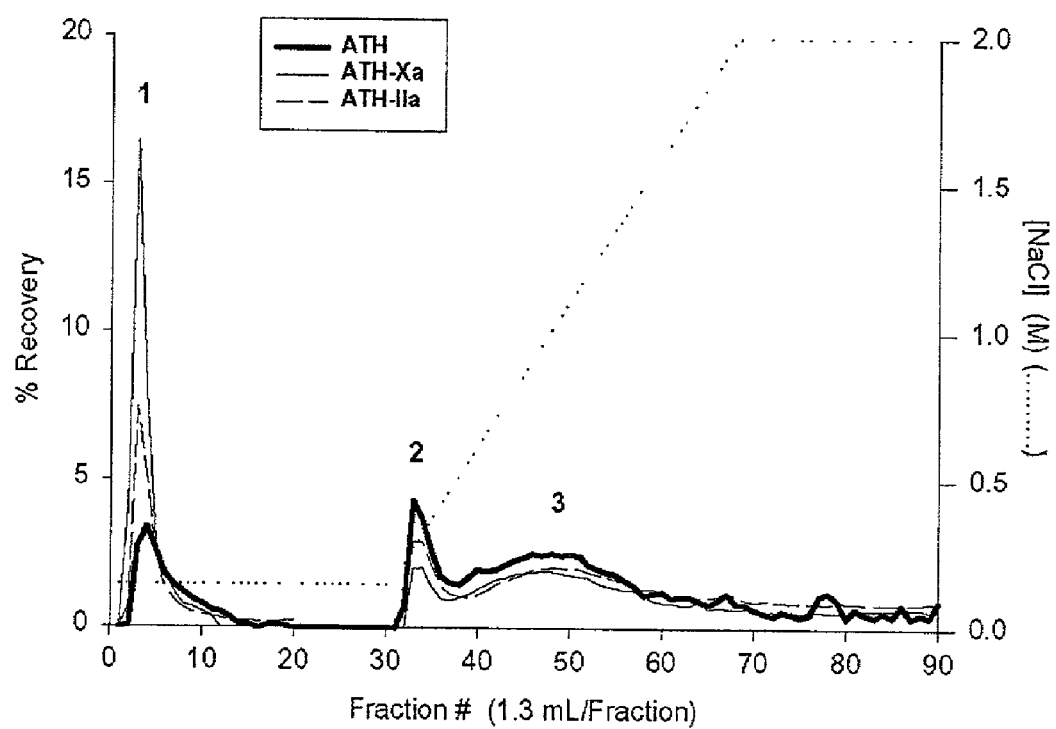
FIG. 49 Chromatography of inhibitor complexes of covalent antithrombin-heparin (ATH) on Sepharose-antithrombin (Sepharose-AT). Covalent inhibitor complexes of ATH with either factor Xa (factor Xa-ATH) or thrombin (thrombin-ATH) were prepared by titration of ATH to equivalence with the appropriate enzyme. Resultant inhibitor complexes (0.25 mg in terms of AT) were loaded onto 1.5 mL columns of Sepharose-AT (pre-equilibrated with 0.15 M NaCl in 0.01 M phosphate pH 7.3 buffer). Unbound material (peak 1) was washed off with 40 mL of 0.15 M NaCl, followed by elution of low affinity (peak 2) and high affinity (peak 3) material with a linear gradient (25 mL of buffered 0.15 M NaCl in the mixing chamber and 25 mL of buffered 2 M NaCl as limit solution) and 30 mL of 2 M NaCl. Fractions (1.3 mL) were collected and the percent of total eluate recovered from each chromatography was calculated.

Sepharose-AT Chromatography of Factor Xa-ATH and Thrombin-ATH Inhibitor Complexes—Covalent inhibitor complexes were formed by titration of ATH with either factor Xa or thrombin to ~100% equivalence, as shown by the detection of a small amount of remaining activity against chromogenic substrates. Treatment of the Xa- or thrombin-titrated ATH with heparinase, followed by SDS PAGE, showed that>95% of the AT (as ATH) had been converted to either factor Xa-AT or thrombin-AT bands. Factor Xa-ATH and thrombin-ATH complexes were used to test the effect of linkage to a serine protease on ATH's affinity for immobilized AT. Sepharose-AT chromatographic profiles for factor Xa-ATH and thrombin-ATH were compared to those for ATH fractionated on the same column (FIG. 49). An increase in the unbound fraction and a corresponding small decrease in bound material was noted for the inhibitor complexes relative to that for ATH (39%, 28% and 12% as unbound material for factor Xa-ATH, thrombin-ATH and free ATH chromatographies, respectively). There was, however, no significant change in the position of elution for either low affinity or high affinity peaks due to reaction with factor Xa or thrombin. Analysis of peaks for anti-factor Xa activity showed that for both factor Xa-ATH and thrombin-ATH, unbound (peak 1) and low affinity (peak 2) peaks had significantly decreased activities (<120 U/mg), while high affinity material (peak 3) had high activity (700–1000 U/mg). Anti-factor Xa assay of preformed factor Xa-ATH or thrombin-ATH complexes showed that activities were decreased relative to that for free ATH (~20% for factor Xa-ATH and ~5% for thrombin-ATH). Furthermore, reaction of factor Xa or thrombin with ATH in the presence of added AT resulted in a 20%–30% decreased formation of factor Xa-ATH or thrombin-ATH complexes.

Figure 50:
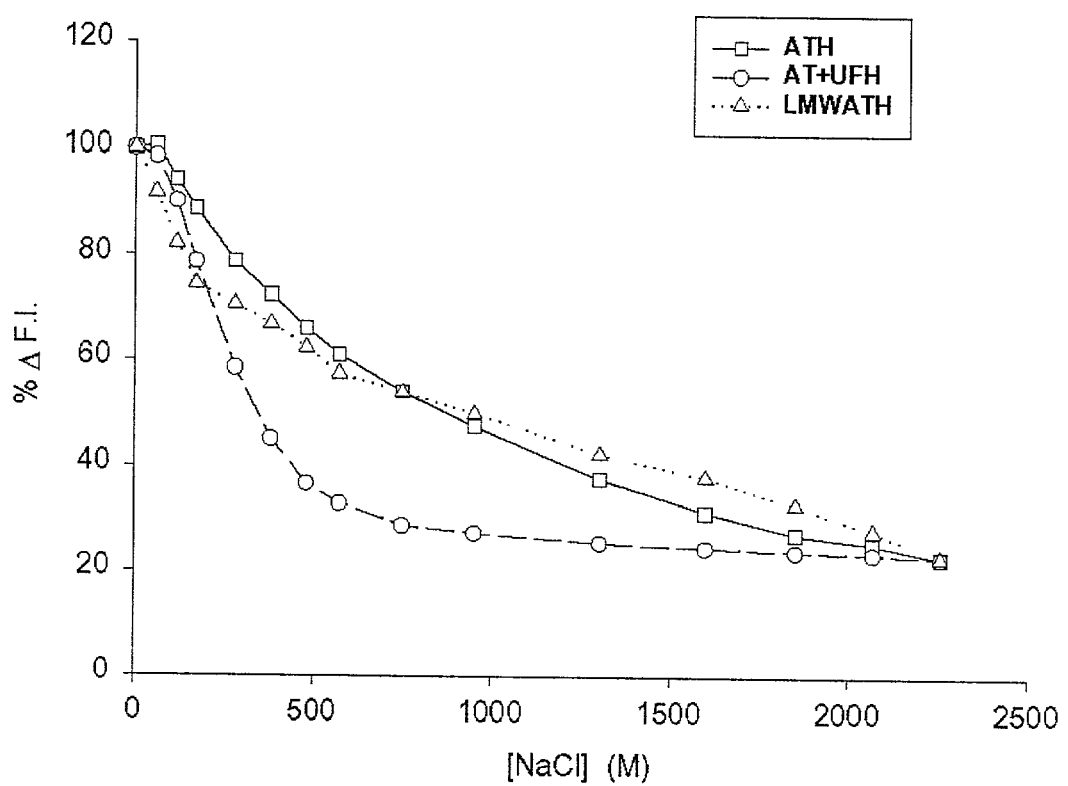
FIG. 50 Effect of NaCl concentration on the intrinsic fluorescence of covalent antithrombin-heparin (ATH) complexes. One mL buffered solutions (0.02 M Tris-HCl pH 7.4) of ATH (100 nM), a low molecular weight fraction of ATH (LMWATHF, 100 nM) and non-covalent mixture of antithrombin (AT, 100 nM)+unfractionated heparin (H, 234 nM) were titrated with buffered 5 M NaCl solutions of ATH, LMWATHF or AT+H, respectively. Intrinsic fluorescence (excitation=280 nm, emission=340 nm) of the solutions at 25° C. were measured after each addition of titrant (μL). Percent of the total difference in fluorescence intensity between that in buffer and at final equilibrium (2.258 M NaCl) was calculated (% F.I.), adjusted for % change in fluorescence of AT alone (at each [NaCl]) and plotted against NaCl concentration.

Fluorescence Titrations of ATH and AT●H With NaCl—Intrinsic fluorescence of the protein in ATH or AT+saturating H (2.34 fold molar excess to AT) was measured at increasing NaCl concentrations and the values corrected for any changes in the intrinsic fluorescence of control AT that was titrated with NaCl under the same conditions (FIG. 50). For both ATH and AT+H, [NaCl] was inversely proportional to the AT intrinsic fluorescence induced by heparin pentasaccharide binding. However, significantly greater NaCl concentrations were required to reduce the intrinsic fluorescence intensity of ATH compared to that for AT+H (FIG. 50). Fifty % reversal of the heparin-induced intrinsic fluorescence in ATH and AT+H occurred at NaCl concentrations of 0.57 M and 0.26 M, respectively. Similar fluorescence titrations of the LMWATHF gave complicated biphasic profiles with the low [NaCl] half of the curve showing very facile reversal of emission intensity, while the latter half of the curve was more coincident with that of ATH (FIG. 50). The proportion of species containing heparin with either low or high non-covalent affinity for AT (as indicated by the fluorescence data for the LMWATHF) was consistent with the Sepharose-AT chromatographic data in which ~40% of the LMWATHF was unbound (low affinity for exogenous AT) and had no catalytic activity (FIG. 46C and Table 18).

Figure 51:
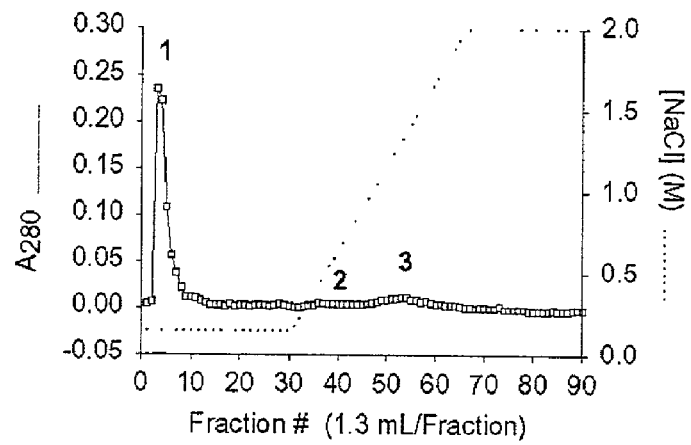
FIG. 51 Chromatography of covalent antithrombin-heparin complex (ATH), unfractionated heparin (H) and non-covalent complexes of antithrombin (AT)+H on Sepharose-heparin. (A) ATH (2 mg in terms of AT), (B) H (0.5 mg) or (C) AT (2 mg)+H (0.5 mg) were chromatographed on 1 cm (I.D.)×12 cm (long) columns of Sepharose-heparin using elution conditions similar to those for Sepharose-AT given in FIG. 43. Eluted material was detected by $A_{280}$ (protein) or protamine sulfate assay (heparin ($A_{470}$)) and appeared as either unbound, low affinity or high affinity peaks 1, 2 or 3, respectively. In the case of AT+H chromatographies, unbound (peak 1) AT (●) and H (∇) materials chromatographed separately.
Figure 51:
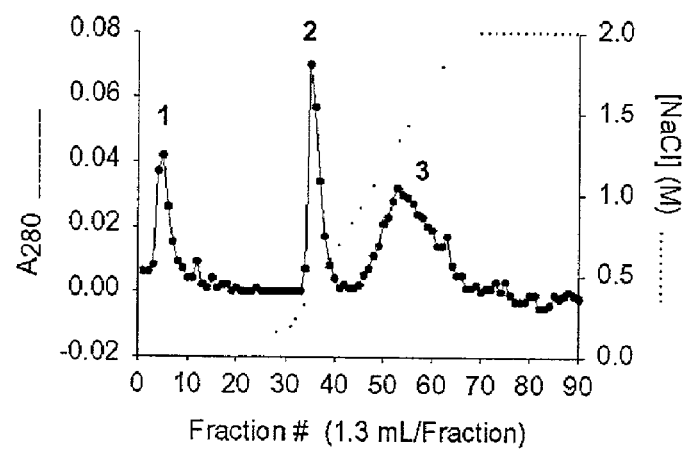
Figure 51:
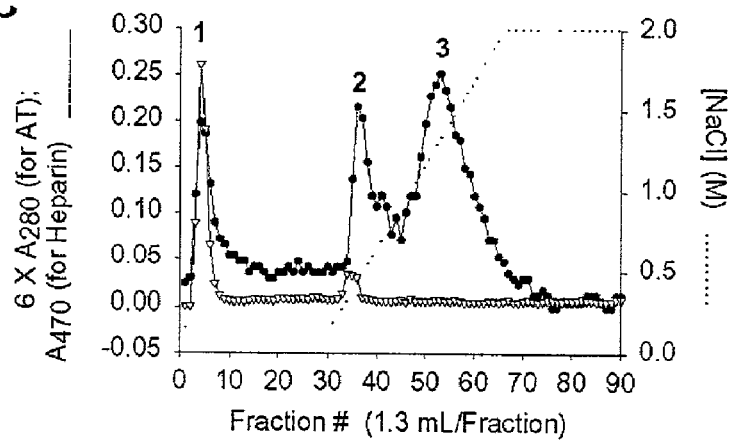

Chromatography of ATH and H on Sepharose-Heparin—ATH, AT and AT+H were chromatographed on columns of Sepharose-heparin to determine if heparin pentasaccharide binding sites could interact with the AT moiety in covalent or non-covalent complexes of AT and heparin (FIG. 51). In contrast to the results from chromatography on Sepharose-AT, >95% of ATH was unable to bind to the immobilized heparin (FIG. 51A). Alternatively, application of AT to the heparin column gave 87% binding of the load (FIG. 51B). The small amount of AT which did not bind to the immobilized heparin (10%–12%) was not a result of column capacity because application of different loading amounts gave similar results. Fractionation of non-covalent mixtures of AT+H on Sepharose-heparin caused dissociation of the AT●H complexes (>84% of AT molecules bound and ~90% of H molecules unbound (FIG. 51C)) reminiscent of chromatography on Sepharose-AT. Thus, AT in non-covalent complexes with H could interact with immobilized heparin, while AT in covalent ATH complexes could not. Evidence that the lack of affinity of AT in ATH for Sepharose-heparin was due to the covalent linkage to heparin was obtained by chromatography of a mixture of free AT with H' (heparin released from ATH by protease). Unlike ATH, AT in AT●H' complexes bound to Sepharose-heparin while the H' passed through unretarded (similar to that for AT●H (FIG. 51C)).

DISCUSSION

Inhibition of factor Xa or thrombin by AT is potentiated by H due, in part, to binding of the serpin to a pentasaccharide sequence on the GAG which, in turn, allosterically activates the inhibitor (Olson, S. T. et al (1992) J Biol Chem 267, 12528–12538). After reaction of factor Xa/thrombin with AT●H, the enzyme-serpin complex dissociates from H leaving the GAG available for catalysis of another factor Xa/thrombin+AT reaction (Byun, Y. et al (1996) J Biomed Mater Res 30, 423–427). A highly active covalent complex of AT and heparin (ATH) has been studied to investigate the reaction steps involved in the turnover of heparin during reaction of factor Xa and thrombin with permanently stabilized AT●H.

ATH has been shown to exhibit potent catalytic activity in the reaction of AT with factor Xa and thrombin (Chan, A. K. et al (1997) J Biol Chem 272, 22111–22117). This finding was surprising given that covalently-linked AT and heparin were unable to completely dissociate after formation of inhibitor complexes by direct reaction with factor Xa or thrombin (Chan, A. K. et al (1997) J Biol Chem 272, 22111–22117; Berry, L. et al (1998) J Biochem 124, 434–439). One possible mechanism that might explain ATH's catalytic activity was the presence of a second AT-binding pentasaccharide sequence on the covalently-linked heparin chain which was separate from the one which activates the conjugate's own AT moiety. Although studies showed that ~30–40% of ATH complexes contained 2 pentasaccharide units per molecule (Berry, L. et al (1998) J Biol Chem 273, 34730–34736), specific catalytic activities of the conjugate were ~1.8–2 fold greater than that of the H fraction with high affinity for AT (Chan, A. K. et al (1997) J Biol Chem 272, 22111–22117). Thus, in order to further investigate the basis for ATH's catalytic properties, experiments were performed to probe the accessibility of the pentasaccharide site which interacts with the covalently-linked AT.

Deductions from results of interaction studies with ATH relied on precise determination of the structural components of the conjugate. Previously, the content of heparin in ATH was analyzed by alcian blue staining of SDS PAGE gels of protease-treated ATH and the stain density was compared with that of known amounts of standard H using laser densitometry (Chan, A. K. et al (1997) J Biol Chem 272, 22111–22117). This methodology using alcian blue staining for heparin quantitation has been validated previously by a number of investigators. A large molecular weight range (1000–30000) of heparin isolated from Sigma heparin starting material or other commercial LMWHs and HMWHs have been analyzed and no significant difference in stain bound per mg heparin loaded was found. The intensity of alcian blue stain bound per mg of GAG is the same for heparin, heparan sulfate, dermatan sulfate, condroitin-4-sulfate and chondroitin-6-sulfate, in agreement with the work of Bartold and Page (Bartold, P. M. et al (1985) Anal Biochem 150, 320–324). Many other reports support the validity of cationic staining (alcian blue, toluidine blue) for quantitation of GAGs with varying molecular weights (Volpi, N. et al (1995) Biochem Biophys Acta 1243, 49–58; Breen, M. et al (1970) Anal Biochem 35, 146–159; Moller, H. J. et al (1993) Anal Biochem 209, 169–175; Krueger, R. C. et al (1987) Anal Biochem 167, 295–300). Small fraction samples were analyzed for heparin using a protamine sulfate turbidimetric assay. This protamine test for heparin was employed because of its very high sensitivity (<1 µg/mL could be detected) compared to other know methods. Also, data showing that similar protamine turbidimetric responses are given for a wide molecular weight range (300 to 25000) of Sigma and other heparins have been reported previously with this method (Hatton, M. W. C. et al (1980) Anal Biochem 106, 417–426).

Rigorous analyses of ATH for protein and heparin content gave further verification that the conjugate contained, on the average, one heparin chain per AT molecule. The mole concentration of ATH solutions in terms of AT (calculated from amino acid analyses of acid hydrolysates and the known amino acid sequence) was divided into the number of moles of ATH heparin (number-average molecular weight=15400 (FIG. 44)) determined from 3 different mass assay procedures. Analysis of all data resulted in the conclusion that the heparin:AT mole ratio was statistically consistent with that of a 1:1 complex. This outcome verified analyses carried out previously by different methods (Chan et al found the heparin:AT molar ratio in ATH to be 1.1 (Chan, A. K. et al (1997) J Biol Chem 272, 22111–22117)). Given that ATH molecules contained one heparin chain per AT, the proportions of ATH molecules with different binding affinities could be easily compared by measuring the amount of AT (by absorbance) in each peak. Heparin mass analyses (although less sensitive) of pooled fractions with different affinities for Sepharose-AT confirmed this assumption.

Fractionation of ATH on immobilized AT resulted in >74% high affinity binding (FIG. 43A). Thus, since the vast majority of ATH molecules could form ATH●AT complexes but only a relative minority of the heparin chains in ATH contain 2 pentasaccharides (Berry, L. et al (1998) J Biol Chem 273, 34730–34736), most of the ATH that possesses only one pentasaccharide was able to bind tightly to exogenous AT. Although the heparin component in ATH remains covalently attached to AT, added AT molecules are able to compete for binding to the pentasaccharide sequence that causes the AT moiety in ATH to be in an active conformation. Similar to covalent ATH, immobilized AT was able to compete for binding to H in AT●H complexes, resulting in displacement of the AT (FIG. 43C). Heparin chains from ATH (H') were isolated after protease treatment of the conjugate. Chromatography of H' on Sepharose-AT showed that the vast majority of ATH heparin contained high affinity binding sites (FIG. 44), verifying that the GAG component of ATH has pentasaccharide sites which would be capable of binding to exogenous AT. Further analysis of peaks from the Sepharose-AT chromatographies revealed that binding affinity was directly proportional to the specific catalytic activity. For non-covalently linked heparin, only the material with high affinity binding (peak 3) likely contained heparin molecules with high specificity AT-binding sites (only high affinity peak 3 had significant anti-factor Xa activity (Table 17)). In the case of ATH, since the pentasaccharide that interacts with ATH's AT might be sterically hindered (due to the covalently-linked AT), lower affinity material (peak 2) might retain significant catalytic activity that would be exhibited in the anti-factor Xa assays once factor Xa-ATH is formed. In fact, significant catalytic activities were observed in ATH fractions with decreased AT-affinity as evidence of this (Tables 17 and 18). ATH fractions with high AT-affinity were 1.53 times greater in anti-factor Xa activity than that of high affinity H material (Table 17). Rosenberg et al have previously shown that the subfraction in commercial H that has 2 AT binding sites per molecule has a greater specific activity than that for H with only 1 interaction site for AT (738 USP units/mg compared to 363 USP U/mg (Rosenberg, R. D. et al (1979) Biochem Biophys Res Comm 86, 1319–1324)) due to greater pentasaccharide density along the chain. Comparison of the results with those of Rosenberg et al indicates that the specific activities of high affinity ATH and H are in the range of that for 2 pentasaccharide and 1 pentasaccharide containing H chains, respectively. Closer inspection reveals, however, that the ratio of catalytic activity for 2 pentasaccharide heparin to that for 1 pentasaccharide heparin is significantly greater than the ratio of high affinity ATH activity to high affinity H activity (2.0 compared to 1.53). This would be expected, given that the AT-binding fraction of ATH contains significant amounts of 1 pentasaccharide heparin chains and the AT-binding fraction of H must contain some 2 pentasaccharide molecules.

An alternative hypothesis for the Sepharose-AT binding results was that covalently-linked AT may be capable of intermolecular binding to the second (free) pentasaccharide in 2 pentasaccharide ATH molecules. Thus, in some cases, the immobilized AT might be simply dissociating ATH dimers. In an attempt to address this possibility, as well as confirm the direct interaction of exogenous AT with the intramolecular pentasaccharide binding site for ATH's AT, the ATH fraction containing heparin chains that were<11 monosaccharides in length were isolated. Since ATH of this size (representing ≦5% of ATH preparations) cannot contain 2 pentasaccharides, no excess (free) AT binding sites are available. Sepharose-AT chromatograms of LMWATHF showed that ~50% bound to AT (FIG. 46C), which gave strong evidence for the direct competition of exogenous AT for ATH's intramolecular pentasaccharide binding site. Furthermore, the specific catalytic activity of heparin chains in LMWATHF complexes that bound to AT (560 U/mg (Peak 3, Table 18)) was closer to that for high affinity H (463 U/mg (Table 17)) than that for the corresponding AT-binding peak of ATH (708 U/mg (Table 17)), which is in agreement with the fact that most high affinity H molecules have only ~1 pentasaccharide. However, a significant proportion of the LMWATHF was unable to bind to Sepharose-AT. It is possible that the covalent linkage of heparin to AT in ATH may sometimes occur at more internal lysyl residues or the aldose linkage residue may be located at the start of the actual pentasaccharide sequence. Steric hindrance in the conjugates arising from either of these linkage situations might be too difficult for the Sepharose-AT to overcome. Chromatography of HMWATHF lead to almost complete binding of the load (FIG. 46B). Previously, it has been found that multi-pentasaccharide H tends to occur on long chain molecules (Rosenberg, R. D. et al (1979) Biochem Biophys Res Comm 86, 1319–1324; Jacobsson, K.-G. et al (1986) Biochem J 240, 625–632). Analyses of the specific activity of the HMWATHF high affinity peak gave results (762 U/mg (Table 18)) suggestive that a high proportion of the conjugates contain 2 pentasaccharide chains. Thus, a significant amount of the interactions between the HMWATHF and immobilized-AT may have occurred through a second pentasaccharide on the covalently linked heparin chain. Control experiments using low and high molecular weight fractions of H gave relatively similar results on Sepharose-AT to those for LMWATHF and HMWATHF. While<30% of LMWH bound to immobilized AT (FIG. 48C), >70% of HMWH bound to the column (FIG. 48B).

Interestingly, the specific activity data given in terms of units/mg illustrate a fascinating property of HMWATHF (or HMWH) chains that have 2 pentasaccharides compared to LMWATHF (or LMWH) chains with one pentasaccharide. By logic, a heparin molecule that contains 1 pentasaccharide should have the same activity in units/mg as another heparin molecule that has 2 pentasaccharides but is twice the chain length. However, Rosenberg et al (Rosenberg, R. D. et al (1979) Biochem Biophys Res Comm 86, 1319–1324) showed that while 20000 molecular weight heparin with 2 pentasaccharide AT-binding sites had a specific activity of 738 U/mg, 7000 molecular weight heparin with 1 pentasaccharide had a specific activity of 363 U/mg. Thus, in terms of activity/heparin molecule, Rosenberg's 2 pentasaccharide heparin was 14.8 U/nmole while his 1 pentasaccharide heparin was 2.54 U/nmole. The results were consistent with this finding, in that high affinity fractions of the HMWATHF and HMWH both had higher U/mg than their low molecular weight counterparts (Table 18). A rationale to explain why AT selects for enrichment of 2-pentasaccharide heparin during ATH formation is that the mean free distance of intramolecular diffusion between pentasaccharides in 2-pentasaccharide heparin molecules is less than that for intermolecular diffusion.

As expected, catalytic anti-IIa activity of high affinity fractions of ATH chromatographed on Sepharose-AT were several-fold higher than that for H or AT+H (Table 19). Previously, it has been shown that heparin chains of>18 saccharides in length are required to bridge both AT and thrombin during catalysis of thrombin inhibition (Danielsson, A. E. et al (1986) J Biol Chem 261, 15467–15473). Thus, it was surprising that LMWATHF (with heparin chains<12 saccharides in length (FIG. 47)) possessed significant (albeit reduced) anti-IIa catalytic activity. The heparin chains in LMWATHF, although short in length, may have a higher negative charge density that may assist in greater electrostatic attraction to thrombin.

Further characteristics of the ATH catalytic mechanism were delineated. The effect of ATH reaction with factor Xa or thrombin on binding to Sepharose-AT was investigated in order to understand the capability of ATH-inhibitor complexes to catalyze further inhibition. Although >60% of either enzyme-ATH or ATH alone were bound by immobilized AT (FIG. 49), significantly more unbound material was recovered in the case of thrombin-ATH (28%) and, particularly, factor Xa-ATH (39%) inhibitor-complexes compared to ATH (18%). Thus, complexation with factor Xa or thrombin may cause added steric hindrance of the ATH pentasaccharide towards exogenous AT. This hypothesis was confirmed by the fact that enzyme-ATH complexes (particularly factor Xa-ATH) had reduced anti-factor Xa activities compared to that of free ATH. Conversely, the presence of a vast excess of added AT inhibited the formation of enzyme-ATH inhibitor complexes, presumably by binding of the exogenous AT to the pentasaccharide site occupied by the AT in ATH. Increased physical obstruction by bound factor Xa or thrombin may be more critical in the case of molecules in the LMWATHF that have smaller chain lengths for the initial electrostatic attraction to the immobilized AT (compare with FIGS. 46B and 46C). These latter results for ATH of varying molecular weights or in the form of inhibitor complexes lead to studies of the relative affinity between the pentasaccharide and AT moieties. Direct determination of the binding of AT and heparin in ATH was accomplished by measuring the loss of intrinsic AT fluorescence when activating heparin is displaced (Berry, L. et al (1998) J Biol Chem 273, 34730–34736; Olson, S. T. et al (1981) J Biol Chem 256, 11065–11072). Greater [NaCl] was required for 50% reversal of the heparin-induced intrinsic fluorescence in ATH (FIG. 50); which is compliant with the fact that since AT and heparin are covalently linked, complete dissociation is prohibited (regardless of ionic strength, AT would always be in close proximity to the heparin binding site). Fluorescence titrations of the LMWATHF with NaCl gave a complicated profile. The fluorescence of the LMWATHF decreased rapidly with small additions of NaCl, followed by a more gradual reduction in fluorescence (similar to ATH) at higher ionic strengths (FIG. 50). Thus, a portion of the molecules in the LMWATHF contain weakly interacting protein and GAG while the remainder have AT and heparin which have strong intramolecular interactions. These data fit with the heterogeneity in affinity of different subfractions of LMWATHF for immobilized AT in that some heparin chains of the LMWATHF are more easily bound by exogenous AT, possibly due to decreased intramolecular association of AT and heparin. Binding of exogenous AT to molecules of LMWATHF that have strong intramolecular AT-pentasaccharide interactions may require longer GAG chains for initial intermolecular-electrostatic attractions. The molecules of the LMWATHF that did not bind to AT represented<3% of all ATH molecules. Finally, probing with exogenous heparin showed that while the majority of AT bound to immobilized heparin, almost all ATH passed freely through the Sepharose-heparin column (FIG. 51). Lack of ATH binding to immobilized heparin was probably due to strong negative charge repulsion between ATH GAG chains and heparin on the column. Since AT and heparin in ATH cannot dissociate, the heparin in ATH would likely be in too close a proximity (on a charge basis) for the immobilized heparin to bind to ATH's AT moiety. The likelihood that heparin was unable to access the AT in ATH because of electrostatic effects was further evidenced by the binding of Sepharose-heparin to AT in AT●H complexes via dissociation of the H (FIG. 51C). Furthermore, Sepharose-heparin chromatography of a mixture of AT+the heparin chains released from ATH by protease (H') resulted in binding of the AT and a lack of affinity for the H'. Finally, absence of ATH affinity for Sepharose-heparin was a further confirmation that intermolecular binding of ATH to other ATH molecules does not occur.

Originally, it was expected that the pentasaccharide bound by the AT in ATH might be hindered from other molecules since the AT in ATH is also covalently linked and cannot completely diffuse away from the ATH heparin chain (which can occur with AT that is only bound to a heparin molecule via the pentasaccharide (not covalently linked)). Although fluorescence data showed a resistance of the AT in ATH to be displaced from its pentasaccharide binding site (presumably because the covalent linkage still keeps the AT tethered to the heparin), displacement from these non-covalent interactions by NaCl does occur (FIG. 50). Also, experiments with the heparin produced from protease-treated ATH (H') verified that ATH heparin chains, on their own, interact with immobilized AT and immobilized H in a similar way to that of standard H (pentasaccharide units of ATH heparin are the same as that in standard H).

Results from the study of ATH catalytic mechanisms have several implications. Since exogenous AT can bind to covalently-linked AT-heparin, interchange of AT in AT●H complexes with free AT may occur through a displacement model. Alternatively, a mechanism can be envisaged in which free AT electrostatically attracts the GAG in ATH, from the side opposite to that of the covalently linked AT, and causes a rotation of the heparin about its helical axis so that the pentasaccharide is now in the correct orientation for ionic/hydrogen bonding to the exogenous AT. Also, since the off rate of AT bound to the pentasaccharide is relatively rapid (Hoylaerts, M. et al (1984) J Biol Chem 259, 5670–5677), the AT in ATH may frequently dissociate from its non-covalent interaction with the pentasaccharide on the covalently-linked heparin chain so that exogenous AT may bind and be activated. Notwithstanding which model describes transition states involved in AT complexation of ATH, it is clear that long distance dissociation of AT●H (which is impossible for ATH) is unnecessary in order for exchange with free AT to occur. Free AT may be able to access (or share) the pentasaccharide in AT●H complexes. Previous work has mapped out some of the AT residues involved in binding to the heparin pentasaccharide (Smith, J. W. et al (1987) J Biol Chem 262, 11964–11972; Blackburn, M. N. et al (1984) J Biol Chem 259, 939–941; Ersdal-Badju, E. et al (1997) J Biol Chem 272, 19393–19400; Fan, B. et al (1993) J Biol Chem 268, 17588–17596; Okajima, K. et al (1989) Thromb Haemostas 61, 20–21; Okajima, K. et al (1993) Blood 81, 1300–1305; Owen, M. C. et al (1987) Blood 69, 1275–1279). Recent experiments using an AT mutant have shown that $Arg^{129}$ binds the heparin pentasaccharide cooperatively with other residues leading to an induced fit to the heparin molecule that locks the AT into its activated state (Desai, U. et al (2000) J Biol Chem 275, 18976–18984). Binding of AT to the pentasaccharide occurs by interaction with the first 3 saccharide residues from the non-aldose terminus (Petitou, M. et al (1997) Glycobiology 7, 323–327), which causes charge neutralization and helix D elongation leading to the induced fit which is stabilized by interaction of the remaining 2 saccharide residues to $Arg^{46}$ and $Arg^{47}$ (Huntington, J. A. et al (2000) J Biol Chem 275, 15377–15383). Thus, initial stages of exogenous AT binding to ATH may involve reversal of the charge interactions between the aldose disaccharide unit of the pentasaccharide and Arg residues in the ATH molecule. Further charge attraction of the approaching AT to the ATH heparin moiety would then allow for the proper alignment of groups in the GAG for tight binding to the added AT. Studies with model compounds have shown that addition of saccharides (2) at the pentasaccharide aldose terminus gives a possible shift in positioning on the AT to an extended heparin-binding site at ≧0.2 ionic strength and a 2-fold increase in affinity (Belzar, K. J. et al (2000) J Biol Chem 275, 8733–8741). These findings may, in part, explain the strong ATH intramolecular pentasaccharide binding observed by fluorescence titration if the pentasaccharide in ATH is a few saccharide units away from the covalent linkage point on the AT.

All patents, patent applications and publications described herein are incorporated by reference whether specifically incorporated previously or not.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above may be used in various combinations. All publications and patent documents cited in this application are incorporated by reference in their entirety for all purposes to the same extent as if each individual publication or patent document were so individually denoted. Certain changes and modifications may be practiced within the scope of the appended claims.

All publications, patents and patent applications mentioned herein are incorporated herein by reference for the purpose of describing and disclosing methodologies, procedures, products, etc. which are reported therein which might be used in connection with the invention. Nothing herein is to be construed as an admission that the invention is not entitled to antedate such disclosure by virtue of prior invention.

It must be noted that as used herein and in the appended claims, the singular forms "a", "an", and "the" include plural reference unless the context clearly dictates otherwise.

TABLE 1

Characteristics of Covalent ATH Products

| PRODUCT | MOLAR RATIO HEP:AT | ACTIVATING GROUPS PER HEP | MOL. WT. (SDS PAGE) | ANTI-Xa* | ANTI-IIa* |
|---|---|---|---|---|---|
| BERRY et al. | 1.1 | 1 | 69 kD–100 kD | | >98% |
| COLLEN et al. | 0.8–0.9 | 2.1 | | 65% | #65% |
| BJORK et al. | 0.7 | 1 | | 82% | UNDETECTABLE |

*Activity of heparin in complex compared to unmodified starting heparin

| PRODUCT | MOLAR RATIO GAG:AT | ACTIVATING GROUPS PER GAG | MOL. WT. (SDS PAGE) | ANTI IIa* |
|---|---|---|---|---|
| HCH | 1.1 | 1 | 70 kD–115 kD | >90% |
| HCD | 1.4 | 1 | 78 kD–150 kD | >90% |

*Percent of molecules active against IIa

TABLE 2

| PRODUCT | BIMOLECULAR RATE CONSTANT ($M^{-1}s^{-1}$) | 2nd ORDER RATE CONSTANT ($M^{-1}s^{-1}$) | EFFECT OF >10 FOLD MOLAR EXCESS ADDITION OF HEPARIN |
|---|---|---|---|
| BERRY et al. | $1.3 \times 10^9 \pm 2 \times 10^8$ | $3.1 \times 10^9 \pm 4 \times 10^8$ | INHIBITION OF ANTI-IIa ACTIVITY |
| COLLEN et al. | $3 \times 10^4$ | $6.7 \times 10^8$ | ANTI-Xa ACTIVITY DOUBLED |
| BJORK et al. | — | — | |

TABLE 3

Anti-Factor Xa Activity of ATH Over Time When Stored at 4° C.

| Date of Assay | Days After Start of Storage at 4° C. | Anti-Factor Xa Activity AT Added (u/ml) | Anti-Factor Xa Activity No AT added (u/ml) |
|---|---|---|---|
| Nov. 23, 1995 | pre | 1630 | not done |
| Nov. 12, 1995 | 5 | 1740 | 107 |
| Dec. 20, 1995 | 14 | 1760 | not done |
| Jan. 23, 1996 | 48 | not done | 62 |
| Mar. 13, 1996 | 96 | not done | 0.52 |

TABLE 4

Anti-Factor Xa Activity of Gel Filtered ATH

| Fraction | Anti-Factor Xa Activity (u/ml) | Specific Activity of ATH if the Activity Was Due to ATH Alone (u/mg heparin) | Specific Activity of Free Heparin If the Activity Was Due to Free Heparin Alone (u/mg heparin) |
|---|---|---|---|
| 22 | 83.25 | 825.88 | 167101.6 |
| 24 | 73.26 | 634.10 | 34410.5 |
| 26 | 79.92 | 817.10 | 14468.3 |
| 28 | 43.29 | 658.10 | 4234.6 |
| 30 | 33.00 | 1005.3 | 3141.2 |

TABLE 5

Second Order Rate Constants for ATH

| | Second Order Rate Constants ($M^{-1}s^{-1}$) | Fold Increase Over AT Alone |
|---|---|---|
| AT | $7.0 \times 10^3$ | |
| AT + SH (saturating in AT) | $1 \times 10^8$ | 14000 |
| ATH | $3.1 \times 10^9$ | 440,000 |

TABLE 6

Comparison of Effect of Firbin in Monomer on Rate of Thrombin Inhibition by 100 nM ATH versus 100 nM H plus 200 mM AT

| Fibrin monomer concentration (uM) | Fold inhibition ATH | AT + H* |
|---|---|---|
| 0.0 | 1.00 | 1.0 |
| 0.5 | 1.03 | 30.0 |
| 1.0 | 1.23 | 38.0 |
| 4.0 | 1.24 | 58.1 |

*High affinity heparin. High affinity heparin is the ATIII binding fraction of heparin purified from standard SH.

TABLE 7

Rate of Thrombin (IIa) Inhibition By ATH vs High Affinity Heparin (HASH)

| Type of Thrombin | Inhibitors Used | k1 (1/min) (apparent for ATH, corrected for HASH + AT) | k1(alpha IIa)/k1(R93 IIa) |
|---|---|---|---|
| alpha IIa | ATH | 3.45 | 1.0 |
| R93 IIa | ATH | 4.19 | 1.2 |
| alpha IIa | HASH + AT | 63.79 | 1.0 |
| r93 IIa | HASH + AT | 0.14 | 0.002 |

TABLE 8

Pharmaco Kinetic Studies of ATH in Rabbits

| | AT Given | Heparin Given | Anti-Factor Xa Activity Given |
|---|---|---|---|
| 1. ATH | 2.75 mg/kg | 0.698 mg/kg | 544.3 u/kg |
| 2. AT + SH | 2.75 mg/kg | 0.698 mg/kg | 124.8 u/kg |
| 3. SH | | 0.698 mg/kg | 124.8 u/kg |
| 4. AT | 2.75 mg/kg | | |

TABLE 9

Half Life of ATH in Rabbits

| | t½ by Anti-Factor Xa In Rabbits | t½ by ELISA in Human AT in Rabbits | t½ Reported in Human |
|---|---|---|---|
| ATH | 2.4 hours | 2.6 hours | |
| AT + SH | 0.41 hours | 13 hours | |
| SH | 0.32 hours | | 1 hour |
| AT | | 13 hours | 66 hours |

TABLE 10

Amounts of Compound Administered Subcutaneously to Rabbits in Pharmaco Kinetic Study

| | AT Given | Heparin Given | Anti-Factor Xa Activity Given |
|---|---|---|---|
| 1. ATH | 4.6 mg/kg | 1.2 mg/kg | 936 u/kg |
| | 5.4 mg/kg | 1.7 mg/kg | 1325 u/kg |
| 2. AT + SH | 4.6 mg/kg | 1.2 mg/kg | 216 u/kg |
| | 5.4 mg/kg | 1.7 mg/kg | 306 ug/kg |
| 3. SH | | 1.2 mg/kg | 216 u/kg |
| | | 1.7 mg/kg | 306 u/kg |
| 4. AT | 4.6 mg/kg | | |
| | 5.4 mg/kg | | |

TABLE 11

Relative Effect of ATH, AT + SH, SH alone, AT Alone and Saline on Experimental Bleeding Using a Rabbit Bleeding Ear Model

| | AT Given | Heparin Given | Anti-Factor Xa Activity Given |
|---|---|---|---|
| 1. ATH | 1.10 mg/kg | 0.279 mg/kg | 217.7 u/kg |
| 2. AT + SH | 1.10 mg/kg | 0.279 mg/kg | 49.9 u/kg |
| 3. SH | — | 0.279 mg/kg | 49.9 u/kg |
| 4. AT | 1.10 mg/kg | — | — |
| 5. Saline | — | — | — |

TABLE 12

In Vitro physical properties of coated surfaces

| Property | ATH | Hirudin | Heparin |
|---|---|---|---|
| Graft Density (moles/m²) | $1.98 \times 10^{-7} \pm 6.4 \times 10^{-8}$ | $9.7 \times 10^{-9} \pm 1.3 \times 10^{-9}$ | $3.14 \times 10^{-8} \pm 1.7 \times 10^{-8}$ |

TABLE 12-continued

In Vitro physical properties of coated surfaces

| Property | ATH | Hirudin | Heparin |
|---|---|---|---|
| Leaching[1] (U/ml) | <0.01 | <0.01 | <0.01 |
| Storage-life[2] (month) | >2 | >1 | >2 |

[1]Plasma anti-factor Xa or anti-factor IIa (Hirudin) activity after incubation of 2 cm segments in 3.8 ml of citrated blood for 96 h at 4° C. Detection limit is 0.01 U/mL.
[2]Time over which coated surface can be maintained in 0.15 M NaCl at 4° C. and still retain ≥90% of the activity for inhibition of thrombin measured immediately after preparation.
Values represent mean ± 1 SEM, n ≥ 3.

TABLE 13

Antithrombin Activity of Coated Surfaces

| Coating | Direct thrombin inhibition activity (moles neutralized/m$^2$) | $^{125}$I-AT binding (moles/m$^2$) |
|---|---|---|
| ATH | $1.09 \times 10^{-8} \pm 6 \times 10^{-10}$ | $1.66 \times 10^{-8} \pm 2.0 \times 10^{-9}$ |
| Hirudin | $5.5 \times 10^{-9} \pm 9 \times 10^{-10}$ | Not Done |
| UFH Coated | $<4 \times 10^{-11}$ ND* | $1.8 \times 10^{-9} \pm 5 \times 10^{-10}$ |
| Non-Coated | $<4 \times 10^{-11}$ ND* | $<1 \times 10^{-10}$ |

Values represent mean ± 1 SEM, n ≥ 3. Detection limit for the direct thrombin inhibition activity assay was $4 \times 10^{-11}$ moles neutralized/m$^2$. Detection limit for the $^{125}$I-AT binding was $1 \times 10^{-10}$ moles/m$^2$.

TABLE 14

In vivo Plasma Thrombin Generation in a Vascular Graft Model

| | | Surface Coating | | |
|---|---|---|---|---|
| Analysis | Time (min) | ATH | Hirudin | Non-treated |
| [TAT][1] | 60 | −3.0 ± 1.1 | 16.4 ± 21.8 | 11.6 ± 16.0 |
| | 120 | −13.3 ± 0.1 | 10.7 ± 5.4 | 19.1 ± 3.0 |
| | 180 | 12.8 ± 13.1 | 37.2 ± 16.1 | 34.1 ± 4.4 |

[1][TAT] values are in picomolar (pM) and represent the net change from baseline values obtained prior to insertion of endoluminal grafts. TAT = Thrombin-antithrombin inhibitor complex
Values are mean ± 1 SEM, n ≥ 3.

TABLE 15

Effect of soluble fibrin monomer on the rate of inhibition of either α-thrombin (IIa) or thrombin with reduced heparin-binding affinity (RA-IIa) by either covalent antithrombin-heparin complex (ATH) or non-covalent mixture of antithrombin (AT) and heparin (H).

| Enzyme | [Fibrin] (nM) | Reactions with ATH $k_2$ (M$^{-1}$min$^{-1}$) | Reactions with AT + H $k_2$ (M$^{-1}$min$^{-1}$) |
|---|---|---|---|
| IIa | 0 | $2.26 \pm 0.093 \times 10^9$ | $3.02 \pm 0.051 \times 10^8$ |
| | 500 | $2.19 \pm 0.063 \times 10^9$ | $7.93 \pm 0.784 \times 10^6$ |
| | 1000 | $1.83 \pm 0.029 \times 10^9$ | ND |
| | 4000 | $1.01 \pm 0.127 \times 10^9$ | $5.25 \pm 0.271 \times 10^6$ |
| RA-IIa | 0 | $2.97 \pm 0.497 \times 10^8$ | $9.85 \pm 2.71 \times 10^5$ |
| | 4000 | $5.50 \pm 0.970 \times 10^8$ | $5.28 \pm 0.002 \times 10^5$ |

Pseudo first-order rate constants ($k_1$) were determined under pseudo-first order conditions using a discontinuous inhibition assay for remaining enzyme chromogenic activity. Apparent second order rate constants ($k_2$) were calculated by dividing $k_1$ values by the inhibitor concentrations. The effects of fibrin on the inhibition of IIa or RA-IIa by ATH or AT + H were assessed.
Values are means ± SEM with n ≥ 2.
ND = not determined.

TABLE 16

Comparative analyses for heparin content in covalent antithrombin-heparin complex. Covalent antithrombin-heparin complex (ATH) was analyzed by 3 different methods for heparin (H) content. Antithrombin (AT) in ATH was determined using an $\epsilon_{280}^{0.1\%}$ of 0.641 (that was verified by amino acid analysis of acid hydrolyzed ATH) and a molecular weight for AT of 57769 (calculated from the known protein sequence and N-linked glycan content). Background values measured in control samples of AT alone were subtracted to give corrected values for the H in ATH. Given a number-average molecular weight (Mn) of 15400 for the H covalently-linked to AT in ATH (determined by gel filtration of the product from protease-treated ATH), the mole ratio of H:AT in ATH was calculated. Results are mean ± SE (n ≥ 3).

| ANALYTICAL METHOD | ATH (μg H/nmole AT) | AT (μg/nmole AT) | ATH CORRECTED for BACKGROUND AT (μg H/nmole AT) | H:AT in ATH (mole:mole) |
|---|---|---|---|---|
| CARBAZOLE | 19.27 ± 1.32 | 1.86 ± 0.34 | 17.4 ± 1.3 | 1.13 ± 0.09 |
| AZURE A | 19.17 ± 0.19 | 0.17 ± 0.04 | 19.0 ± 0.2 | 1.23 ± 0.01 |
| ALCIAN BLUE | 15.6 ± 0.6 | 0.0 | 15.6 ± 0.6 | 1.03 ± 0.03 |

TABLE 17

Anti-factor Xa activities of covalent antithrombin-heparin complex and standard heparin chromatographed on Sepharose-AT. Covalent antithrombin-heparin complex (ATH), unfractionated heparin (H'), non-covalent mixture of antithrombin (AT) + H (1:1 molar ratio) or heparin from ATH (H3) were fractionated on Sepharose-AT. The column was washed with buffered 0.15 M NaCl followed by elution with a linear NaCl gradient (0.15 M–2.0 M) and final high salt wash (2M). Elution profiles (determined either by protein absorbance or protamine sulfate heparin mass assay) appeared as 3 peaks: unbound (peak 1), low affinity (peak 2) and high affinity (peak 3). Fractions comprising each peak were pooled, concentrated and analyzed for heparin mass and activity (anti-factor Xa kit). Catalytic activities were determined as the ability to accelerate reaction of excess added AT with factor Xa (versus commercially available standard H). The units of activity were divided by the heparin mass to give specific activities (U/mg). Results are given as mean ± SE (n ≧ 2). See Experimental Procedures for details.

| COLUMN | ANTI-FACTOR Xa CATALYTIC ACTIVITY in U/mg (Proportion of each peak as a percent of total eluate given in brackets) | | |
|---|---|---|---|
| LOAD | PEAK 1 | PEAK 2 | PEAK 3 |
| ATH | 231 ± 7 (12) | 112 ± 47 (14) | 708 ± 50 (74) |
| H | 0.4 ± 0.2 (41) | 8.4 ± 1.3 (17) | 463 ± 28 (43) |
| AT + H | 5.0 ± 0.4 (37) | 7.1 ± 0.1 (17) | 447 ± 16 (46) |
| H3 | 1.2 ± 0.1 (7) | 5.6 ± 0.1 (10) | 660 ± 5 (83) |

TABLE 18

Anti-factor Xa activities of high and low molecular weight fractions of covalent antithrombin-heparin complex and standard heparin chromatographed on Sepharose-AT. Covalent antithrombin-heparin complex (ATH) or standard heparin (H) were gel filtered to give high molecular weight fractions of ATH (HMWATHF) and H (HMWH) or low molecular weight fractions of ATH (LMWATHF) and H (LMWH). The separate fractions were chromatographed on Sepharose-AT. Elution profiles (determined either by protein absorbance or protamine sulfate heparin mass assay) appeared as 3 peaks: unbound (peak 1), or low (peak 2) and high affinity (peak 3) gradient eluted material. Each peak was concentrated and analyzed for heparin mass and activity (anti-factor Xa kit). Activities were determined as either non-catalytic (direct reaction alone with factor Xa) or catalytic (ability to accelerate reaction of excess added AT with factor Xa (versus commercial standard H)). Activity was divided by heparin mass to give specific activity (U/mg). Results are given as mean ± SE (n ≧ 2).

| COLUMN | ANTI-FACTOR Xa CATALYTIC ACTIVITY in U/mg (Proportion of each peak as a percent of total eluate given in brackets) | | |
|---|---|---|---|
| LOAD | PEAK 1 | PEAK 2 | PEAK 3 |
| HMWATHF | — (3) | 210 ± 23 (12) | 762 ± 49 (85) |
| LMWATHF | 190 ± 53 (39) | 174 ± 0.2 (30) | 560 ± 33 (31) |
| HMWH | 0.5 ± 0.0 (7) | 1.7 ± 0.0 (22) | 436 ± 50 (71) |
| LMWH | 0.6 ± 0.1 (75) | 1.7 ± 0.0 (7) | 277 ± 10 (18) |

TABLE 19

Anti-IIa activities of covalent antithrombin-heparin complex (ATH) and heparin (H) fractions chromatographed on Sepharose-AT. ATH or H were gel filtered to give high (HMWATHF and HMWH) or low (LMWATHF and LMWH) molecular weight fractions. Sepharose-AT chromatography gave unbound (peak 1), or low (peak 2) and high (peak 3) affinity material. Peaks were tested for heparin mass and activity (catalysis of thrombin inhibition by AT (anti-IIa kit)). Activity/mass gave specific activity (U/mg; mean ± SE (n ≧ 2)).

| COLUMN | ANTI-IIa CATALYTIC ACTIVITY in U/mg (Proportion of each peak as a percent of total eluate given in brackets) | | |
|---|---|---|---|
| LOAD | PEAK 1 | PEAK 2 | PEAK 3 |
| ATH | 223 ± 9.5 (12) | 146 ± 8.2 (14) | 636 ± 49 (74) |
| H | 9.1 ± 0.5 (41) | 40.0 ± 5.8 (17) | 266 ± 34 (43) |
| AT + H | 2.3 ± 0.0 (37) | 32.7 ± 1.6 (17) | 258 ± 9.5 (46) |
| HMWATHF | — (3) | 113 ± 2.4 (12) | 564 ± 37 (85) |
| LMWATHF | 47.0 ± 4.3 (39) | 73.5 ± 10 (30) | 120 ± 5.4 (31) |
| HMWH | 2.8 ± 0.1 (7) | 12.8 ± 0.1 (22) | 291 ± 33 (71) |
| LMWH | 3.2 ± 0.1 (75) | 15.7 ± 0.3 (7) | 67 ± 0.1 (18) |

We claim:

1. A method for reducing the thrombogenicity of a material by coating the material with a covalent conjugate comprising heparin linked to antithrombin III wherein the antithrombin III is directly covalently linked via its amino group to a terminal aldose residue of the heparin and the covalent linkage comprises an imine (>C=N—) formed between the amino group and C1 of the terminal aldose or the amine reduction product thereof (>C=H—NH—), or a pharmaceutically acceptable salt thereof.

2. A method for reducing the thrombogenicity of a material by coating the material with a conjugate composition comprising glycosaminoglycans to a substantial degree covalently linked to an amino-group containing species by —CO—CH$_2$—NH— said —COCH$_2$— portion being derived from said glycosaminoglycans and said —NH— portion being derived from an amino group of said species, wherein the glycosaminoglycan is heparin or a fragment thereof, and the species is antithrombin III.

3. A method for coating a medical device or prosthetic device comprising applying covalent conjugates to the device to form a coating on the device wherein the covalent conjugate comprises heparin linked to antithrombin III wherein the antithrombin III is directly covalently linked via its amino group to a terminal aldose residue of the heparin and the covalent linkage comprises an imine (>C=N—) formed between the amino group and C1 of the terminal aldose or the amine reduction product thereof (>CH—NH—), or a pharmaceutically acceptable salt thereof.

4. A method of forming a coating on a surface of a medical or prosthetic device comprising applying a product on the surface that is prepared by (a) incubating heparin with antithrombin III under conditions which allow imine formation between the terminal aldose residue of the heparin and an amine of the antithrombin III and (b) allowing Amadori rearrangement to an α-carbonyl amine.

5. A method of imparting antithrombotic properties to a surface comprising modifying the surface with covalent conjugates wherein the covalent conjugates comprise heparin linked to antithrombin III wherein the antithrombin III is directly covalently linked via its amino group to a terminal aldose residue of the heparin and the covalent linkage comprises an imine (>C=N—) formed between the amino group and C1 of the terminal aldose or the amine reduction product thereof (>CH—NH—), or a pharmaceutically acceptable salt thereof.

* * * * *